US008426422B2

(12) United States Patent
Hexamer et al.

(10) Patent No.: US 8,426,422 B2
(45) Date of Patent: Apr. 23, 2013

(54) APOPTOSIS-INDUCING AGENTS FOR THE TREATMENT OF CANCER AND IMMUNE AND AUTOIMMUNE DISEASES

(75) Inventors: Laura A. Hexamer, Grayslake, IL (US); Hong Ding, Gurnee, IL (US); Steven W. Elmore, Northbrook, IL (US); Aaron R. Kunzer, Arlington Heights, IL (US); Xiaohong Song, Grayslake, IL (US); Andrew J. Souers, Evanston, IL (US); Gerard M. Sullivan, Lake Villa, IL (US); Zhi-Fu Tao, Gurnee, IL (US); Michael D. Wendt, Vernon Hills, IL (US)

(73) Assignee: Abbvie Inc., North Chicago, IL (US)

( * ) Notice: Subject to any disclaimer, the term of this patent is extended or adjusted under 35 U.S.C. 154(b) by 214 days.

(21) Appl. No.: 12/689,106

(22) Filed: Jan. 18, 2010

(65) Prior Publication Data
US 2010/0184750 A1  Jul. 22, 2010

Related U.S. Application Data

(60) Provisional application No. 61/145,627, filed on Jan. 19, 2009.

(51) Int. Cl.
*A61K 31/496* (2006.01)
*C07D 209/08* (2006.01)
*C07D 213/71* (2006.01)
*C07D 231/56* (2006.01)
*C07D 235/04* (2006.01)
*C07D 265/02* (2006.01)
*C07D 285/14* (2006.01)
*C07D 311/14* (2006.01)
*C07D 295/155* (2006.01)

(52) U.S. Cl.
USPC ............ 514/254.09; 514/252.12; 514/253.05; 514/254.11; 544/48; 544/105; 544/360; 544/363; 544/364; 544/370; 544/371; 544/376; 544/400

(58) Field of Classification Search .................. None
See application file for complete search history.

(56) References Cited

U.S. PATENT DOCUMENTS

| 7,390,799 | B2 | 6/2008 | Bruncko et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 7,642,260 | B2 | 1/2010 | Bruncko et al. |
| 7,709,467 | B2 | 5/2010 | Bruncko et al. |
| 7,767,684 | B2 | 8/2010 | Bruncko et al. |
| 7,973,161 | B2 | 7/2011 | Bruncko et al. |
| 8,173,811 | B2 | 5/2012 | Bruncko et al. |
| 2007/0015787 | A1 | 1/2007 | Bruncko et al. |
| 2007/0072860 | A1 | 3/2007 | Bruncko et al. |
| 2008/0076779 | A1 | 3/2008 | Elmore et al. |
| 2008/0182845 | A1 | 7/2008 | Bardwell et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |
| 2010/0022773 | A1 | 1/2010 | Bruncko et al. |
| 2010/0152183 | A1 | 6/2010 | Bruncko et al. |
| 2010/0160322 | A1 | 6/2010 | Bruncko et al. |
| 2010/0184750 | A1 | 7/2010 | Hexamer et al. |
| 2010/0184766 | A1 | 7/2010 | Kunzer et al. |
| 2010/0227838 | A1 | 9/2010 | Shah et al. |
| 2010/0240715 | A1 | 9/2010 | Bruncko et al. |
| 2010/0249133 | A1 | 9/2010 | Bruncko et al. |
| 2010/0298321 | A1 | 11/2010 | Bruncko et al. |
| 2010/0298323 | A1 | 11/2010 | Bruncko et al. |
| 2010/0305122 | A1 | 12/2010 | Bruncko et al. |
| 2011/0124628 | A1 | 5/2011 | Bruncko et al. |
| 2011/0237553 | A1 | 9/2011 | Ding et al. |

FOREIGN PATENT DOCUMENTS

| WO | WO0224636 A2 | 3/2002 |
| WO | WO2004014913 A2 | 2/2004 |
| WO | WO2005032488 A2 | 4/2005 |
| WO | WO2005049593 A2 | 6/2005 |
| WO | WO2005049594 A1 | 6/2005 |
| WO | WO2008024337 A2 | 2/2008 |
| WO | WO2008/033747 | 3/2008 |
| WO | WO2009/036035 | 3/2009 |
| WO | WO2009/036051 | 3/2009 |
| WO | 2010065824 A2 | 6/2010 |
| WO | 2010065865 A2 | 6/2010 |
| WO | 2010083441 A2 | 7/2010 |

OTHER PUBLICATIONS

Burger's Medicinal Chemistry, edited by Manfred E. Wolff, 5th Ed. Part 1, pp. 975-977 (1995).*
Banker et al. "Modern Pharmaceutics", 3rd Ed. p. 596 (1996).*
Testa et al. Pure Appl. Chem. vol. 76, pp. 907-914 (2004).*
Beylot M., et al., "In vivo studies of intrahepatic metabolic pathways," Diabetes Metabolism, 1997, 23 (3), 251-257.
Blagojevic N., et al., "Role of heavy water in Boron Neutron Capture Therapy," in Topics in Dosimetry & Treatment Planning for Neutron Capture Therapy, Advanced Medical Publishing, Madison, WI, 1994, 125-134.
Blake et al., "Studies with deuterated drugs," J. Pharm. Sci., 1975, 64 (3), 367-391.

(Continued)

Primary Examiner — Emily Bernhardt
(74) Attorney, Agent, or Firm — Jones Day

(57) ABSTRACT

Disclosed are compounds which inhibit the activity of anti-apoptotic Bcl-2 proteins, compositions containing the compounds and methods of treating diseases during which is expressed anti-apoptotic Bcl-2 protein.

4 Claims, No Drawings

OTHER PUBLICATIONS

Brickner S. J., et al., "Synthesis and antibacterial activity of U-100592 and U-100766, two oxazolidinone antibacterial agents for the potential treatment of multidrug-resistant gram-positive bacterial infections," J Med Chem., 1996, 39 (3), 673-679.
Bruncko M., et al, "Studies leading to potent, dual inhibitors of Bcl-2 and Bcl-xL" Journal of Medicinal Chemistry, 2007, 50 (4), 641-662.
Czajka D. M., "Effect of deuterium oxide on the reproductive potential of mice," Ann NY Acad Sci, 1960, vol. 84, pp. 770-779.
Czajka D.M., et al., "Physiological effects of deuterium on dogs," Am. J. Physiol., 1961, 201 (2), 357-362.
Eliel, E. L. et al., "Stereochemistry of Organic Compounds," 1994, pp. 119-120, 1206, John Wiley & Sons, Inc. New York.
Foster, A.B., et al., "Deuterium Isotope Effects in the Metabolism of Drugs and Xenobiotics: Implications for Drug Design," Advances in Drug Research, 1985, 14, Academic Press, London, 2-36.
Holzelova et al., "Autoimmune Lymphoproliferative Syndrome with Somatic Fas Mutations," New England Journal of Medicine, 2004, 351, pp. 1409-1418.
International Search Report for Application No. PCT/US2010/021243, mailed Jul. 13, 2010, 6 pages.
International Search Report for Publication No. PCT/US2010/021245, mailed Apr. 1, 2010, 3 pages.
IUPAC Commission on Nomenclature of Organic Chemistry: Rules for the Nomenclature of Organic Chemistry Section E: Stereochemistry, Pure Appl Chem, 1976, 45, 11-30.
Jones C.D et al., "Effects of Substituent Modification on Face Selection in Reduction," Journal Org. Chem, 1998, pp. 2758-2760, vol. 63.
Kato et al., "Synthesis of Deuterated Mosapride Citrate," J. Labelled Comp. Radiopharmaceut, 1995, 36 (10), 927-932.
Korolkova, A., "Essentials of Medicinal Chemistry," John Wiley-Interscience Publications, John Wiley & Sons, Nem York, pp. 97-118, 1988.
Kushner et al., "Pharmacological uses and perspectives of heavy water and deuterated compounds," Can J Physiol Pharmacol, 1999, vol. 77, pp. 79-88.
Lizondo J., et al., "Linezolid: Oxazolidinone antibacterial," Drugs of the Future, 1996, 21 (11), 1116-1123.
Mallesham B., et al., "Highly efficient CuI-catalyzed coupling of aryl bromides with oxazolidinones using Buchwald's protocol: a short route to linezolid and toloxatone," Org. Lett., 2003, 5 (7), 963-965.
Park C.M., et al., "Discovery of an orally bioavailable small molecule inhibitor of prosurvival B-cell lymphoma 2 proteins," Journal of Medicinal Chemistry, 2008, 51 (21), 6902-6915.
Puck,et al., "Immune Disorders Caused by Defects in the Caspase Cascade," Current Allergy and Asthma Reports, 2003, 3, pp. 378-384.
Rengan. et al., "Actin cytoskeletal function is spared, but apoptosis is increased, in WAS patient hematopoietic cells," Blood, 2000, 95 -Issue 4, pp. 1283-1292.
Shimazaki et al., "Evaluation of apoptosis as a prognostic factor in myelodysplastic syndromes", British J Haematology, 2000, 110 Issue 3, pp. 584-590.
Sutton V.R., et al. "Bcl-2 prevents apoptosis induced by perforin and granzyme B, but not that mediated by whole cytotoxic lymphocytes", Journal of Immunology, 1997, 158 (12), pp. 5783-5790.
Thomson J. F., "Physiological effects of D20 in mammals," Ann. New York Acad. Sci., 1960, 84, 736-744.
Tse et al., "ABT-263: A Potent and Orally Bioavailable Bcl-2 Family Inhibitor," Cancer Research, 2008, 68 (9), pp. 3421-3428.
Wang Z.X., "An exact mathematical expression for describing competitive binding of two different ligands to a protein molecule", FEBS Lett, 1995; 360 (2): pp. 111-114.
European Patent Office, Extended European Search Report, Application No. EP12 16 3746, 2012 Sep. 7, 2012.

* cited by examiner

APOPTOSIS-INDUCING AGENTS FOR THE TREATMENT OF CANCER AND IMMUNE AND AUTOIMMUNE DISEASES

This application claims priority to U.S. Provisional Application Ser. No. 61/145627, filed Jan. 19, 2009, which is incorporated by reference in its entirety.

FIELD OF THE INVENTION

This invention pertains to compounds which inhibit the activity of Bcl-2 anti-apoptotic proteins, compositions containing the compounds, and methods of treating diseases during which anti-apoptotic Bcl-2 proteins are expressed.

BACKGROUND OF THE INVENTION

Anti-apoptotic Bcl-2 proteins are associated with a number of diseases. There is therefore an existing need in the therapeutic arts for compounds which inhibit the activity of anti-apoptotic Bcl-2 proteins.

Overexpression of Bcl-2 proteins correlates with resistance to chemotherapy, clinical outcome, disease progression, overall prognosis or a combination thereof in various cancers and disorders of the immune system.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in Current Allergy and Asthma Reports 2003, 3, 378-384; British Journal of Haematology 2000, 110 (3), 584-90; Blood 2000, 95(4), 1283-92; and New England Journal of Medicine 2004, 351(14), 1409-1418. Involvement of Bcl-2 proteins in arthritis is disclosed in commonly-owned U.S. Provisional Patent Application Ser. No. 60/988,479. Involvement of Bcl-2 proteins in bone marrow transplant rejection is disclosed in commonly-owned U.S. patent application Ser. No. 11/941,196.

SUMMARY OF THE INVENTION

One embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula I

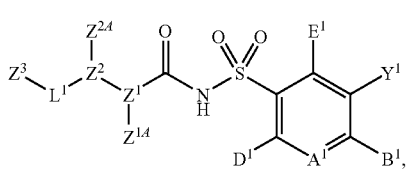

wherein
$A^1$ is N or $C(A^2)$;
$A^2, B^1, D^1, E^1$, and $Y^1$ are independently selected H, OH, F, Cl, Br, I, CN, $CF_3$, C(O)OH, C(O)$NH_2$, C(O)$OR^{1A}$; $NO_2$, $OCF_3$, $CF_2CF_3$, $OCF_2CF_3$, $NH_2$, C(O)$NH_2$, $NR^1C(O)R^1$, $NR^1S(O)_2R^1$, $NR^1C(O)OR^1$, NHC(O)$NH_2$, NHC(O)$NHR^1$, NHC(O)$N(R^1)_2$, C(O)NHOH, C(O)$NHOR^1$, C(O)$NHSO_2R^1$, $SO_2NH_2$, C(O)H, C(N)$NH_2$, C(N)$NHR^1$, C(N)$N(R^1)_2$, CNOH, $CNOCH_3$, $N_3$, or NHS(O)$R^1$;
or
$E^1$ and $Y^1$, together with the atoms to which they are attached, are benzene, naphthylene, heteroarene, cycloalkane, cycloalkene, heterocycloalkane or heterocycloalkene; and
$A^2, B^1$, and $D^1$ are independently selected H, OH, F, Cl, Br, I, CN, $CF_3$, C(O)OH, C(O)$NH_2$, C(O)$OR^{1A}$, $NO_2$, $OCF_3$, $CF_2CF_3$, $OCF_2CF_3$, $NH_2$, C(O)$NH_2$, $NR^1C(O)R^1$, $NR^1S(O)_2R^1$, $NR^1C(O)OR^1$, NHC(O)$NH_2$, NHC(O)$NHR^1$, NHC(O)$N(R^1)_2$, C(O)NHOH, C(O)$NHOR^1$, C(O)$NHSO_2R^1$, $SO_2NH_2$, C(O)H, C(N)$NH_2$, C(N)$NHR^1$, C(N)$N(R^1)_2$, CNOH, $CNOCH_3$, $N_3$, or NHS(O)$R^1$;
or
$Y^1$ and $B^1$, together with the atoms to which they are attached, are benzene, naphthylene, heteroarene, cycloalkane, cycloalkene, heterocycloalkane or heterocycloalkene; and
$A^2, D^1$, and $E^1$ are independently selected H, OH, F, Cl, Br, I, CN, $CF_3$, C(O)OH, C(O)$NH_2$, C(O)$OR^{1A}$, $NO_2$, $OCF_3$, $CF_2CF_3$, $OCF_2CF_3$, $NH_2$, C(O)$NH_2$, $NR^1C(O)R^1$, $NR^1S(O)_2R^1$, $NR^1C(O)OR^1$, NHC(O)$NH_2$, NHC(O)$NHR^1$, NHC(O)$N(R^1)_2$, C(O)NHOH, C(O)$NHOR^1$, C(O)$NHSO_2R^1$, $SO_2NH_2$, C(O)H, C(N)$NH_2$, C(N)$NHR^1$, C(N)$N(R^1)_2$, CNOH, $CNOCH_3$, $N_3$, or NHS(O)$R^1$;
or
$A^2$ and $B^1$, together with the atoms to which they are attached, are benzene, naphthylene, heteroarene, cycloalkane, cycloalkene, heterocycloalkane or heterocycloalkene; and
$D^1, E^1$, and $Y^1$ are independently selected H, OH, F, Cl, Br, I, CN, $CF_3$, C(O)OH, C(O)$NH_2$, C(O)$OR^{1A}$, $NO_2$, $OCF_3$, $CF_2CF_3$, $OCF_2CF_3$, $NH_2$, C(O)$NH_2$, $NR^1C(O)R^1$, $NR^1S(O)_2R^1$, $NR^1C(O)OR^1$, NHC(O)$NH_2$, NHC(O)$NHR^1$, NHC(O)$N(R^1)_2$, C(O)NHOH, C(O)$NHOR^1$, C(O)$NHSO_2R^1$, $SO_2NH_2$, C(O)H, C(N)$NH_2$, C(N)$NHR^1$, C(N)$N(R^1)_2$, CNOH, $CNOCH_3$, $N_3$, or NHS(O)$R^1$;
or
$A^2$ and $D^1$, together with the atoms to which they are attached, are benzene, naphthalene, heteroarene, cycloalkane, cycloalkene, heterocycloalkane or heterocycloalkene; and
$B^1, E^1$, and $Y^1$ are independently selected H, OH, F, Cl, Br, I, CN, $CF_3$, C(O)OH, C(O)$NH_2$, C(O)$OR^{1A}$, $NO_2$, $OCF_3$, $CF_2CF_3$, $OCF_2CF_3$, $NH_2$, C(O)$NH_2$, $NR^1C(O)R^1$, $NR^1S(O)_2R^1$, $NR^1C(O)OR^1$, NHC(O)$NH_2$, NHC(O)$NHR^1$, NHC(O)$N(R^1)_2$, C(O)NHOH, C(O)$NHOR^1$, C(O)$NHSO_2R^1$, $SO_2NH_2$, C(O)H, C(N)$NH_2$, C(N)$NHR^1$, C(N)$N(R^1)_2$, CNOH, $CNOCH_3$, $N_3$, or NHS(O)$R^1$;
$R^1$ is $R^2, R^3, R^4$ or $R^5$;
$R^{1A}$ is cycloalkyl, cycloalkenyl or cycloalkynyl;
$R^2$ is phenyl, which is unfused or fused with benzene, heteroarene or $R^{2A}$; $R^{2A}$ is cycloalkane, cycloalkene, heterocycloalkane or heterocycloalkene;
$R^3$ is heteroaryl, which is unfused or fused with benzene, heteroarene or $R^{3A}$; $R^{3A}$ is cycloalkane, cycloalkene, heterocycloalkane or heterocycloalkene;
$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, $OH$, $(O)$, $C(O)OH$, $(O)$, $N_3$, $CN$, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(O)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$Z^1$ is $R^{26}$ or $R^{27}$;

$Z^2$ is $R^{28}$, $R^{29}$ or $R^{30}$;

$Z^{1A}$ and $Z^{2A}$ are both absent or are taken together to form $CH_2$, $CH_2CH_2$ or $Z^{12A}$;

$Z^{12A}$ is $C_2$-$C_6$-alkylene having one or two $CH_2$ moieties replaced by NH, $N(CH_3)$, S, S(O) or $SO_2$;

$L^1$ is a $R^{37}$, $OR^{37}$, $SR^{37}$, $S(O)R^{37}$, $SO_2R^{37}$, $C(O)R^{37}$, $CO(O)R^{37}$, $OC(O)R^{37}$, $OC(O)OR^{37}$, $NHR^{37}$, $C(O)NH$, $C(O)NR^{37}$, $C(O)NHOR^{37}$, $C(O)NHSO_2R^{37}$, $SO_2NH$, $SO_2NHR^{37}$, $C(N)NH$, $C(N)NHR^{37}$;

$R^{26}$ is phenylene which is unfused or fused with benzene or heteroarene or $R^{26A}$; $R^{26A}$ is cycloalkane, cycloalkene, heterocycloalkane or heterocycloalkene;

$R^{27}$ is heteroarylene, which is unfused or fused with benzene or heteroarene or $R^{27A}$; $R^{27A}$ is cycloalkane, cycloalkene, heterocycloalkane or heterocycloalkene;

$R^{28}$ is phenylene, which is unfused or fused with benzene, heteroarene or $R^{28A}$; $R^{28A}$ is cycloalkane, cycloalkene, heterocycloalkane or heterocycloalkene;

$R^{29}$ is heteroarylene, which is unfused or fused with benzene or heteroarene or $R^{29A}$; $R^{29A}$ is cycloalkane, cycloalkene, heterocycloalkane or heterocycloalkene;

$R^{30}$ is cycloalkylene, cycloalkenylene, heterocycloalkylene or heterocycloalkenylene, each of which is unfused or fused with benzene, heteroarene or $R^{30A}$; $R^{30A}$ is cycloalkane, cycloalkene, heterocycloalkane or heterocycloalkene;

$R^{37}$ is a bond or $R^{37A}$;

$R^{37A}$ is alkylene, alkenylene, or alkynylene, each of which is unsubstituted or substituted with one or two or three independently selected $R^{37B}$, $OR^{37B}$, $SR^{37B}$, $S(O)R^{37B}$, $SO_2R^{37B}$, $C(O)R^{37B}$, $CO(O)R^{37B}$, $OC(O)R^{37B}$, $OC(O)OR^{37B}$, $NH_2$, $NHR^{37B}$, $N(R^{37B})_2$, $NHC(O)R^{37B}$, $NR^{37B}C(O)R^{37B}$, $NHS(O)_2R^{37B}$, $NR^{37B}S(O)_2R^{37B}$, $NHC(O)OR^{37B}$, $NR^{37B}C(O)OR^{37B}$, $NHC(O)NH_2$, $NHC(O)NHR^{37B}$, $NHC(O)N(R^{37B})_2$, $NR^{37B}C(O)NHR^{37B}$, $NR^{37B}C(O)N(R^{37B})_2$, $C(O)NH_2$, $C(O)NHR^{37B}$, $C(O)N(R^{37B})_2$, $C(O)NHOH$, $C(O)NHOR^{37B}$, $C(O)NHSO_2R^{37B}$, $C(O)NR^{37B}SO_2R^{37B}$, $SO_2NH_2$, $SO_2NHR^{37B}$, $SO_2N(R^{37B})_2$, $C(O)H$, $C(O)OH$, $C(N)NH_2$, $C(N)NHR^{37B}$, $C(N)N(R^{37B})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{37B}$ is alkyl, alkenyl, alkynyl, phenyl, heteroaryl, cycloalkyl, cycloalkenyl, heterocycloalkyl, or heterocycloalkenyl;

$Z^3$ is $R^{38}$, $R^{39}$ or $R^{40}$;

$R^{38}$ is phenyl, which is unfused or fused with benzene, heteroarene or $R^{38A}$; $R^{38A}$ is cycloalkane, cycloalkene, heterocycloalkane or heterocyclalkene;

$R^{39}$ is heteroaryl, which is unfused or fused with benzene, heteroarene or $R^{39A}$; $R^{39A}$ is cycloalkane, cycloalkene, heterocycloalkane or heterocycloalkene;

$R^{40}$ is cycloalkyl, cycloalkenyl, heterocycloalkyl, or heterocycloalkenyl, each of which is unfused or fused with benzene, heteroarene or $R^{40A}$; $R^{40A}$ is cycloalkane, cycloalkene, heterocycloalkane or heterocycloalkene;

wherein the moieties represented by $R^{26}$ and $R^{27}$ are unsubstituted or substituted, (i.e., if $Z^{1A}$ and $Z^{2A}$ are absent) or further unsubstituted or further substituted (i.e., if $Z^{1A}$ and $Z^{2A}$ are present) with one or more $R^{41}$, $OR^{41}$, $SR^{41}$, $S(O)R^{41}$, $SO_2R^{41}$, $C(O)R^{41}$, $CO(O)R^{41}$, $OC(O)R^{41}$, $OC(O)OR^{41}$, $NH_2$, $NHR^{41}$, $N(R^{41})_2$, $NHC(O)R^{41}$, $NR^{41}C(O)R^{41}$, $NHS(O)_2R^{41}$, $NR^{41}S(O)_2R^{41}$, $NHC(O)OR$ $C(O)OR^{41}$, $NHC(O)NH_2$, $NHC(O)NHR^{41}$, $NHC(O)N(R^{41})_2$, $NR^{41}C(O)NHR^{41}$, $NR^{41}C(O)N(R^{41})_2$, $C(O)NH_2$, $C(O)NHR^{41}$, $C(O)N(R^{41})_2$, $C(O)NHOH$, $C(O)NHOR^{41}$, $C(O)NHSO_2R^{41}$, $C(O)NR^{41}SO_2R^{41}$, $SO_2NH_2$, $SO_2NHR^{41}$, $SO_2N(R^{41})_2$, $C(O)H$, $C(O)OH$, $C(N)NH_2$, $C(N)NHR^{41}$, $C(N)N(R^{41})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{41}$ is $R^{42}$, $R^{43}$, $R^{44}$ or $R^{45}$;

$R^{42}$ is phenyl, which is unfused or fused with benzene, heteroarene or $R^{42A}$; $R^{42A}$ is cycloalkane, cycloalkene, heterocycloalkane or heterocycloalkene;

$R^{43}$ is heteroaryl, which is unfused or fused with benzene, or $R^{43A}$; $R^{43A}$ is cycloalkane, cycloalkene, heterocycloalkane or heterocycloalkene;

$R^{44}$ is cycloalkyl, cycloalkenyl, heterocycloalkyl, or heterocycloalkenyl, each of which is unfused or fused with benzene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $SR^{46}$, $S(O)R^{46}$, $SO_2R^{46}$, $C(O)R^{46}$, $CO(O)R^{46}$, $OC(O)R^{46}$, $OC(O)OR^{46}$, $NH_2$, $NHR^{46}$, $N(R^{46})_2$, $NHC(O)R^{46}$, $NR^{46}C(O)R^{46}$, $NHS(O)_2R^{46}$, $NR^{46}S(O)_2R^{46}$, $NHC(O)OR^{46}$, $NR^{46}C(O)OR^{46}$, $NHC(O)NH_2$, $NHC(O)NHR^{46}$, $NHC(O)N(R^{46})_2$, $NR^{46}C(O)NHR^{46}$, $NR^{46}C(O)N(R^{46})_2$, $C(O)NH_2$, $C(O)NHR^{46}$, $C(O)N(R^{46})_2$, $C(O)NHOH$, $C(O)NHOR^{46}$, $C(O)NHSO_2R^{46}$, $C(O)NR^{46}SO_2R^{46}$, $SO_2NH_2$, $SO_2NHR^{46}$, $SO_2N(R^{46})_2$, $C(O)H$, $C(O)OH$, $C(N)NH_2$, $C(N)NHR^{46}$, $C(N)N(R^{46})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{46}$ is alkyl, alkenyl, alkynyl, $R^{47}$, $R^{48}$ or $R^{49}$;

$R^{47}$ is phenyl, which is unfused or fused with benzene, heteroarene or $R^{47A}$; $R^{47A}$ is cycloalkane, cycloalkene, heterocycloalkane or heterocycloalkene;

$R^{48}$ is heteroaryl, which is unfused or fused with benzene, heteroarene or $R^{48A}$; $R^{48A}$ is cycloalkane, cycloalkene, heterocycloalkane or heterocycloalkene;

$R^{49}$ is cycloalkyl, cycloalkenyl, heterocycloalkyl, or heterocycloalkenyl, each of which is unfused or fused with benzene, heteroarene or $R^{49A}$; $R^{49A}$ is cycloalkane, cycloalkene, heterocycloalkane or heterocycloalkene;

wherein the cyclic moieties represented by $E^1$ and $Y^1$ together, $Y^1$ and $B^1$ together, $A^2$ and $B^1$ togetger, $A^2$ and $D^1$ together, $R^{1A}$, $R^2$, $R^{2A}$, $R^3$, $R^{3A}$, $R^4$, $R^{4A}$, $R^6$, $R^{6C}$, $R^8$, $R^{8A}$, $R^{9A}$, $R^{10}$, $R^{10A}$, $R^{13}$, $R^{13A}$, $R^{14}$, $R^{14A}$, $R^{15}$, $R^{15A}$, $R^{28}$, $R^{28A}$, $R^{29}$, $R^{29A}$, $R^{30}$, $R^{30A}$, $R^{37B}$, $R^{38}$, $R^{38A}$, $R^{39}$, $R^{39A}$, $R^{40}$, and $R^{40A}$ are independently unsubstituted, further unsubstituted, substituted or further substituted with one or more independently selected $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl, or alkynyl, each of which is unsubstituted or substituted with one or two or three independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl, or alkenyl, each of which is unsubstituted or substituted with one or two or three independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{67}$ is alkyl, alkenyl, alkynyl, phenyl, heteroaryl, cycloalkyl, cycloalkenyl, heterocycloalkyl or heterocycloalkenyl;

wherein the cyclic moieties represented by $R^{58}$, $R^{59}$, $R^{60}$, $R^{63}$, $R^{64}$, $R^{65}$, and $R^{67}$ are unsubstituted or substituted with one or more independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{68}$ is $R^{69}$, $R^{70}$, $R^{71}$ or $R^{72}$;

$R^{69}$ is phenyl, which is unfused or fused with benzene, heteroarene or $R^{69A}$; $R^{69A}$ is cycloalkane, cycloalkene, heterocycloalkane or heterocycloalkene;

$R^{70}$ is heteroaryl, which is unfused or fused with benzene, heteroarene or $R^{70A}$; $R^{70A}$ is cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with benzene, heteroarene or $R^{71A}$; $R^{71A}$ is cycloalkane, cycloalkene, heterocycloalkane or heterocycloalkene;

$R^{72}$ is alkyl, alkenyl, or alkenyl, each of which is unsubstituted or substituted with one or two or three independently selected $R^{73}$, $OR^{73}$, $SR^{73}$, $S(O)R^{73}$, $SO_2R^{73}$, $C(O)R^{73}$, $CO(O)R^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{73}$ is alkyl, alkenyl, alkenyl, phenyl, heteroaryl, cycloalkyl, cycloalkenyl, heterocycloalkyl, or heterocycloalkenyl; and the moieties represented by $R^{69}$, $R^{70}$, and $R^{71}$ are unsubstituted or substituted with one or more independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, $(O)$, $CN$, $N_3$, $NO_2$, $CF_3$, $CF_2CF_3$, $OCF_3$, $OCF_2CF_3$, F, Cl, Br or I substituents.

In another embodiment of Formula (I), $A^1$ is N or $C(A^2)$;

$A^2$, $B^1$, $D^1$, $E^1$, and $Y^1$ are independently selected H, OH, F, Cl, Br, I, CN, $CF_3$, or $NO_2$;

or $E^1$ and $Y^1$, together with the atoms to which they are attached, are benzene or heteroarene, and $A^2$, $B^1$, and $D^1$ are independently selected H;

or $Y^1$ and $B^1$, together with the atoms to which they are attached, are benzene, and $A^2$, $D^1$, and $E^1$ are independently selected H;

or $A^2$ and $B^1$, together with the atoms to which they are attached, are heteroarene, cycloalkane, heterocycloalkane or heterocycloalkene; and $D^1$, $E^1$, and $Y^1$ are independently selected H, F, Cl, Br, I, or $NO_2$;

$Z^1$ is $R^{26}$;

$Z^2$ is $R^{30}$;

$Z^{1A}$ and $Z^{2A}$ are both absent;

$L^1$ is a $R^{37}$;

$R^{26}$ is phenylene;

$R^{30}$ is heterocycloalkylene;

$R^{37}$ is $R^{37A}$;

$R^{37A}$ is alkylene or alkenylene, each of which is unsubstituted or substituted with $R^{37B}$;

$R^{37B}$ is phenyl;

$Z^3$ is $R^{38}$ or $R^{40}$;

$R^{38}$ is phenyl;

$R^{40}$ is cycloalkenyl;

wherein the moieties represented by $R^{26}$ and $R^{27}$ are unsubstituted or substituted, (i.e., if $Z^{1A}$ and $Z^{2A}$ are absent) or further unsubstituted or further substituted (i.e., if $Z^{1A}$ and $Z^{2A}$ are present) with one or more $R^{41}$; $OR^{41}$; $SR^{41}$; $S(O)R^{41}$; $SO_2R^{41}$, or $NHR^{41}$ substituents;

$R^{41}$ is $R^{42}$ or $R^{45}$;

$R^{42}$ is phenyl, which is unfused or fused with heteroarene;

$R^{45}$ is alkyl, which is unsubstituted or substituted with one or two independently selected $R^{46}$;

$R^{46}$ is $R^{47}$;

$R^{47}$ is phenyl;

wherein the cyclic moieties represented by $E^1$ and $Y^1$ together, $Y^1$ and $B^1$ together, $A^2$ and $B^1$ together, $R^{30}$, $R^{30A}$; $R^{37B}$; $R^{38}$, and $R^{40}$ are independently unsubstituted, further unsubstituted, substituted or further substituted with one or more independently selected $R^{57}$, $OR^{57}$, $NR^{57}C(O)R^{57}$, or (O);

$R^{57}$ is $R^{58}$, or $R^{61}$;

$R^{58}$ is phenyl, $R^{61}$ is alkyl, which is unsubstituted or substituted with one or two or three independently selected $N(R^{62})_2$, or F, Cl, Br or I substituents;

$R^{62}$ is $R^{66}$;

$R^{66}$ is alkyl; and wherein the cyclic moiety represented by $R^{58}$ is unsubstituted or substituted with one or more independently selected F, Cl, Br or I substituents.

In another embodiment of Formula (I), $A^1$ is N or $C(A^2)$;

$A^2$, $B^1$, $D^1$, $E^1$, and $Y^1$ are independently selected H, OH, F, Cl, Br, I, CN, $CF_3$, or $NO_2$;

or $E^1$ and $Y^1$, together with the atoms to which they are attached, are benzene or heteroarene, and $A^2$, $B^1$, and $D^1$ are independently selected H;

or $Y^1$ and $B^1$, together with the atoms to which they are attached, are benzene, and $A^2$, $D^1$, and $E^1$ are independently selected H;

or $A^2$ and $B^1$, together with the atoms to which they are attached, are heteroarene, cycloalkane, heterocycloalkane or heterocycloalkene; and $D^1$, $E^1$, and $Y^1$ are independently selected H, F, Cl, Br, I, or $NO_2$;

$Z^1$ is $R^{26}$;

$Z^2$ is $R^{30}$;

$Z^{1A}$ and $Z^{2A}$ are both absent;

$L^1$ is a $R^{37}$;

$R^{26}$ is phenylene;

$R^{30}$ is heterocycloalkylene;

$R^{37}$ is $R^{37A}$;

$R^{37A}$ is alkylene or alkenylene, each of which is unsubstituted or substituted with $R^{37B}$;

$R^{37B}$ is phenyl;

$Z^3$ is $R^{38}$ or $R^{40}$;

$R^{38}$ is phenyl;

$R^{40}$ is cycloalkenyl;

wherein the moieties represented by $R^{26}$ and $R^{27}$ are unsubstituted or substituted, (i.e., if $Z^{1A}$ and $Z^{2A}$ are absent) or further unsubstituted or further substituted (i.e., if $Z^{1A}$ and $Z^{2A}$ are present) with one or more $R^{41}$, $OR^{41}$, $SR^{41}$, $S(O)R^{41}$, $SO_2R^{41}$, or $NHR^{41}$ substituents;

$R^{41}$ is $R^{42}$ or $R^{45}$;

$R^{42}$ is phenyl, which is unfused or fused with heteroarene;

$R^{45}$ is alkyl, which is unsubstituted or substituted with one or two independently selected $R^{46}$;

$R^{46}$ is $R^{47}$;

$R^{47}$ is phenyl;

wherein the cyclic moieties represented by $E^1$ and $Y^1$ together, $Y^1$ and $B^1$ together, $A^2$ and $B^1$ together, $R^{30}$, $R^{30A}$, $R^{37B}$, $R^{38}$, and $R^{40}$ are independently unsubstituted, further unsubstituted, substituted or further substituted with one or more independently selected $R^{57}$, $OR^{57}$, $NR^{57C}(O)R^{57}$, or (O);

$R^{57}$ is $R^{58}$, or $R^{61}$;

$R^{58}$ is phenyl, $R^{61}$ is alkyl, which is unsubstituted or substituted with one or two or three independently selected $N(R^{62})_2$, or F, Cl, Br or I substituents;

$R^{62}$ is $R^{66}$;

$R^{66}$ is alkyl; and wherein the cyclic moiety represented by $R^{58}$ is unsubstituted or substituted with one or more independently selected F, Cl, Br or I substituents.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula IV,

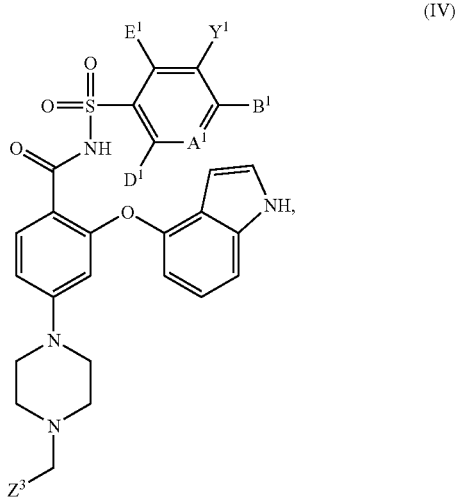

(IV)

wherein $A^1$ is N or $C(A^2)$;

$A^2$, $B^1$, $D^1$, $E^1$, and $Y^1$ are independently selected H, OH, F, Cl, Br, I, CN, $CF_3$, C(O)OH, $C(O)NH_2$, $C(O)OR^{1A}$, $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

or $E^1$ and $Y^1$, together with the atoms to which they are attached, are benzene, naphthylene, heteroarene, cycloalkane, cycloalkene, heterocycloalkane or heterocycloalkene; and $A^2$, $B^1$, and $D^1$ are independently selected H, OH, F, Cl, Br, I, CN, $CF_3$, C(O)OH, $C(O)NH_2$, $C(O)OR^{1A}$, $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

or $Y^1$ and $B^1$, together with the atoms to which they are attached, are benzene, naphthylene, heteroarene, cycloalkane, cycloalkene, heterocycloalkane or heterocycloalkene; and $A^2$, $D^1$, and $E^1$ are independently selected H, OH, F, Cl, Br, I, CN, $CF_3$, C(O)OH, $C(O)NH_2$, $C(O)OR^{1A}$, $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

or $A^2$ and $B^1$, together with the atoms to which they are attached, are benzene, naphthylene, heteroarene, cycloalkane, cycloalkene, heterocycloalkane or heterocycloalkene; and $D^1$, $E^1$, and $Y^1$ are independently selected H, OH, F, Cl, Br, I, CN, $CF_3$, C(O)OH, $C(O)NH_2$, $C(O)OR^{1A}$, $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

or $A^2$ and $D^1$, together with the atoms to which they are attached, are benzene, naphthalene, heteroarene, cycloalkane, cycloalkene, heterocycloalkane or heterocycloalkene; and $B^1$, $E^1$, and $Y^1$ are independently selected H, OH, F, Cl, Br, I, CN, $CF_3$, C(O)OH, $C(O)NH_2$, $C(O)OR^{1A}$, $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with benzene, heteroarene or $R^{2A}$; $R^{2A}$ is cycloalkane, cycloalkene, heterocycloalkane or heterocycloalkene;

$R^3$ is heteroaryl, which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{12}$ is R$^{13}$, R$^{14}$, R$^{15}$ or R$^{16}$;

R$^{13}$ is phenyl, which is unfused or fused with benzene, heteroarene or R$^{13A}$; R$^{13A}$ is cycloalkane, cycloalkene, heterocycloalkane or heterocycloalkene;

R$^{14}$ is heteroaryl, which is unfused or fused with benzene, heteroarene or R$^{14A}$; R$^{14A}$ is cycloalkane, cycloalkene, heterocycloalkane or heterocycloalkene;

R$^{15}$ is cycloalkane, cycloalkene, heterocycloalkane or heterocycloalkene, each of which is unfused or fused with benzene, heteroarene or R$^{15A}$; R$^{15A}$ is cycloalkane, cycloalkene, heterocycloalkane or heterocycloalkene;

R$^{16}$ is alkyl, alkenyl or alkynyl;

Z$^3$ is R$^{38}$, R$^{39}$ or R$^{40}$;

R$^{38}$ is phenyl, which is unfused or fused with benzene, heteroarene or R$^{38A}$; R$^{38A}$ is cycloalkane, cycloalkene, heterocycloalkane or heterocyclalkene;

R$^{39}$ is heteroaryl, which is unfused or fused with benzene, heteroarene or R$^{39A}$; R$^{39A}$ is cycloalkane, cycloalkene, heterocycloalkane or heterocycloalkene;

R$^{40}$ is cycloalkyl, cycloalkenyl, heterocycloalkyl, or heterocycloalkenyl, each of which is unfused or fused with benzene, heteroarene or R$^{40A}$; R$^{40A}$ is cycloalkane, cycloalkene, heterocycloalkane or heterocycloalkene;

wherein the cyclic moieties represented by E$^1$ and Y$^1$ together, Y$^1$ and B$^1$ together, A$^2$ and B$^1$ to ether A$^2$ and D$^1$ to ether R$^{1A}$, R$^2$, R$^{2A}$, R$^3$, R$^{3A}$, R$^4$, R$^{4A}$, R$^6$, R$^{6C}$, R$^8$, R$^{8A}$, R$^9$, R$^{9A}$, R$^{10}$, R$^{10A}$, R$^{13}$, R$^{13A}$, R$^{14}$, R$^{14A}$, R$^{15}$, R$^{15A}$, R$^{28}$, R$^{28A}$, R$^{29}$, R$^{29A}$, R$^{30}$, R$^{30A}$, R$^{37B}$, R$^{38}$, R$^{38A}$, R$^{39}$, R$^{39A}$, R$^{40}$, and R$^{40A}$ are independently unsubstituted, further unsubstituted, substituted or further substituted with one or more independently selected R$^{57}$, OR$^{57}$, SR$^{57}$, S(O)R$^{57}$, SO$_2$R$^{57}$, C(O)R$^{57}$, CO(O)R$^{57}$, OC(O)R$^{57}$, OC(O)OR$^{57}$, NH$_2$, NHR$^{57}$, N(R$^{57}$)$_2$, NHC(O)R$^{57}$, NR$^{57}$C(O)R$^{57}$, NHS(O)$_2$R$^{57}$, NR$^{57}$S(O)$_2$R$^{57}$, NHC(O)OR$^{57}$, NR$^{57}$C(O)OR$^{57}$, NHC(O)NH$_2$, NHC(O)NHR$^{57}$, NHC(O)N(R$^{57}$)$_2$, NR$^{57}$C(O)NHR$^{57}$, NR$^{57}$C(O)N(R$^{57}$)$_2$, C(O)NH$_2$, C(O)NHR$^{57}$, C(O)N(R$^{57}$)$_2$, C(O)NHOH, C(O)NHOR$^{57}$, C(O)NHSO$_2$R$^{57}$, C(O)NR$^{57}$SO$_2$R$^{57}$, SO$_2$NH$_2$, SO$_2$NHR$^{57}$, SO$_2$N(R$^{57}$)$_2$, C(O)H, C(O)OH, C(N)NH$_2$, C(N)NHR$^{57}$, C(N)N(R$^{57}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{57}$ is R$^{58}$, R$^{59}$, R$^{60}$ or R$^{61}$;

R$^{58}$ is phenyl, which is unfused or fused with benzene, heteroarene or R$^{58A}$; R$^{58A}$ is cycloalkane, cycloalkene, heterocycloalkane or heterocycloalkene;

R$^{59}$ is heteroaryl, which is unfused or fused with benzene, heteroarene or R$^{59A}$; R$^{59A}$ is cycloalkane, cycloalkene, heterocycloalkane or heterocycloalkene;

R$^{60}$ is cycloalkyl, cycloalkenyl, heterocycloalkyl or heterocycloalkenyl, each of which is unfused or fused with benzene, heteroarene or R$^{60A}$; R$^{60A}$ is cycloalkane, cycloalkene, heterocycloalkane or heterocycloalkene;

R$^{61}$ is alkyl, alkenyl, or alkynyl, each of which is unsubstituted or substituted with one or two or three independently selected R$^{62}$, OR$^{62}$, SR$^{62}$, S(O)R$^{62}$, SO$_2$R$^{62}$, C(O)R$^{62}$, CO(O)R$^{62}$, OC(O)R$^{62}$, OC(O)OR$^{62}$, NH$_2$, NHR$^{62}$, N(R$^{62}$)$_2$, NHC(O)R$_{62}$, NR$_{62}$C(O)R$_{62}$, NHS(O)$_2$R$^{62}$, NR$^{62}$S(O)$_2$R$^{62}$, NHC(O)OR$^{62}$, NR$^{62}$C(O)OR$^{62}$, NHC(O)NH$_2$, NHC(O)NHR$^{62}$, NHC(O)N(R$^{62}$)$_2$, NR$^{62}$C(O)NHR$^{62}$, NR$^{62}$C(O)N(R$^{62}$)$_2$, C(O)NH$_2$, C(O)NHR$^{62}$, C(O)N(R$^{62}$)$_2$, C(O)NHOH, C(O)NHOR$^{62}$, C(O)NHSO$_2$R$^{62}$, C(O)NR$^{62}$SO$_2$R$^{62}$, SO$_2$NH$_2$, SO$_2$NHR$^{62}$, SO$_2$N(R$^{62}$)$_2$, C(O)H, C(O)OH, C(N)NH$_2$, C(N)NHR$^{62}$, C(N)N(R$^{62}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{62}$ is R$^{63}$, R$^{64}$, R$^{65}$ or R$^{66}$;

R$^{63}$ is phenyl, which is unfused or fused with benzene, heteroarene or R$^{63A}$; R$^{63A}$ is cycloalkane, cycloalkene, heterocycloalkane or heterocycloalkene;

R$^{64}$ is heteroaryl, which is unfused or fused with benzene, heteroarene or R$^{64A}$; R$^{64A}$ is cycloalkane, cycloalkene, heterocycloalkane or heterocycloalkene;

R$^{65}$ is cycloalkyl, cycloalkenyl, heterocycloalkyl or heterocycloalkenyl, each of which is unfused or fused with benzene, heteroarene or R$^{65A}$; R$^{65A}$ is cycloalkane, cycloalkene, heterocycloalkane or heterocycloalkene;

R$^{66}$ is alkyl, alkenyl, or alkenyl, each of which is unsubstituted or substituted with one or two or three independently selected R$^{67}$, OR$^{67}$, SR$^{67}$, S(O)R$^{67}$, SO$_2$R$^{67}$, C(O)R$^{67}$, CO(O)R$^{67}$, OC(O)R$^{67}$, OC(O)OR$^{67}$, NH$_2$, NHR$^{67}$, N(R$^{67}$)$_2$, NHC(O)R$^{67}$, NR$^{67}$C(O)R$^{67}$, NHS(O)$_2$R$^{67}$, NR$^{67}$S(O)$_2$R$^{67}$, NHC(O)OR$^{67}$, NR$^{67}$C(O)OR$^{67}$, NHC(O)NH$_2$, NHC(O)NHR$^{67}$, NHC(O)N(R$^{67}$)$_2$, NR$^{67}$C(O)NHR$^{67}$, NR$^{67}$C(O)N(R$^{67}$)$_2$, C(O)NH$_2$, C(O)NHR$^{67}$, C(O)N(R$^{67}$)$_2$, C(O)NHOH, C(O)NHOR$^{67}$, C(O)NHSO$_2$R$^{67}$, C(O)NR$^{67}$SO$_2$R$^{67}$, SO$_2$NH$_2$, SO$_2$NHR$^{67}$, SO$_2$N(R$^{67}$)$_2$, C(O)H, C(O)OH, C(N)NH$_2$, C(N)NHR$^{67}$, C(N)N(R$^{67}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{67}$ is alkyl, alkenyl, alkynyl, phenyl, heteroaryl, cycloalkyl, cycloalkenyl, heterocycloalkyl or heterocycloalkenyl;

wherein the cyclic moieties represented by R$^{58}$, R$^{59}$, R$^{60}$, R$^{63}$, R$^{64}$, R$^{65}$, and R$^{67}$ are unsubstituted or substituted with one or more independently selected R$^{68}$, OR$^{68}$, SR$^{68}$, S(O)R$^{68}$, SO$_2$R$^{68}$, C(O)R$^{68}$, CO(O)R$^{68}$, OC(O)R$^{68}$, OC(O)OR$^{68}$, NH$_2$, NHR$^{68}$, N(R$^{68}$)$_2$, NHC(O)R$^{68}$, NR$^{68}$C(O)R$^{68}$, NHS(O)$_2$R$^{68}$, NR$^{68}$S(O)$_2$R$^{68}$, NHC(O)OR$^{68}$, NR$^{68}$C(O)OR$^{68}$, NHC(O)NH$_2$, NHC(O)NHR$^{68}$, NHC(O)N(R$^{68}$)$_2$, NR$^{68}$C(O)NHR$^{68}$, NR$^{68}$C(O)N(R$^{68}$)$_2$, C(O)NH$_2$, C(O)NHR$^{68}$, C(O)N(R$^{68}$)$_2$, C(O)NHOH, C(O)NHOR$^{68}$, C(O)NHSO$_2$R$^{68}$, C(O)NR$^{68}$SO$_2$R$^{68}$, SO$_2$NH$_2$, SO$_2$NHR$^{68}$, SO$_2$N(R$^{68}$)$_2$, C(O)H, C(O)OH, C(N)NH$_2$, C(N)NHR$^{68}$, C(N)N(R$^{68}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{68}$ is R$^{69}$, R$^{70}$, R$^{71}$ or R$^{72}$;

R$^{69}$ is phenyl, which is unfused or fused with benzene, heteroarene or R$^{69A}$; R$^{69A}$ is cycloalkane, cycloalkene, heterocycloalkane or heterocycloalkene;

R$^{70}$ is heteroaryl, which is unfused or fused with benzene, heteroarene or R$^{70A}$; R$^{70A}$ is cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with benzene, heteroarene or R$^{71A}$; R$^{71A}$ is cycloalkane, cycloalkene, heterocycloalkane or heterocycloalkene;

R$^{72}$ is alkyl, alkenyl, or alkenyl, each of which is unsubstituted or substituted with one or two or three independently selected R$^{73}$, OR$^{73}$, SR$^{73}$, S(O)R$^{73}$, SO$_2$R$^{73}$, C(O)R$^{73}$, CO(O)R$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

$R^{73}$ is alkyl, alkenyl, alkenyl, phenyl, heteroaryl, cycloalkyl, cycloalkenyl, heterocycloalkyl, or heterocycloalkenyl; and the moieties represented by $R^{69}$, $R^{70}$, and $R^{71}$ are unsubstituted or substituted with one or more independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, $(O)$, $CN$, $N_3$, $NO_2$, $CF_3$, $CF_2CF_3$, $OCF_3$, $OCF_2CF_3$, F, Cl, Br or I substituents.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula V,

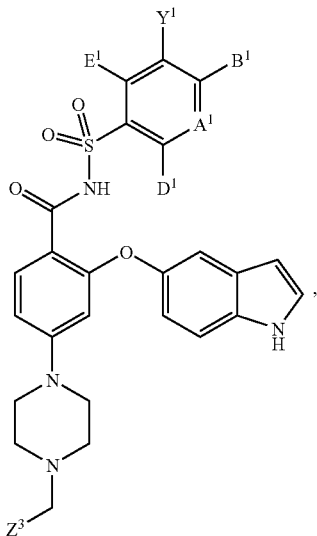

(V)

wherein $A^1$ is N or $C(A^2)$;

$A^2$, $B^1$, $D^1$, $E^1$, and $Y^1$ are independently selected H, OH, F, Cl, Br, I, CN, $CF_3$, $C(O)OH$, $C(O)NH_2$, $C(O)OR^{1A}$, $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

or $E^1$ and $Y^1$, together with the atoms to which they are attached, are benzene, naphthylene, heteroarene, cycloalkane, cycloalkene, heterocycloalkane or heterocycloalkene; and $A^2$, $B^1$, and $D^1$ are independently selected H, OH, F, Cl, Br, I, CN, $CF_3$, $C(O)OH$, $C(O)NH_2$, $C(O)OR^{1A}$, $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

or $Y^1$ and $B^1$, together with the atoms to which they are attached, are benzene, naphthylene, heteroarene, cycloalkane, cycloalkene, heterocycloalkane or heterocycloalkene; and $A^2$, $D^1$, and $E^1$ are independently selected H, OH, F, Cl, Br, I, CN, $CF_3$, $C(O)OH$, $C(O)NH_2$, $C(O)OR^{1A}$, $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

or $A^2$ and $B^1$, together with the atoms to which they are attached, are benzene, naphthylene, heteroarene, cycloalkane, cycloalkene, heterocycloalkane or heterocycloalkene; and $D^1$, $E^1$, and $Y^1$ are independently selected H, OH, F, Cl, Br, I, CN, $CF_3$, $C(O)OH$, $C(O)NH_2$, $C(O)OR^{1A}$, $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

or $A^2$ and $D^1$, together with the atoms to which they are attached, are benzene, naphthalene, heteroarene, cycloalkane, cycloalkene, heterocycloalkane or heterocycloalkene; and $B^1$, $E^1$, and $Y^1$ are independently selected H, OH, F, Cl, Br, I, CN, $CF_3$, $C(O)OH$, $C(O)NH_2$, $C(O)OR^{1A}$, $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with benzene, heteroarene or $R^{2A}$; $R^{2A}$ is cycloalkane, cycloalkene, heterocycloalkane or heterocycloalkene;

$R^3$ is heteroaryl, which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, $OH$, $(O)$, $C(O)OH$, $(O)$, $N_3$, $CN$, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, $C(O)$, $CNOH$, $CNOCH_3$, S, $S(O)$, $SO_2$ or NH;

$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$Z^3$ is $R^{38}$, $R^{39}$ or $R^{40}$;

$R^{38}$ is phenyl, which is unfused or fused with benzene, heteroarene or $R^{38A}$; $R^{38A}$ is cycloalkane, cycloalkene, heterocycloalkane or heterocycloalkene;

$R^{39}$ is heteroaryl, which is unfused or fused with benzene, heteroarene or $R^{39A}$; $R^{39A}$ is cycloalkane, cycloalkene, heterocycloalkane or heterocycloalkene;

$R^{40}$ is cycloalkyl, cycloalkenyl, heterocycloalkyl, or heterocycloalkenyl, each of which is unfused or fused with benzene, heteroarene or $R^{40A}$; $R^{40A}$ is cycloalkane, cycloalkene, heterocycloalkane or heterocycloalkene;

wherein the cyclic moieties represented by $E^1$ and $Y^1$ together, $Y^1$ and $B^1$ together, $A^2$ and $B^1$ together, $A^2$ and $D^1$ together, $R^{1A}$, $R^2$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{28}$, $R^{28A}$, $R^{29}$, $R^{29A}$, $R^{30}$, $R^{30A}$, $R^{37B}$, $R^{38}$, $R^{38A}$, $R^{39}$, $R^{39A}$, $R^{40}$, and $R^{40A}$ are independently unsubstituted, further unsubstituted, substituted or further substituted with one or more independently selected $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl, or alkynyl, each of which is unsubstituted or substituted with one or two or three independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl, or alkenyl, each of which is unsubstituted or substituted with one or two or three independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the cyclic moieties represented by $R^{58}$, $R^{59}$, $R^{60}$, $R^{63}$, $R^{64}$, $R^{65}$, and $R^{67}$ are unsubstituted or substituted with one or more independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R_{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{68}$ is $R^{69}$, $R^{70}$, $R^{71}$ or $R^{72}$;

$R^{69}$ is phenyl, which is unfused or fused with benzene, heteroarene or $R^{69A}$; $R^{69A}$ is cycloalkane, cycloalkene, heterocycloalkane or heterocycloalkene;

$R^{70}$ is heteroaryl, which is unfused or fused with benzene, heteroarene or $R^{70A}$; $R^{70A}$ is cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with benzene, heteroarene or $R^{71A}$; $R^{71A}$ is cycloalkane, cycloalkene, heterocycloalkane or heterocycloalkene;

$R^{72}$ is alkyl, alkenyl, or alkenyl, each of which is unsubstituted or substituted with one or two or three independently selected $R^{73}$, $OR^{73}$, $SR^{73}$, $S(O)R^{73}$, $SO_2R^{73}$, $C(O)R^{73}$, CO(O)R$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{73}$ is alkyl, alkenyl, alkenyl, phenyl, heteroaryl, cycloalkyl, cycloalkenyl, heterocycloalkyl, or heterocycloalkenyl; and the moieties represented by R$^{69}$, R$^{70}$, and R$^{71}$ are unsubstituted or substituted with one or more independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I substituents.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula VI,

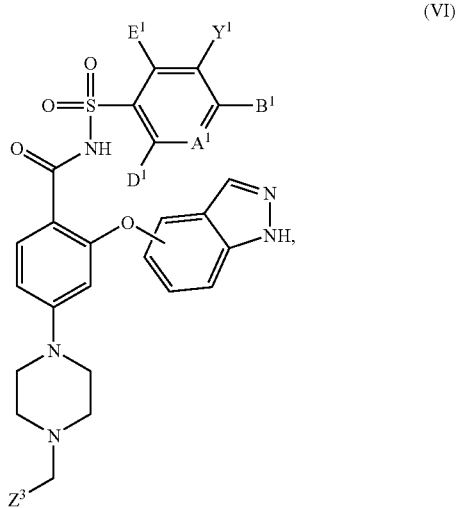

(VI)

wherein,

A$^1$ is N or C(A$^2$);

A$^2$, B$^1$, D$^1$, E$^1$, and Y$^1$ are independently selected H, OH, F, Cl, Br, I, CN, CF$_3$, C(O)OH, C(O)NH$_2$, C(O)OR$^{1A}$; NO$_2$, OCF$_3$, CF$_2$CF$_3$, OCF$_2$CF$_3$, NH$_2$, C(O)NH$_2$, NR$^1$C(O)R$^1$, NR$^1$S(O)$_2$R$^1$, NR$^1$C(O)OR$^1$, NHC(O)NH$_2$, NHC(O)NHR$^1$, NHC(O)N(R$^1$)$_2$, C(O)NHOH, C(O)NHOR$^1$, C(O)NHSO$_2$R$^1$, SO$_2$NH$_2$, C(O)H, C(N)NH$_2$, C(N)NHR$^1$, C(N)N(R$^1$)$_2$, CNOH, CNOCH$_3$, N$_3$, or NHS(O)R$^1$;

or

E$^1$ and Y$^1$, together with the atoms to which they are attached, are benzene, naphthylene, heteroarene, cycloalkane, cycloalkene, heterocycloalkane or heterocycloalkene; and A$^2$, B$^1$, and D$^1$ are independently selected H, OH, F, Cl, Br, I, CN, CF$_3$, C(O)OH, C(O)NH$_2$, C(O)OR$^{1A}$, NO$_2$, OCF$_3$, CF$_2$CF$_3$, OCF$_2$CF$_3$, NH$_2$, C(O)NH$_2$, NR$^1$C(O)R$^1$, NR$^1$S(O)$_2$R$^1$, NR$^1$C(O)OR$^1$, NHC(O)NH$_2$, NHC(O)NHR$^1$, NHC(O)N(R$^1$)$_2$, C(O)NHOH, C(O)NHOR$^1$, C(O)NHSO$_2$R$^1$, SO$_2$NH$_2$, C(O)H, C(N)NH$_2$, C(N)NHR$^1$, C(N)N(R$^1$)$_2$, CNOH, CNOCH$_3$, N$_3$, or NHS(O)R$^1$;

or

Y$^1$ and B$^1$, together with the atoms to which they are attached, are benzene, naphthylene, heteroarene, cycloalkane, cycloalkene, heterocycloalkane or heterocycloalkene; and A$^2$, D$^1$, and E$^1$ are independently selected H, OH, F, Cl, Br, I, CN, CF$_3$, C(O)OH, C(O)NH$_2$, C(O)OR$^{1A}$, NO$_2$, OCF$_3$, CF$_2$CF$_3$, OCF$_2$CF$_3$, NH$_2$, C(O)NH$_2$, NR$^1$C(O)R$^1$, NR$^1$S(O)$_2$R$^1$, NR$^1$C(O)OR$^1$, NHC(O)NH$_2$, NHC(O)NHR$^1$, NHC(O)N(R$^1$)$_2$, C(O)NHOH, C(O)NHOR$^1$, C(O)NHSO$_2$R$^1$, SO$_2$NH$_2$, C(O)H, C(N)NH$_2$, C(N)NHR$^1$, C(N)N(R$^1$)$_2$, CNOH, CNOCH$_3$, N$_3$, or NHS(O)R$^1$;

or

A$^2$ and B$^1$, together with the atoms to which they are attached, are benzene, naphthylene, heteroarene, cycloalkane, cycloalkene, heterocycloalkane or heterocycloalkene; and D$^1$, E$^1$, and Y$^1$ are independently selected H, OH, F, Cl, Br, I, CN, CF$_3$, C(O)OH, C(O)NH$_2$, C(O)OR$^{1A}$, NO$_2$, OCF$_3$, CF$_2$CF$_3$, OCF$_2$CF$_3$, NH$_2$, C(O)NH$_2$, NR$^1$C(O)R$^1$, NR$^1$S(O)$_2$R$^1$, NR$^1$C(O)OR$^1$, NHC(O)NH$_2$, NHC(O)NHR$^1$, NHC(O)N(R$^1$)$_2$, C(O)NHOH, C(O)NHOR$^1$, C(O)NHSO$_2$R$^1$, SO$_2$NH$_2$, C(O)H, C(N)NH$_2$, C(N)NHR$^1$, C(N)N(R$^1$)$_2$, CNOH, CNOCH$_3$, N$_3$, or NHS(O)R$^1$;

or

A$^2$ and D$^1$, together with the atoms to which they are attached, are benzene, naphthalene, heteroarene, cycloalkane, cycloalkene, heterocycloalkane or heterocycloalkene; and B$^1$, E$^1$, and Y$^1$ are independently selected H, OH, F, Cl, Br, I, CN, CF$_3$, C(O)OH, C(O)NH$_2$, C(O)OR$^{1A}$, NO$_2$, OCF$_3$, CF$_2$CF$_3$, OCF$_2$CF$_3$, NH$_2$, C(O)NH$_2$, NR$^1$C(O)R$^1$, NR$^1$S(O)$_2$R$^1$, NR$^1$C(O)OR$^1$, NHC(O)NH$_2$, NHC(O)NHR$^1$, NHC(O)N(R$^1$)$_2$, C(O)NHOH, C(O)NHOR$^1$, C(O)NHSO$_2$R$^1$, SO$_2$NH$_2$, C(O)H, C(N)NH$_2$, C(N)NHR$^1$, C(N)N(R$^1$)$_2$, CNOH, CNOCH$_3$, N$_3$, or NHS(O)R$^1$;

R$^1$ is R$^2$, R$^3$, R$^4$ or R$^5$;

R$^{1A}$ is cycloalkyl, cycloalkenyl or cycloalkynyl;

R$^2$ is phenyl, which is unfused or fused with benzene, heteroarene or R$^{2A}$; R$^{2A}$ is cycloalkane, cycloalkene, heterocycloalkane or heterocycloalkene;

R$^3$ is heteroaryl, which is unfused or fused with benzene, heteroarene or R$^{3A}$; R$^{3A}$ is cycloalkane, cycloalkene, heterocycloalkane or heterocycloalkene;

R$^4$ is cycloalkyl, cycloalkenyl, heterocycloalkyl or heterocycloalkenyl, each of which is unfused or fused with benzene, heteroarene or R$^{4A}$; R$^{4A}$ is cycloalkane, cycloalkene, heterocycloalkane or heterocycloalkene;

R$^5$ is alkyl, alkenyl or alkynyl, each of which is unsubstituted or substituted with one or two or three independently selected R$^6$, NC(R$^{6A}$)(R$^{6B}$), R$^7$, OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, C(O)N(R$^7$)$_2$, NHC(O)R$^7$, NR$^7$C(O)R$^7$, NHSO$_2$R$^7$, NHC(O)OR$^7$, SO$_2$NH$_2$, SO$_2$NHR$^7$, SO$_2$N(R$^7$)$_2$, NHC(O)NH$_2$, NHC(O)NHR$^7$, NHC(O)CH(CH$_3$)NHC(O)CH(CH$_3$)NH$_2$, NHC(O)CH(CH$_3$)NHC(O)CH(CH$_3$)NHR$^1$, OH, (O), C(O)OH, (O), N$_3$, CN, NH$_2$, CF$_3$, CF$_2$CF$_3$, F, Cl, Br or I substituents;

R$^6$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^{6A}$ and R$^{6B}$ are independently selected alkyl or, together with the N to which they are attached, R$^{6C}$;

R$^{6C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

R$^7$ is R$^8$, R$^9$, R$^{10}$ or R$^{11}$;

R⁸ is phenyl, which is unfused or fused with benzene, heteroarene or $R^{8A}$; $R^{8A}$ is cycloalkane, cycloalkene, heterocycloalkane or heterocycloalkene;

R⁹ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$Z^3$ is $R^{38}$, $R^{39}$ or $R^{40}$;

$R^{38}$ is phenyl, which is unfused or fused with benzene, heteroarene or $R^{38A}$; $R^{38A}$ is cycloalkane, cycloalkene, heterocycloalkane or heterocycloalkene;

$R^{39}$ is heteroaryl, which is unfused or fused with benzene, heteroarene or $R^{39A}$; $R^{39A}$ is cycloalkane, cycloalkene, heterocycloalkane or heterocycloalkene;

$R^{40}$ is cycloalkyl, cycloalkenyl, heterocycloalkyl, or heterocycloalkenyl, each of which is unfused or fused with benzene, heteroarene or $R^{40A}$; $R^{40A}$ is cycloalkane, cycloalkene, heterocycloalkane or heterocycloalkene;

wherein the cyclic moieties represented by $E^1$ and $Y^1$ together, $Y^1$ and $B^1$ together, $A^2$ and $B^1$ together, $A^2$ and $D^1$ together, $R^{1A}$, $R^2$, $R^{2A}$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{28}$, $R^{28A}$, $R^{29}$, $R^{29A}$, $R^{30}$, $R^{30A}$, $R^{37B}$, $R^{38A}$, $R^{39}$, $R^{39A}$, $R^{40}$, and $R^{40A}$ are independently unsubstituted, further unsubstituted, substituted or further substituted with one or more independently selected $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl, or alkynyl, each of which is unsubstituted or substituted with one or two or three independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl, or alkenyl, each of which is unsubstituted or substituted with one or two or three independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR_{67}$, $SO_2N(R^{67})_2$, $C(O)H$, $C(O)OH$, $C(N)NH_2$, $C(N)NHR^{67}$, $C(N)N(R^{67})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the cyclic moieties represented by $R^{58}$, $R^{59}$, $R^{60}$, $R^{63}$, $R^{64}$, $R^{65}$, and $R^{67}$ are unsubstituted or substituted with one or more independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R_{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{68}$ is $R^{69}$, $R^{70}$, $R^{71}$ or $R^{72}$;

$R^{69}$ is phenyl, which is unfused or fused with benzene, heteroarene or $R^{69A}$; $R^{69A}$ is cycloalkane, cycloalkene, heterocycloalkane or heterocycloalkene;

$R^{70}$ is heteroaryl, which is unfused or fused with benzene, heteroarene or $R^{74}$; $R^{74}$ is cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with benzene, heteroarene or $R^{71A}$; $R^{71A}$ is cycloalkane, cycloalkene, heterocycloalkane or heterocycloalkene;

$R^{72}$ is alkyl, alkenyl, or alkenyl, each of which is unsubstituted or substituted with one or two or three independently selected $R^{73}$, $OR^{73}$, $SR^{73}$, $S(O)R^{73}$, $SO_2R^{73}$, $C(O)R^{73}$, $CO(O)R^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

$R^{73}$ is alkyl, alkenyl, alkenyl, phenyl, heteroaryl, cycloalkyl, cycloalkenyl, heterocycloalkyl, or heterocycloalkenyl; and the moieties represented by $R^{69}$, $R^{70}$, and $R^{71}$ are unsubstituted or substituted with one or more independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I substituents.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula VII,

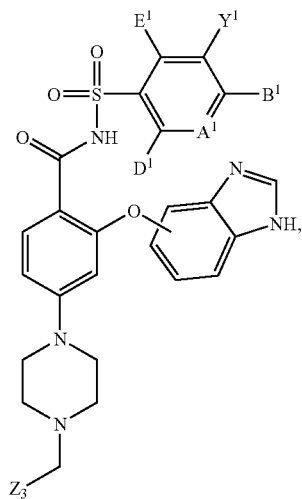

(VII)

wherein, $A^1$ is N or C($A^2$);

$A^2$, $B^1$, $D^1$, $E^1$, and $Y^1$ are independently selected H, OH, F, Cl, Br, I, CN, CF$_3$, C(O)OH, C(O)NH$_2$, C(O)OR$^{1A}$; NO$_2$, OCF$_3$, CF$_2$CF$_3$, OCF$_2$CF$_3$, NH$_2$, C(O)NH$_2$, NR$^1$C(O)R$^1$, NR$^1$S(O)$_2$R$^1$, NR$^1$C(O)OR$^1$, NHC(O)NH$_2$, NHC(O)NHR$^1$, NHC(O)N(R$^1$)$_2$, C(O)NHOH, C(O)NHOR$^1$, C(O)NHSO$_2$R$^1$, SO$_2$NH$_2$, C(O)H, C(N)NH$_2$, C(N)NHR$^1$, C(N)N(R$^1$)$_2$, CNOH, CNOCH$_3$, N$_3$, or NHS(O)R$^1$;

or $E^1$ and $Y^1$, together with the atoms to which they are attached, are benzene, naphthylene, heteroarene, cycloalkane, cycloalkene, heterocycloalkane or heterocycloalkene; and $A^2$, $B^1$, and $D^1$ are independently selected H, OH, F, Cl, Br, I, CN, CF$_3$, C(O)OH, C(O)NH$_2$, C(O)OR$^{1A}$, NO$_2$, OCF$_3$, CF$_2$CF$_3$, OCF$_2$CF$_3$, NH$_2$, C(O)NH$_2$, NR$^1$C(O)R$^1$, NR$^1$S(O)$_2$R$^1$, NR$^1$C(O)OR$^1$, NHC(O)NH$_2$, NHC(O)NHR$^1$, NHC(O)N(R$^1$)$_2$, C(O)NHOH, C(O)NHOR$^1$, C(O)NHSO$_2$R$^1$, SO$_2$NH$_2$, C(O)H, C(N)NH$_2$, C(N)NHR$^1$, C(N)N(R$^1$)$_2$, CNOH, CNOCH$_3$, N$_3$, or NHS(O)R$^1$;

or $Y^1$ and $B^1$, together with the atoms to which they are attached, are benzene, naphthylene, heteroarene, cycloalkane, cycloalkene, heterocycloalkane or heterocycloalkene; and $A^2$, $D^1$, and $E^1$ are independently selected H, OH, F, Cl, Br, I, CN, CF$_3$, C(O)OH, C(O)NH$_2$, C(O)OR$^{1A}$, NO$_2$, OCF$_3$, CF$_2$CF$_3$, OCF$_2$CF$_3$, NH$_2$, C(O)NH$_2$, NR$^1$C(O)R$^1$, NR$^1$S(O)$_2$R$^1$, NR$^1$C(O)OR$^1$, NHC(O)NH$_2$, NHC(O)NHR$^1$, NHC(O)N(R$^1$)$_2$, C(O)NHOH, C(O)NHOR$^1$, C(O)NHSO$_2$R$^1$, SO$_2$NH$_2$, C(O)H, C(N)NH$_2$, C(N)NHR$^1$, C(N)N(R$^1$)$_2$, CNOH, CNOCH$_3$, N$_3$, or NHS(O)R$^1$;

or $A^2$ and $B^1$, together with the atoms to which they are attached, are benzene, naphthylene, heteroarene, cycloalkane, cycloalkene, heterocycloalkane or heterocycloalkene; and $D^1$, $E^1$, and $Y^1$ are independently selected H, OH, F, Cl, Br, I, CN, CF$_3$, C(O)OH, C(O)NH$_2$, C(O)OR$^{1A}$, NO$_2$, OCF$_3$, CF$_2$CF$_3$, OCF$_2$CF$_3$, NH$_2$, C(O)NH$_2$, NR$^1$C(O)R$^1$, NR$^1$S(O)$_2$R$^1$, NR$^1$C(O)OR$^1$, NHC(O)NH$_2$, NHC(O)NHR$^1$, NHC(O)N(R$^1$)$_2$, C(O)NHOH, C(O)NHOR$^1$, C(O)NHSO$_2$R$^1$, SO$_2$NH$_2$, C(O)H, C(N)NH$_2$, C(N)NHR$^1$, C(N)N(R$^1$)$_2$, CNOH, CNOCH$_3$, N$_3$, or NHS(O)R$^1$;

or $A^2$ and $D^1$, together with the atoms to which they are attached, are benzene, naphthalene, heteroarene, cycloalkane, cycloalkene, heterocycloalkane or heterocycloalkene; and $B^1$, $E^1$, and $Y^1$ are independently selected H, OH, F, Cl, Br, I, CN, CF$_3$, C(O)OH, C(O)NH$_2$, C(O)OR$^{1A}$, NO$_2$, OCF$_3$, CF$_2$CF$_3$, OCF$_2$CF$_3$, NH$_2$, C(O)NH$_2$, NR$^1$C(O)R$^1$, NR$^1$S(O)$_2$R$^1$, NR$^1$C(O)OR$^1$, NHC(O)NH$_2$, NHC(O)NHR$^1$, NHC(O)N(R$^1$)$_2$, C(O)NHOH, C(O)NHOR$^1$, C(O)NHSO$_2$R$^1$, SO$_2$NH$_2$, C(O)H, C(N)NH$_2$, C(N)NHR$^1$, C(N)N(R$^1$)$_2$, CNOH, CNOCH$_3$, N$_3$, or NHS(O)R$^1$;

$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with benzene, heteroarene or $R^{2A}$; $R^{2A}$ is cycloalkane, cycloalkene, heterocycloalkane or heterocycloalkene;

$R^3$ is heteroaryl, which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, NC($R^{6A}$)($R^{6B}$), $R^7$, OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, C(O)N($R^7$)$_2$, NHC(O)$R^7$, $NR^7$C(O)$R^7$, NHSO$_2R^7$, NHC(O)O$R^7$, SO$_2$NH$_2$, SO$_2$NH$R^7$, SO$_2$N($R^7$)$_2$, NHC(O)NH$_2$, NHC(O)NH$R^7$, NHC(O)CH(CH$_3$)NHC(O)CH(CH$_3$)NH$_2$, NHC(O)CH(CH$_3$)NHC(O)CH(CH$_3$)NH$R^1$, OH, (O), C(O)OH, (O), N$_3$, CN, NH$_2$, CF$_3$, CF$_2$CF$_3$, F, Cl, Br or I substituents;

$R^6$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, O$R^{12}$, S$R^{12}$, S(O)$R^{12}$, SO$_2R^{12}$, C(O)$R^{12}$, CO(O)$R^{12}$, OC(O)$R^{12}$, OC(O)O$R^{12}$, NH$_2$, NH$R^{12}$, N($R^{12}$)$_2$, NHC(O)$R^{12}$, N$R^{12}$C(O)$R^{12}$, NHS(O)$_2R^{12}$, N$R^{12}$S(O)$_2R^{12}$, NHC(O)O$R^{12}$, N$R^{12}$C(O)O$R^{12}$, NHC(O)NH$_2$, NHC(O)NH$R^{12}$, NHC(O)N($R^{12}$)$_2$, N$R^{12}$C(O)NH$R^{12}$, N$R^{12}$C(O)N($R^{12}$)$_2$, C(O)NH$_2$, C(O)NH$R^{12}$, C(O)N($R^{12}$)$_2$, C(O)NHOH, C(O)NHO$R^{12}$, C(O)NHSO$_2R^{12}$, C(O)N$R^{12}$SO$_2R^{12}$, SO$_2$NH$_2$, SO$_2$NH$R^{12}$, SO$_2$N($R^{12}$)$_2$, C(O)H, C(O)OH, C(N)NH$_2$, C(N)NH$R^{12}$, C(N)N($R^{12}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$Z^3$ is $R^{38}$, $R^{39}$ or $R^{40}$;

$R^{38}$ is phenyl, which is unfused or fused with benzene, heteroarene or $R^{38A}$; $R^{38A}$ is cycloalkane, cycloalkene, heterocycloalkane or heterocycloalkene;

$R^{39}$ is heteroaryl, which is unfused or fused with benzene, heteroarene or $R^{39A}$; $R^{39A}$ is cycloalkane, cycloalkene, heterocycloalkane or heterocycloalkene;

$R^{40}$ is cycloalkyl, cycloalkenyl, heterocycloalkyl, or heterocycloalkenyl, each of which is unfused or fused with benzene, heteroarene or $R^{40A}$; $R^{40A}$ is cycloalkane, cycloalkene, heterocycloalkane or heterocycloalkene;

wherein the cyclic moieties represented by $E^1$ and $Y^1$ together, $Y^1$ and $B^1$ together, $A^2$ and $B^1$ together, $A^2$ and $D^1$ together, $R^{1A}$, $R^2$, $R^{2A}$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{28}$, $R^{28A}$, $R^{29}$, $R^{29A}$, $R^{30}$, $R^{30A}$, $R^{37B}$, $R^{38}$, $R^{38A}$, $R^{39}$, $R^{39A}$, $R^{40}$ and $R^{40A}$ are independently unsubstituted, further unsubstituted, substituted or further substituted with one or more independently selected $R^{57}$, O$R^{57}$, S$R^{57}$, S(O)$R^{57}$, SO$_2R^{57}$, C(O)$R^{57}$, CO(O)$R^{57}$, OC(O)$R^{57}$, OC(O)O$R^{57}$, NH$_2$, NH$R^{57}$, N($R^{57}$)$_2$, NHC(O)$R^{57}$, N$R^{57}$C(O)$R^{57}$, NHS(O)$_2R^{57}$, N$R^{57}$S(O)$_2R^{57}$, NHC(O)O$R^{57}$, N$R^{57}$C(O)O$R^{57}$, NHC(O)NH$_2$, NHC(O)NH$R^{57}$, NHC(O)N($R^{57}$)$_2$, N$R^{57}$C(O)NH$R^{57}$, N$R^{57}$C(O)N($R^{57}$)$_2$, C(O)NH$_2$, C(O)NH$R^{57}$, C(O)N($R^{57}$)$_2$, C(O)NHOH, C(O)NHO$R^{57}$, C(O)NHSO$_2R^{57}$, C(O)N$R^{57}$SO$_2R^{57}$, SO$_2$NH$_2$, SO$_2$NH$R^{57}$, SO$_2$N($R^{57}$)$_2$, C(O)H, C(O)OH, C(N)NH$_2$, C(N)NH$R^{57}$, C(N)N($R^{57}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl, or alkynyl, each of which is unsubstituted or substituted with one or two or three independently selected $R^{62}$, O$R^{62}$, S$R^{62}$, S(O)$R^{62}$, SO$_2R^{62}$, C(O)$R^{62}$, CO(O)$R^{62}$, OC(O)$R^{62}$, OC(O)O$R^{62}$, NH$_2$, NH$R^{62}$, N($R^{62}$)$_2$, NHC(O)$R^{62}$, N$R^{62}$C(O)$R^{62}$, NHS(O)$_2R^{62}$, N$R^{62}$S(O)$_2R^{62}$, NHC(O)O$R^{62}$, N$R^{62}$C(O)O$R^{62}$, NHC(O)NH$_2$, NHC(O)NH$R^{62}$, NHC(O)N($R^{62}$)$_2$, N$R^{62}$C(O)NH$R^{62}$, N$R^{62}$C(O)N($R^{62}$)$_2$, C(O)NH$_2$, C(O)NH$R^{62}$, C(O)N($R^{62}$)$_2$, C(O)NHOH, C(O)NHO$R^{62}$, C(O)NHSO$_2R^{62}$, C(O)N$R^{62}$SO$_2R^{62}$, SO$_2$NH$_2$, SO$_2$NH$R^{62}$, SO$_2$N($R^{62}$)$_2$, C(O)H, C(O)OH, C(N)NH$_2$, C(N)NH$R^{62}$, C(N)N($R^{62}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl, or alkenyl, each of which is unsubstituted or substituted with one or two or three independently selected $R^{67}$, O$R^{67}$, S$R^{67}$, S(O)$R^{67}$, SO$_2R^{67}$, C(O)$R^{67}$, CO(O)$R^{67}$, OC(O)$R^{67}$, OC(O)O$R^{67}$, NH$_2$, NH$R^{67}$, N($R^{67}$)$_2$, NHC(O)$R^{67}$, N$R^{67}$C(O)$R^{67}$, NHS(O)$_2R^{67}$, N$R^{67}$S(O)$_2R^{67}$, NHC(O)O$R^{67}$, N$R^{67}$C(O)O$R^{67}$, NHC(O)NH$_2$, NHC(O)NH$R^{67}$, NHC(O)N($R^{67}$)$_2$, N$R^{67}$C(O)NH$R^{67}$, N$R^{67}$C(O)N($R^{67}$)$_2$, C(O)NH$_2$, C(O)NH$R^{67}$, C(O)N($R^{67}$)$_2$, C(O)NHOH, C(O)NHO$R^{67}$, C(O)NHSO$_2R^{67}$, C(O)N$R^{67}$SO$_2R^{67}$, SO$_2$NH$_2$, SO$_2$NH$R^{67}$, SO$_2$N($R^{67}$)$_2$, C(O)H, C(O)OH, C(N)NH$_2$, C(N)NH$R^{67}$, C(N)N($R^{67}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the cyclic moieties represented by $R^{58}$, $R^{59}$, $R^{60}$, $R^{63}$, $R^{64}$, $R^{65}$, and $R^{67}$ are unsubstituted or substituted with one or more independently selected $R^{68}$, O$R^{68}$, S$R^{68}$, S(O)$R^{68}$, SO$_2R^{68}$, C(O)$R^{68}$, CO(O)$R^{68}$, OC(O)$R^{68}$, OC(O)O$R^{68}$, NH$_2$, NHR$^{68}$, N(R$^{68}$)$_2$, NHC(O)R$^{68}$, NR$^{68}$C(O)R$^{68}$, NHS(O)$_2$R$^{68}$, NR$^{68}$S(O)$_2$R$^{68}$, NHC(O)OR$^{68}$, NR$^{68}$C(O)OR$^{68}$, NHC(O)NH$_2$, NHC(O)NHR$^{68}$, NHC(O)N(R$^{68}$)$_2$, NR$^{68}$C(O)NHR$^{68}$, NR$^{68}$C(O)N(R$^{68}$)$_2$, C(O)NH$_2$, C(O)NHR$^{68}$, C(O)N(R$^{68}$)$_2$, C(O)NHOH, C(O)NHOR$^{68}$, C(O)NHSO$_2$R$^{68}$, C(O)NR$^{68}$SO$_2$R$^{68}$, SO$_2$NH$_2$, SO$_2$NHR$^{68}$, SO$_2$N(R$^{68}$)$_2$, C(O)H, C(O)OH, C(N)NH$_2$, C(N)NHR$^{68}$, C(N)N(R$^{68}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{68}$ is R$^{69}$; R$^{70}$; R$^{71}$ or R$^{72}$;

R$^{69}$ is phenyl, which is unfused or fused with benzene, heteroarene or R$^{69A}$; R$^{69A}$ is cycloalkane, cycloalkene, heterocycloalkane or heterocycloalkene;

R$^{70}$ is heteroaryl, which is unfused or fused with benzene, heteroarene or R$^{70A}$; R$^{70A}$ is cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with benzene, heteroarene or R$^{71A}$; R$^{71A}$ is cycloalkane, cycloalkene, heterocycloalkane or heterocycloalkene;

R$^{72}$ is alkyl, alkenyl, or alkenyl, each of which is unsubstituted or substituted with one or two or three independently selected R$^{73}$, OR$^{73}$, SR$^{73}$, S(O)R$^{73}$, SO$_2$R$^{73}$, C(O)R$^{73}$, CO(O)R$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{73}$ is alkyl, alkenyl, alkenyl, phenyl, heteroaryl, cycloalkyl, cycloalkenyl, heterocycloalkyl, or heterocycloalkenyl; and the moieties represented by R$^{69}$, R$^{70}$, and R$^{71}$ are unsubstituted or substituted with one or more independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I substituents.

Still another embodiment pertains to compounds having Formula I, which are

4-[4-(3,3-diphenylprop-2-enyl)piperazin-1-yl]-N-[(3-nitrophenyl)sulfonyl]benzamide;

N-[(2-bromophenyl)sulfonyl]-4-(4-{[2-(4-chlorophenyl)cyclohex-1-en-1-yl]methyl}piperazin-1-yl)benzamide;

N-[(3-bromophenyl)sulfonyl]-4-(4-{[2-(4-chlorophenyl)cyclohex-1-en-1-yl]methyl}piperazin-1-yl)benzamide;

N-[(4-bromophenyl)sulfonyl]-4-(4-{[2-(4-chlorophenyl)cyclohex-1-en-1-yl]methyl}piperazin-1-yl)benzamide;

4-{4-[(4'-chloro-1,1'-biphenyl-2-yl)methyl]piperazin-1-yl}-N-[(3-nitrophenyl)sulfonyl]benzamide;

4-{4-[(4'-chloro-1,1'-biphenyl-2-yl)methyl]piperazin-1-yl}-N-(phenylsulfonyl)benzamide;

2-(benzyloxy)-4-{4-[(4'-chloro-1,1'-biphenyl-2-yl)methyl]piperazin-1-yl}-N-[(3-nitrophenyl)sulfonyl]benzamide;

4-{4-[(4'-chloro-1,1'-biphenyl-2-yl)methyl]piperazin-1-yl}-N-[(3-nitrophenyl)sulfonyl]-2-(2-phenylethoxy)benzamide;

4-{4-[(4'-chloro-1,1'-biphenyl-2-yl)methyl]piperazin-1-yl}-N-[(3-nitrophenyl)sulfonyl]-2-phenoxybenzamide;

4-{4-[(4'-chloro-1,1'-biphenyl-2-yl)methyl]piperazin-1-yl}-2-phenoxy-N-(phenylsulfonyl)benzamide;

N-[(4-bromophenyl)sulfonyl]-4-{4-[(4'-chloro-1,1'-biphenyl-2-yl)methyl]piperazin-1-yl}benzamide;

4-[4-(1,1'-biphenyl-4-ylmethyl)-3-isopropylpiperazin-1-yl]-N-(phenylsulfonyl)benzamide;

4-{4-[(4'-chloro-1,1'-biphenyl-2-yl)methyl]piperazin-1-yl}-N-[(3-nitrophenyl)sulfonyl]-2-(phenylthio)benzamide;

2-(benzylamino)-4-{4-[(4'-chloro-1,1'-biphenyl-2-yl)methyl]piperazin-1-yl}-N-[(3-nitrophenyl)sulfonyl]benzamide;

2-benzyl-4-{4-[(4'-chloro-1,1'-biphenyl-2-yl)methyl]piperazin-1-yl}-N-[(3-nitrophenyl)sulfonyl]benzamide;

4-{4-[(4'-chloro-1,1'-biphenyl-2-yl)methyl]piperazin-1-yl}-N-[(4-nitrophenyl)sulfonyl]benzamide;

4-{4-[(4'-chloro-1,1'-biphenyl-2-yl)methyl]piperazin-1-yl}-N-[(4-hydroxyphenyl)sulfonyl]benzamide;

4-{4-[(4'-chloro-1,1'-biphenyl-2-yl)methyl]piperazin-1-yl}-N-[(3-nitrophenyl)sulfonyl]-2-(2-phenylethyl)benzamide;

4-{4-[(4'-chloro-1,1'-biphenyl-2-yl)methyl]piperazin-1-yl}-N-[(4-fluorophenyl)sulfonyl]benzamide;

4-{4-[(4'-chloro-1,1'-biphenyl-2-yl)methyl]piperazin-1-yl}-N-[(3-fluorophenyl)sulfonyl]benzamide;

4-{4-[(4'-chloro-1,1'-biphenyl-2-yl)methyl]piperazin-1-yl}-N-[(3-nitrophenyl)sulfonyl]-2-(phenylsulfinyl)benzamide;

4-{4-[(4'-chloro-1,1'-biphenyl-2-yl)methyl]piperazin-1-yl}-N-[(4-nitrophenyl)sulfonyl]-2-phenoxybenzamide;

4-{4-[(4'-chloro-1,1'-biphenyl-2-yl)methyl]piperazin-1-yl}-N-[(3-fluorophenyl)sulfonyl]-2-phenoxybenzamide;

4-{4-[(4'-chloro-1,1'-biphenyl-2-yl)methyl]piperazin-1-yl}-N-[(4-fluorophenyl)sulfonyl]-2-phenoxybenzamide;

4-{4-[(4'-chloro-1,1'-biphenyl-2-yl)methyl]piperazin-1-yl}-2-methoxy-N-[(3-nitrophenyl)sulfonyl]benzamide;

4-{4-[(4'-chloro-1,1'-biphenyl-2-yl)methyl]piperazin-1-yl}-N-[(3-nitrophenyl)sulfonyl]-2-(phenylsulfonyl)benzamide;

4-{4-[(4'-chloro-1,1'-biphenyl-2-yl)methyl]piperazin-1-yl}-N-[(4-chloro-3-nitrophenyl)sulfonyl]-2-phenoxybenzamide;

4-[4-({4'-chloro-3-[2-(dimethylamino)ethoxy]-1,1'-biphenyl-2-yl}methyl)piperazin-1-yl]-2-(1H-indol-4-yloxy)-N-[(3-nitrophenyl)sulfonyl]benzamide;

4-[4-({4'-chloro-3-[2-(dimethylamino)ethoxy]-1,1'-biphenyl-2-yl}methyl)piperazin-1-yl]-2-(1H-indol-4-yloxy)-N-(phenylsulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-(phenylsulfonyl)benzamide;

4-(4-{[2-(4-chlorophenyl)-4,4-dimethylcyclohex-1-en-1-yl]methyl}piperazin-1-yl)-N-[(3-cyanophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-(trifluoromethyl)phenyl]sulfonyl}benzamide;

4-(4-{[2-(4-chlorophenyl)-4,4-dimethylcyclohex-1-en-1-yl]methyl}piperazin-1-yl)-N-[(3-chlorophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-[(3-fluorophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-(2-naphthylsulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-(isoquinolin-5-ylsulfonyl)benzamide;

N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

4-{4-[(4'-chlorobiphenyl-2-yl)methyl]piperazin-1-yl}-N-[(2-chloropyridin-3-yl)sulfonyl]benzamide;

4-{4-[(4'-chlorobiphenyl-2-yl)methyl]piperazin-1-yl}-N-[(7-nitro-1H-benzimidazol-5-yl)sulfonyl]benzamide;

4-{4-[(4'-chlorobiphenyl-2-yl)methyl]piperazin-1-yl}-N-[(3-oxo-3,4-dihydro-2H-1,4-benzoxazin-6-yl)sulfonyl]benzamide;

4-{4-[(4'-chlorobiphenyl-2-yl)methyl]piperazin-1-yl}-N-[(6-chloro-1,1-dioxido-2H-1,2,4-benzothiadiazin-7-yl)sulfonyl]benzamide;

4-{4-[(4'-chlorobiphenyl-2-yl)methyl]piperazin-1-yl}-N-({5-[ethyl(trifluoroacetyl)amino]-1-naphthyl}sulfonyl)benzamide;

4-{4-[(4'-chlorobiphenyl-2-yl)methyl]piperazin-1-yl}-N-[(5,5,8,8-tetramethyl-5,6,7,8-tetrahydronaphthalen-2-yl)sulfonyl]benzamide;

4-{4-[(4'-chlorobiphenyl-2-yl)methyl]piperazin-1-yl}-N-[(2-oxo-2H-chromen-6-yl)sulfonyl]benzamide;

and therapeutically acceptable salts, prodrugs, salts of prodrugs and metabolites thereof.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of the compound of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient a therapeutically effective amount of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient therapeutically effective amount of the compound of Formula (I) and a therapeutically effective amount of one additional therapeutic agent or more than one additional therapeutic agent.

DETAILED DESCRIPTION OF THE INVENTION

Variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "alkenyl" as used herein, means a straight or branched hydrocarbon chain containing from 2 to 10 carbons and containing at least one carbon-carbon double bond. The term "$C_x$-$C_y$ alkyl" means a straight or branched hydrocarbon chain containing at least one carbon-carbon double bond containing x to y carbon atoms. The term "$C_2$-$C_4$ alkenyl" means an alkenyl group containing 2-4 carbon atoms. Representative examples of alkenyl include, but are not limited to buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. The term "$C_x$-$C_y$ alkylene" means a a divalent group derived from a straight or branched hydrocarbon chain containing at least one carbon-carbon double bond and containing x to y carbon atoms. Representative examples of alkenylene include, but are not limited to, —CH═CH— and —CH$_2$CH═CH—.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_2$-$C_{10}$ alkyl" means a straight or branched chain, saturated hydrocarbon containing 2 to 10 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 4 carbon atoms. The term "$C_x$-$C_y$ alkylene" means a divalent group derived from a straight or branched chain, saturated hydrocarbon containing x to y carbon atoms. For example "$C_2$-$C_6$ alkylene" means a straight or branched chain, saturated hydrocarbon containing 2 to 6 carbon atoms. Examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_x$-$C_y$ alkynyl" means a straight or branched chain hydrocarbon group containing from x to y carbon atoms. Representative examples of alkynyl include, but are not limited, to acetylenyl, 1-propynyl, 2-propynyl, 3-butynyl, 2-pentynyl, and 1-butynyl.

The term "alkynylene," as used herein, means a divalent radical derived from a straight or branched chain hydrocarbon group containing from 2 to 10 carbon atoms and containing at least one carbon-carbon triple bond.

The term "aryl" as used herein, means phenyl.

The term "cyclic moiety," as used herein, means benzene, phenyl, phenylene, cycloalkane, cycloalkyl, cycloalkylene, cycloalkene, cycloalkenyl, cycloalkenylene, cycloalkyne, cycloalkynyl, cycloalkynylene, heteroarene, heteroaryl, heterocycloalkane, heterocycloalkyl, heterocycloalkene, heterocycloalkenyl, spiroheteroalkyl, spiroheteroalkenyl, spirocyclo, and spiroalkyl.

The term "cycloalkylene" or cycloalkyl" or "cycloalkane" as used herein, means a monocyclic or bridged hydrocarbon ring system. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and bridged cycloalkyl can be attached to the parent molecular moiety through any substitutable atom contained within the ring system.

The term "cycloalkenylene," or "cycloalkenyl" or "cycloalkene" as used herein, means a monocyclic or a bridged hydrocarbon ring system. The monocyclic cycloalkenyl has four-, five-, six-, seven- or eight carbon atoms and zero heteroatoms. The four-membered ring systems have one double bond, the five-or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl ring may contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems.

The term "cycloalkyne," or "cycloalkynyl," or "cycloalkynylene," as used herein, means a monocyclic or a bridged hydrocarbon ring system. The monocyclic cycloalkynyl has eight or more carbon atoms, zero heteroatoms, and one or more triple bonds. The monocyclic cycloalkynyl ring may contain one or two alkylene bridges, each consisting of one, two, or three carbon atoms, each linking two non-adjacent carbon atoms of the ring system. The monocyclic and bridged cycloalkynyl can be attached to the parent molecular moiety through any substitutable atom contained within the ring systems.

The term "heteroarene," or "heteroaryl" or "heteroarylene," as used herein, means a five-membered or six-membered aromatic ring having at least one carbon atom and one or more than one independently selected nitrogen, oxygen or sulfur atom. The heteroarenes of this invention are connected through any adjacent atoms in the ring, provided that proper valences are maintained. Representative examples of heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, thiazolyl, thienyl (including, but not limited thereto, thien-2-yl, thien-3-yl), triazolyl, and triazinyl.

The term "heterocycloalkane," or "heterocycloalkyl," or "heterocycloalkylene," as used herein, means monocyclic or bridged three-, four-, five-, six-, seven-, or eight-membered ring containing at least one heteroatom independently selected from the group consisting of O, N, and S and zero double bonds. The monocyclic and bridged heterocycloalkane are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkane groups include, but are not limited to, Representative examples of heterocycloalkane groups include, but are not limited to, morpholinyl, tetrahydropyranyl, pyrrolidinyl, piperidinyl, dioxolanyl, tetrahydrofuranyl, thiomorpholinyl, dioxanyl, tetrahydrothienyl, tetrahydrothiopyranyl, oxetanyl, piperazinyl, imidazolidinyl, azetidine, azepanyl, aziridinyl, diazepanyl, dithiolanyl, dithianyl, isoxazolidinyl, isothiazolidinyl, oxadiazolidinyl, oxazolidinyl, pyrazolidinyl, tetrahydrothienyl, thiadiazolidinyl, thiazolidinyl, thiomorpholinyl, trithianyl, and trithianyl.

The term "heterocycloalkene," or "heterocycloalkenyl," or "heterocycloalkenylene," as used herein, means monocyclic or bridged three-, four-, five-, six-, seven-, or eight-membered ring containing at least one heteroatom independently selected from the group consisting of O, N, and S and one or more double bonds. The monocyclic and bridged heterocycloalkene are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkene groups include, but are not limited to, tetrahydrooxocinyl, 1,4,5,6-tetrahydropyridazinyl, 1,2,3,6-tetrahydropyridinyl, dihydropyranyl, imidazolinyl, isothiazolinyl, oxadiazolinyl, isoxazolinyl, oxazolinyl, pyranyl, pyrazolinyl, pyrrolinyl, thiadiazolinyl, thiazolinyl, and thiopyranyl.

The term "phenylene," as used herein, means a divalent radical formed by removal of a hydrogen atom from phenyl.

The term "spiroalkyl," as used herein, means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like.

The term "spiroheteroalkyl," as used herein, means spiroalkyl having one or two $CH_2$ moieties replaced with independently selected O, C(O), CNOH, CNOCH$_3$, S, S(O), SO$_2$ or NH and one or two CH moieties unreplaced or replaced with N.

The term "spiroheteroalkenyl," as used herein, means spiroalkenyl having one or two $CH_2$ moieties replaced with independently selected O, C(O), CNOH, CNOCH$_3$, S, S(O), SO$_2$ or NH and one or two CH moieties unreplaced or replaced with N and also means spiroalkenyl having one or two $CH_2$ moieties unreplaced or replaced with independently selected O, C(O), CNOH, CNOCH$_3$, S, S(O), SO$_2$ or NH and one or two CH moieties replaced with N.

The term, "spirocyclo," as used herein, means two substituents on the same carbon atom, that, together with the carbon atom to which they are attached, form a cycloalkane, heterocycloalkane, cycloalkene, or heterocycloalkene ring.

The term "$C_2$-$C_5$-spiroalkyl," as used herein, means $C_2$-spiroalkyl, $C_3$-spiroalkyl, $C_4$-spiroalkyl, and $C_5$-spiroalkyl.

The term "$C_2$-spiroalkyl," as used herein, means eth-1,2-ylene, both ends of which replace hydrogen atoms of the same $CH_2$ moiety.

The term "$C_3$-spiroalkyl," as used herein, means prop-1,3-ylene, both ends of which replace hydrogen atoms of the same $CH_2$ moiety.

The term "$C_4$-spiroalkyl," as used herein, means but-1,4-ylene, both ends of which replace hydrogen atoms of the same $CH_2$ moiety.

The term "$C_5$-spiroalkyl," as used herein, means pent-1,5-ylene, both ends of which replace hydrogen atoms of the same $CH_2$ moiety.

The term "$C_6$-spiroalkyl," as used herein, means hex-1,6-ylene, both ends of which replace hydrogen atoms of the same $CH_2$ moiety.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble *J. Org. Chem.* 1998, 63, 2758-2760 and E. L. Eliel, and S. H. Wilen. (1994) *Stereochemistry of Organic Compounds*. New York, N.Y.: John Wiley & Sons, Inc.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of this invention containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521, 421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp.125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-istopic compound.

Amides, Esters and Prodrugs

Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hemi-aminals, polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

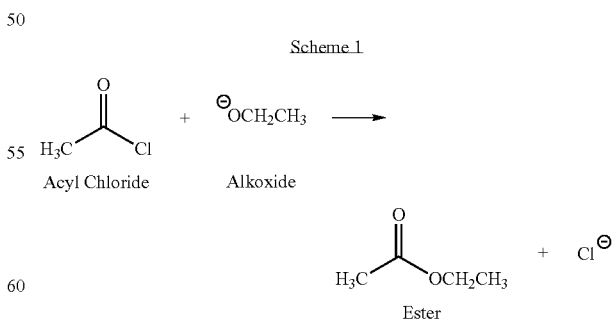

Scheme 1

Amides can be prepared from substrates of formula (I) containing either an amino group or a carboxy group in similar fashion. Esters can also react with amines or ammonia to form amides.

Scheme 2

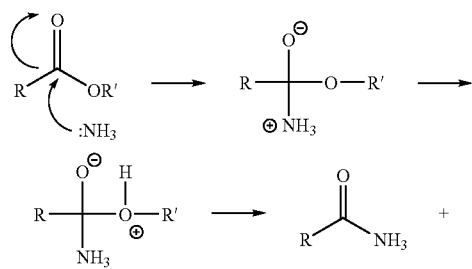

Another way to make amides from compounds of formula (I) is to heat carboxylic acids and amines together.

Scheme 3

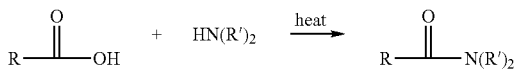

In Schemes 2 and 3 above, R and R' are independently substrates of formula (I), alkyl or hydrogen.

Suitable groups for $A^1$, $B^1$, $D^1$, $E^1$, $Y^1$, $L^1$, $Z^{1A}$, $Z^{2A}$, $Z^1$, $Z^2$, and $Z^3$ in compounds of Formula (I) are independently selected. The described embodiments of the present invention may be combined. Such combination is contemplated and within the scope of the present invention. For example, it is contemplated that embodiments for any of $A^1$, $B^1$, $D^1$, $E^1$, $Y^1$, $L^1$, $Z^{1A}$, $Z^{2A}$, $Z^1$, $Z^2$, and $Z^3$ can be combined with embodiments defined for any other of $A^1$, $B^1$, $D^1$, $E^1$, $Y^1$, $L^1$, $Z^{1A}$, $Z^{2A}$, $Z^1$, $Z^2$, and $Z^3$.

One embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (I)

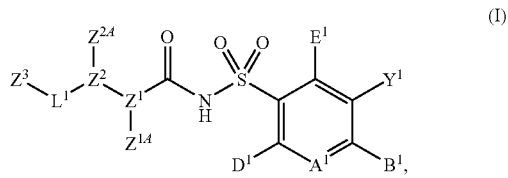

wherein $A^1$ is N or $C(A^2)$;

$A^2$, $B^1$, $D^1$, $E^1$, and $Y^1$ are independently selected H, OH, F, Cl, Br, I, CN, $CF_3$, C(O)OH, C(O)$NH_2$, C(O)$OR^{1A}$; $NO_2$, $OCF_3$, $CF_2CF_3$, $OCF_2CF_3$, $NH_2$, C(O)$NH_2$, $NR^1C(O)R^1$, $NR^1S(O)_2R^1$, $NR^1C(O)OR^1$, NHC(O)$NH_2$, NHC(O)$NHR^1$, NHC(O)N($R^1$)$_2$, C(O)NHOH, C(O)$NHOR^1$, C(O)$NHSO_2R^1$, $SO_2NH_2$, C(O)H, C(N)$NH_2$, C(N)$NHR^1$, C(N)N($R^1$)$_2$, CNOH, $CNOCH_3$, $N_3$, or $NHS(O)R^1$;

or $E^1$ and $Y^1$, together with the atoms to which they are attached, are benzene, naphthylene, heteroarene, cycloalkane, cycloalkene, heterocycloalkane or heterocycloalkene; and $A^2$, $B^1$, and $D^1$ are independently selected H, OH, F, Cl, Br, I, CN, $CF_3$, C(O)OH, C(O)$NH_2$, C(O)$OR^{1A}$, $NO_2$, $OCF_3$, $CF_2CF_3$, $OCF_2CF_3$, $NH_2$, C(O)$NH_2$, $NR^1C(O)R^1$, $NR^1S(O)_2R^1$, $NR^1C(O)OR^1$, NHC(O)$NH_2$, NHC(O)$NHR^1$, NHC(O)N($R^1$)$_2$, C(O)NHOH, C(O)$NHOR^1$, C(O)$NHSO_2R^1$, $SO_2NH_2$, C(O)H, C(N)$NH_2$, C(N)$NHR^1$, C(N)N($R^1$)$_2$, CNOH, $CNOCH_3$, $N_3$, or $NHS(O)R^1$;

or $Y^1$ and $B^1$, together with the atoms to which they are attached, are benzene, naphthylene, heteroarene, cycloalkane, cycloalkene, heterocycloalkane or heterocycloalkene; and $A^2$, $D^1$, and $E^1$ are independently selected H, OH, F, Cl, Br, I, CN, $CF_3$, C(O)OH, C(O)$NH_2$, C(O)$OR^{1A}$, $NO_2$, $OCF_3$, $CF_2CF_3$, $OCF_2CF_3$, $NH_2$, C(O)$NH_2$, $NR^1C(O)R^1$, $NR^1S(O)_2R^1$, $NR^1C(O)OR^1$, NHC(O)$NH_2$, NHC(O)$NHR^1$, NHC(O)N($R^1$)$_2$, C(O)NHOH, C(O)$NHOR^1$, C(O)$NHSO_2R^1$, $SO_2NH_2$, C(O)H, C(N)$NH_2$, C(N)$NHR^1$, C(N)N($R^1$)$_2$, CNOH, $CNOCH_3$, $N_3$, or $NHS(O)R^1$;

or $A^2$ and $B^1$, together with the atoms to which they are attached, are benzene, naphthylene, heteroarene, cycloalkane, cycloalkene, heterocycloalkane or heterocycloalkene; and $D^1$, $E^1$, and $Y^1$ are independently selected H, OH, F, Cl, Br, I, CN, $CF_3$, C(O)OH, C(O)$NH_2$, C(O)$OR^{1A}$, $NO_2$, $OCF_3$, $CF_2CF_3$, $OCF_2CF_3$, $NH_2$, C(O)$NH_2$, $NR^1C(O)R^1$, $NR^1S(O)_2R^1$, $NR^1C(O)OR^1$, NHC(O)$NH_2$, NHC(O)$NHR^1$, NHC(O)N($R^1$)$_2$, C(O)NHOH, C(O)$NHOR^1$, C(O)$NHSO_2R^1$, $SO_2NH_2$, C(O)H, C(N)$NH_2$, C(N)$NHR^1$, C(N)N($R^1$)$_2$, CNOH, $CNOCH_3$, $N_3$, or $NHS(O)R^1$;

or $A^2$ and $D^1$, together with the atoms to which they are attached, are benzene, naphthalene, heteroarene, cycloalkane, cycloalkene, heterocycloalkane or heterocycloalkene; and $B^1$, $E^1$, and $Y^1$ are independently selected H, OH, F, Cl, Br, I, CN, $CF_3$, C(O)OH, C(O)$NH_2$, C(O)$OR^{1A}$, $NO_2$, $OCF_3$, $CF_2CF_3$, $OCF_2CF_3$, $NH_2$, C(O)$NH_2$, $NR^1C(O)R^1$, $NR^1S(O)_2R^1$, $NR^1C(O)OR^1$, NHC(O)$NH_2$, NHC(O)$NHR^1$, NHC(O)N($R^1$)$_2$, C(O)NHOH, C(O)$NHOR^1$, C(O)$NHSO_2R^1$, $SO_2NH_2$, C(O)H, C(N)$NH_2$, C(N)$NHR^1$, C(N)N($R^1$)$_2$, CNOH, $CNOCH_3$, $N_3$, or $NHS(O)R^1$;

$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with benzene, heteroarene or $R^{2A}$; $R^{2A}$ is cycloalkane, cycloalkene, heterocycloalkane or heterocycloalkene;

$R^3$ is heteroaryl, which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, NC($R^{6A}$)($R^{6B}$), $R^7$, $OR^7$, $SR^7$, $S(O)R^7$, $SO_2R^7$, $NHR^7$, N($R^7$)$_2$, C(O)$R^7$, C(O)$NH_2$, C(O)$NHR^7$, C(O)N($R^7$)$_2$, NHC(O)$R^7$, $NR^7C(O)R^7$, $NHSO_2R^7$, NHC(O)$OR^7$, $SO_2NH_2$, $SO_2NHR^7$, $SO_2N(R^7)_2$, NHC(O)$NH_2$, NHC(O)$NHR^7$, NHC(O)CH($CH_3$)NHC(O)CH($CH_3$)$NH_2$, NHC(O)CH($CH_3$)NHC(O)CH($CH_3$)$NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, NH($CH_3$) or N($CH_3$)$_2$;

$R^{6A}$ and $R^{6B}$ are independently selected alkyl or, together with the N to which they are attached, $R^{6C}$;

R⁶ is aziridin-1-yl, azetidin-1-yl, pyrrolidin-1-yl or piperidin-1-yl, each having one CH₂ moiety unreplaced or replaced with O, C(O), CNOH, CNOCH₃, S, S(O), SO₂ or NH;

R⁷ is R⁸, R⁹, R¹⁰ or R¹¹;

R⁸ is phenyl, which is unfused or fused with benzene, heteroarene or R⁸ᴬ; R⁸ᴬ is cycloalkane, cycloalkene, heterocycloalkane or heterocycloalkene;

R⁹ is heteroaryl, which is unfused or fused with benzene, heteroarene or R⁹ᴬ; R⁹ᴬ is cycloalkane, cycloalkene, heterocycloalkane or heterocycloalkene;

R¹⁰ is cycloalkyl, cycloalkenyl, heterocycloalkyl, or heterocycloalkenyl each of which is unfused or fused with benzene, heteroarene or R¹⁰ᴬ; R¹⁰ᴬ is cycloalkane, cycloalkene, heterocycloalkane or heterocycloalkene;

R¹¹ is alkyl, alkenyl or alkynyl, each of which is unsubstituted or substituted with one or two or three independently selected R¹², OR¹², SR¹², S(O)R¹², SO₂R¹², C(O)R¹², CO(O)R¹², OC(O)R¹², OC(O)OR¹², NH₂, NHR¹², N(R¹²)₂, NHC(O)R¹², NR¹²C(O)R¹², NHS(O)₂R¹², NR¹²S(O)²R¹², NHC(O)OR¹², NR¹²C(O)OR¹², NHC(O)NH₂, NHC(O)NHR¹², NHC(O)N(R¹²)₂, NR¹²C(O)NHR¹², NR¹²C(O)N(R¹²)₂, C(O)NH₂, C(O)NHR¹², C(O)N(R¹²)₂, C(O)NHOH, C(O)NHOR¹², C(O)NHSO₂R¹², SO₂NH₂, SO₂NHR¹², SO₂N(R¹²)₂, C(O)H, C(O)OH, C(N)NH₂, C(N)NHR¹², C(N)N(R¹²)₂, CNOH, CNOCH₃, OH, (O), CN, N₃, NO₂, CF₃, CF₂CF₃, OCF₃, OCF₂CF₃, F, Cl, Br or I substituents;

R¹² is R¹³, R¹⁴, R¹⁵ or R¹⁶;

R¹³ is phenyl, which is unfused or fused with benzene, heteroarene or R¹³ᴬ; R¹³ᴬ is cycloalkane, cycloalkene, heterocycloalkane or heterocycloalkene;

R¹⁴ is heteroaryl, which is unfused or fused with benzene, heteroarene or R¹⁴ᴬ; R¹⁴ᴬ is cycloalkane, cycloalkene, heterocycloalkane or heterocycloalkene;

R¹⁵ is cycloalkane, cycloalkene, heterocycloalkane or heterocycloalkene, each of which is unfused or fused with benzene, heteroarene or R¹⁵ᴬ; R¹⁵ᴬ is cycloalkane, cycloalkene, heterocycloalkane or heterocycloalkene;

R¹⁶ is alkyl, alkenyl or alkynyl;

Z¹ is R²⁶ or R²⁷;

Z² is R²⁸, R²⁹ or R³⁰;

Z¹ᴬ and Z²ᴬ are both absent or are taken together to form CH₂, CH₂CH₂ or Z¹²ᴬ;

Z¹²ᴬ is C₂-C₆-alkylene having one or two CH₂ moieties replaced by NH, N(CH₃), S, S(O) or SO₂;

L¹ is a R³⁷, OR³⁷, SR³⁷, S(O)R³⁷, SO₂R³⁷, C(O)R³⁷, CO(O)R³⁷, OC(O)R³⁷, OC(O)OR³⁷, NHR³⁷, C(O)NH, C(O)NR³⁷, C(O)NHOR³⁷, C(O)NHSO₂R³⁷, SO₂NH, SO₂NHR³⁷, C(N)NH, C(N)NHR³⁷;

R²⁶ is phenylene which is unfused or fused with benzene or heteroarene or R²⁶ᴬ; R²⁶ᴬ is cycloalkane, cycloalkene, heterocycloalkane or heterocycloalkene;

R²⁷ is heteroarylene, which is unfused or fused with benzene or heteroarene or R²⁷ᴬ; R²⁷ᴬ is cycloalkane, cycloalkene, heterocycloalkane or heterocycloalkene;

R²⁸ is phenylene, which is unfused or fused with benzene, heteroarene or R²⁸ᴬ; R²⁸ᴬ is cycloalkane, cycloalkene, heterocycloalkane or heterocycloalkene;

R²⁹ is heteroarylene, which is unfused or fused with benzene or heteroarene or R²⁹ᴬ; R²⁹ᴬ is cycloalkane, cycloalkene, heterocycloalkane or heterocycloalkene;

R³⁰ is cycloalkylene, cycloalkenylene, heterocycloalkylene or heterocycloalkenylene, each of which is unfused or fused with benzene, heteroarene or R³⁰ᴬ; R³⁰ᴬ is cycloalkane, cycloalkene, heterocycloalkane or heterocycloalkene;

R³⁷ is a bond or R³⁷ᴬ;

R³⁷ᴬ is alkylene, alkenylene, or alkynylene, each of which is unsubstituted or substituted with one or two or three independently selected R³⁷ᴮ, OR³⁷ᴮ, SR³⁷ᴮ, S(O)R³⁷ᴮ, SO₂R³⁷ᴮ, C(O)R³⁷ᴮ, CO(O)R³⁷ᴮ, OC(O)R³⁷ᴮ, OC(O)OR³⁷ᴮ, NH₂, NHR³⁷ᴮ, N(R³⁷ᴮ)₂, NHC(O)R³⁷ᴮ, NR³⁷ᴮC(O)R³⁷ᴮ, NHS(O)₂R³⁷ᴮ, NR³⁷ᴮS(O)₂R³⁷ᴮ, NHC(O)OR³⁷ᴮ, NR³⁷ᴮC(O)OR³⁷ᴮ, NHC(O)NH₂, NHC(O)NHR³⁷ᴮ, NHC(O)N(R³⁷ᴮ)₂, NR³⁷ᴮC(O)NHR³⁷ᴮ, NR³⁷ᴮC(O)N(R³⁷ᴮ)₂, C(O)NH₂, C(O)NHR³⁷ᴮ, C(O)N(R³⁷ᴮ)₂, C(O)NHOH, C(O)NHOR³⁷ᴮ, C(O)NHSO₂R³⁷ᴮ, C(O)NR³⁷ᴮSO₂R³⁷ᴮ, SO₂NH₂, SO₂NHR³⁷ᴮ, SO₂N(R³⁷ᴮ)₂, C(O)H, C(O)OH, C(N)NH₂, C(N)NHR³⁷ᴮ, C(N)N(R³⁷ᴮ)₂, CNOH, CNOCH₃, OH, (O), CN, N₃, NO₂, CF₃, CF₂CF₃, OCF₃, OCF₂CF₃, F, Cl, Br or I substituents;

R³⁷ᴮ is alkyl, alkenyl, alkynyl, phenyl, heteroaryl, cycloalkyl, cycloalkenyl, heterocycloalkyl, or heterocycloalkenyl;

Z³ is R³⁸, R³⁹ or R⁴⁰;

R³⁸ is phenyl, which is unfused or fused with benzene, heteroarene or R³⁸ᴬ; R³⁸ᴬ is cycloalkane, cycloalkene, heterocycloalkane or heterocyclalkene;

R³⁹ is heteroaryl, which is unfused or fused with benzene, heteroarene or R³⁹ᴬ; R³⁹ᴬ is cycloalkane, cycloalkene, heterocycloalkane or heterocycloalkene;

R⁴⁰ is cycloalkyl, cycloalkenyl, heterocycloalkyl, or heterocycloalkenyl, each of which is unfused or fused with benzene, heteroarene or R⁴⁰ᴬ; R⁴⁰ᴬ is cycloalkane, cycloalkene, heterocycloalkane or heterocycloalkene;

wherein the moieties represented by R²⁶ and R²⁷ are unsubstituted or substituted, (i.e., if Z¹ᴬ and Z²ᴬ are absent) or further unsubstituted or further substituted (i.e., if Z¹ᴬ and Z²ᴬ are present) with one or more R⁴¹, OR⁴¹, SR⁴¹, S(O)R⁴¹, SO₂R⁴¹, C(O)R⁴¹, CO(O)R⁴¹, OC(O)R⁴¹, OC(O)OR⁴¹, NH₂, NHR⁴¹, N(R⁴¹)₂, NHC(O)R⁴¹, NR⁴¹C(O)R⁴¹, NHS(O)₂R⁴¹, NR⁴¹S(O)₂R⁴¹, NHC(O)OR⁴¹, NR⁴¹C(O)OR⁴¹, NHC(O)NH₂, NHC(O)NHR⁴¹, NHC(O)N(R⁴¹)₂, NR⁴¹C(O)NHR⁴¹, NR⁴¹C(O)N(R⁴¹)₂, C(O)NH₂, C(O)NHR⁴¹, C(O)N(R⁴¹)₂, C(O)NHOH, C(O)NHOR⁴¹, C(O)NHSO₂R⁴¹, C(O)NR⁴¹SO₂R⁴¹, SO₂NH₂, SO₂NHR⁴¹, SO₂N(R⁴¹)₂, C(O)H, C(O)OH, C(N)NH₂, C(N)NHR⁴¹, C(N)N(R⁴¹)₂, CNOH, CNOCH₃, OH, (O), CN, N₃, NO₂, CF₃, CF₂CF₃, OCF₃, OCF₂CF₃, F, Cl, Br or I substituents;

R⁴¹ is R⁴², R⁴³, R⁴⁴ or R⁴⁵;

R⁴² is phenyl, which is unfused or fused with benzene, heteroarene or R⁴²ᴬ; R⁴²ᴬ is cycloalkane, cycloalkene, heterocycloalkane or heterocycloalkene;

R⁴³ is heteroaryl, which is unfused or fused with benzene, or R⁴³ᴬ; R⁴³ᴬ is cycloalkane, cycloalkene, heterocycloalkane or heterocycloalkene;

R⁴⁴ is cycloalkyl, cycloalkenyl, heterocycloalkyl, or heterocycloalkenyl, each of which is unfused or fused with benzene, heteroarene or R⁴⁴ᴬ; R⁴⁴ᴬ is cycloalkane, cycloalkene, heterocycloalkane or heterocycloalkene;

R⁴⁵ is alkyl, alkenyl or alkynyl, each of which is unsubstituted or substituted with one or two independently selected R⁴⁶, OR⁴⁶, SR⁴⁶, S(O)R⁴⁶, SO₂R⁴⁶, C(O)R⁴⁶, CO(O)R⁴⁶, OC(O)R⁴⁶, OC(O)OR⁴⁶, NH₂, NHR⁴⁶, N(R⁴⁶)₂, NHC(O)R⁴⁶, NR⁴⁶C(O)R⁴⁶, NHS(O)₂R⁴⁶, NR⁴⁶S(O)₂R⁴⁶, NHC(O)OR⁴⁶, NR⁴⁶C(O)OR⁴⁶, NHC(O)NH₂, NHC(O)NHR⁴⁶, NHC(O)N(R⁴⁶)₂, NR⁴⁶C(O)NHR⁴⁶, NR⁴⁶C(O)N(R⁴⁶)₂, C(O)NH₂, C(O)NHR⁴⁶, C(O)N(R⁴⁶)₂, C(O)NHOH, C(O)NHOR⁴⁶, C(O)NHSO₂R⁴⁶, C(O)NR⁴⁶SO₂R⁴⁶, SO₂NH₂, SO₂NHR⁴⁶, SO₂N(R⁴⁶)₂, C(O)H, C(O)OH, C(N)NH₂, C(N)NHR⁴⁶, C(N)N(R⁴⁶)₂, CNOH, CNOCH₃, OH, (O), CN, N₃, NO₂, CF₃, CF₂CF₃, OCF₃, OCF₂CF₃, F, Cl, Br or I substituents;

R⁴⁶ is alkyl, alkenyl, alkynyl, R⁴⁷, R⁴⁸ or R⁴⁹;

$R^{47}$ is phenyl, which is unfused or fused with benzene, heteroarene or $R^{47A}$; $R^{47A}$ is cycloalkane, cycloalkene, heterocycloalkane or heterocycloalkene;

$R^{48}$ is heteroaryl, which is unfused or fused with benzene, heteroarene or $R^{48A}$; $R^{48A}$ is cycloalkane, cycloalkene, heterocycloalkane or heterocycloalkene;

$R^{49}$ is cycloalkyl, cycloalkenyl, heterocycloalkyl, or heterocycloalkenyl, each of which is unfused or fused with benzene, heteroarene or $R^{49A}$; $R^{49A}$ is cycloalkane, cycloalkene, heterocycloalkane or heterocycloalkene;

wherein the cyclic moieties represented by $E^1$ and $Y^1$ together, $Y^1$ and $B^1$ together, $A^2$ and $B^1$ together, $A^2$ and $D^1$ together, $R^{1A}$, $R^2$, $R^{2A}$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{28}$, $R^{28A}$, $R^{29}$, $R^{29A}$, $R^{30}$, $R^{30A}$, $R^{37B}$, $R^{38}$, $R^{38A}$, $R^{39}$, $R^{39A}$, $R^{40}$ and $R^{40A}$ are independently unsubstituted, further unsubstituted, substituted or further substituted with one or more independently selected $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I substituents;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl, or alkynyl, each of which is unsubstituted or substituted with one or two or three independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I substituents;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl, or alkenyl, each of which is unsubstituted or substituted with one or two or three independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the cyclic moieties represented by $R^{58}$, $R^{59}$, $R^{60}$, $R^{63}$, $R^{64}$, $R^{65}$, and $R^{67}$ are unsubstituted or substituted with one or more independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R_{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})^2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I substituents;

$R^{68}$ is $R^{69}$, $R^{70}$, $R^{71}$ or $R^{72}$;

$R^{69}$ is phenyl, which is unfused or fused with benzene, heteroarene or $R^{69A}$; $R^{69A}$ is cycloalkane, cycloalkene, heterocycloalkane or heterocycloalkene;

$R^{70}$ is heteroaryl, which is unfused or fused with benzene, heteroarene or $R^{70A}$; $R^{70A}$ is cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with benzene, heteroarene or $R^{71A}$; $R^{71A}$ is cycloalkane, cycloalkene, heterocycloalkane or heterocycloalkene;

$R^{72}$ is alkyl, alkenyl, or alkenyl, each of which is unsubstituted or substituted with one or two or three independently selected $R^{73}$, $OR^{73}$, $SR^{73}$, $S(O)R^{73}$, $SO_2R^{73}$, $C(O)R^{73}$, $CO(O)R^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I substituents;

$R^{73}$ is alkyl, alkenyl, alkenyl, phenyl, heteroaryl, cycloalkyl, cycloalkenyl, heterocycloalkyl, or heterocycloalkenyl; and the moieties represented by $R^{69}$, $R^{70}$, and $R^{71}$ are unsubstituted or substituted with one or more independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, (O), $CN$, $N_3$, $NO_2$, $CF_3$, $CF_2CF_3$, $OCF_3$, $OCF_2CF_3$, F, Cl, Br or I substituents.

Another embodiment of this invention pertains to compounds of Formula (I), wherein $A^1$ is N or $C(A^2)$;

$A^2$, $B^1$, $D^1$, $E^1$, and $Y^1$ are independently selected H, OH, F, Cl, Br, I, CN, $CF_3$, $C(O)OH$, $C(O)NH_2$, $C(O)OR^{1A}$; $NO_2$, $OCF_3$, $CF_2CF_3$, $OCF_2CF_3$, $NH_2$, $C(O)NH_2$, $NR^1C(O)R^1$, $NR^1S(O)_2R^1$, $NR^1C(O)OR^1$, $NHC(O)NH_2$, $NHC(O)NHR^1$, $NHC(O)N(R^1)_2$, $C(O)NHOH$, $C(O)NHOR^1$, $C(O)NHSO_2R^1$, $SO_2NH_2$, $C(O)H$, $C(N)NH_2$, $C(N)NHR^1$, $C(N)N(R^1)_2$, $CNOH$, $CNOCH_3$, $N_3$, or $NHS(O)R^1$;

or $E^1$ and $Y^1$, together with the atoms to which they are attached, are benzene, naphthylene, heteroarene, cycloalkane, cycloalkene, heterocycloalkane or heterocycloalkene; and $A^2$, $B^1$, and $D^1$ are independently selected H, OH, F, Cl, Br, I, CN, $CF_3$, C(O)OH, C(O)$NH_2$, C(O)$OR^{14}$, $NO_2$, $OCF_3$, $CF_2CF_3$, $OCF_2CF_3$, $NH_2$, C(O)$NH_2$, $NR^1$C(O)$R^1$, $NR^1S(O)_2R^1$, $NR^1$C(O)$OR^1$, NHC(O)$NH_2$, NHC(O)$NHR^1$, NHC(O)N($R^1$)$_2$, C(O)NHOH, C(O)$NHOR^1$, C(O)$NHSO_2R^1$, $SO_2NH_2$, C(O)H, C(N)$NH_2$, C(N)$NHR^1$, C(N)N($R^1$)$_2$, CNOH, $CNOCH_3$, $N_3$, or NHS(O)$R^1$;

or $Y^1$ and $B^1$, together with the atoms to which they are attached, are benzene, naphthylene, heteroarene, cycloalkane, cycloalkene, heterocycloalkane or heterocycloalkene; and $A^2$, $D^1$, and $E^1$ are independently selected H, OH, F, Cl, Br, I, CN, $CF_3$, C(O)OH, C(O)$NH_2$, C(O)$OR^{14}$, $NO_2$, $OCF_3$, $CF_2CF_3$, $OCF_2CF_3$, $NH_2$, C(O)$NH_2$, $NR^1$C(O)$R^1$, $NR^1S(O)_2R^1$, $NR^1$C(O)$OR^1$, NHC(O)$NH_2$, NHC(O)$NHR^1$, NHC(O)N($R^1$)$_2$, C(O)NHOH, C(O)$NHOR^1$, C(O)$NHSO_2R^1$, $SO_2NH_2$, C(O)H, C(N)$NH_2$, C(N)$NHR^1$, C(N)N($R^1$)$_2$, CNOH, $CNOCH_3$, $N_3$, or NHS(O)$R^1$;

or $A^2$ and $B^1$, together with the atoms to which they are attached, are benzene, naphthylene, heteroarene, cycloalkane, cycloalkene, heterocycloalkane or heterocycloalkene; and $D^1$, $E^1$, and $Y^1$ are independently selected H, OH, F, Cl, Br, I, CN, $CF_3$, C(O)OH, C(O)$NH_2$, C(O)$OR^{14}$, $NO_2$, $OCF_3$, $CF_2CF_3$, $OCF_2CF_3$, $NH_2$, C(O)$NH_2$, $NR^1$C(O)$R^1$, $NR^1S(O)_2R^1$, $NR^1$C(O)$OR^1$, NHC(O)$NH_2$, NHC(O)$NHR^1$, NHC(O)N($R^1$)$_2$, C(O)NHOH, C(O)$NHOR^1$, C(O)$NHSO_2R^1$, $SO_2NH_2$, C(O)H, C(N)$NH_2$, C(N)$NHR^1$, C(N)N($R^1$)$_2$, CNOH, $CNOCH_3$, $N_3$, or NHS(O)$R^1$;

or $A^2$ and $D^1$, together with the atoms to which they are attached, are benzene, naphthalene, heteroarene, cycloalkane, cycloalkene, heterocycloalkane or heterocycloalkene; and $B^1$, $E^1$, and $Y^1$ are independently selected H, OH, F, Cl, Br, I, CN, $CF_3$, C(O)OH, C(O)$NH_2$, C(O)$OR^{14}$, $NO_2$, $OCF_3$, $CF_2CF_3$, $OCF_2CF_3$, $NH_2$, C(O)$NH_2$, $NR^1$C(O)$R^1$, $NR^1S(O)_2R^1$, $NR^1$C(O)$OR^1$, NHC(O)$NH_2$, NHC(O)$NHR^1$, NHC(O)N($R^1$)$_2$, C(O)NHOH, C(O)$NHOR^1$, C(O)$NHSO_2R^1$, $SO_2NH_2$, C(O)H, C(N)$NH_2$, C(N)$NHR^1$, C(N)N($R^1$)$_2$, CNOH, $CNOCH_3$, $N_3$, or NHS(O)$R^i$;

$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with benzene, heteroarene or $R^{2A}$; $R^{2A}$ is cycloalkane, cycloalkene, heterocycloalkane or heterocycloalkene;

$R^3$ is heteroaryl, which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, NC($R^{6A}$)($R^{6B}$), $R^7$, $OR^7$, $SR^7$, S(O)$R^7$, $SO_2R^7$, $NHR^7$, N($R^7$)$_2$, C(O)$R^7$, C(O)$NH_2$, C(O)$NHR^7$, C(O)N($R^7$)$_2$, NHC(O)$R^7$, $NR^7$C(O)$R^7$, $NHSO_2R^7$, NHC(O)$OR^7$, $SO_2NH_2$, $SO_2NHR^7$, $SO_2N(R^7)_2$, NHC(O)$NH_2$, NHC(O)$NHR^7$, NHC(O)CH($CH_3$)NHC(O)CH($CH_3$)$NH_2$, NHC(O)CH($CH_3$)NHC(O)CH($CH_3$)$NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, NH($CH_3$) or N($CH_3$)$_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl, or heterocycloalkenyl each of which is unfused or fused with benzene, heteroarene or $R^{14}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $SR^{12}$, S(O)$R^{12}$, $SO_2R^{12}$, C(O)$R^{12}$, CO(O)$R^{12}$, OC(O)$R^{12}$, OC(O)$OR^{12}$, $NH_2$, $NHR^{12}$, N($R^{12}$)$_2$, NHC(O)$R^{12}$, $NR^{12}$C(O)$R^{12}$, NHS(O)$_2R^{12}$, $NR^{12}S(O)_2R^{12}$, NHC(O)$OR^{12}$, $NR^{12}$C(O)$OR^{12}$, NHC(O)$NH_2$, NHC(O)$NHR^{12}$, NHC(O)N($R^{12}$)$_2$, $NR^{12}$C(O)$NHR^{12}$, $NR^{12}$C(O)N($R^{12}$)$_2$, C(O)$NH_2$, C(O)$NHR^{12}$, C(O)N($R^{12}$)$_2$, C(O)NHOH, C(O)$NHOR^{12}$, C(O)$NHSO_2R^{12}$, C(O)$NR^{12}SO_2R^{12}$, $SO_2NH_2$, $SO_2NHR^{12}$, $SO_2N(R^{12})_2$, C(O)H, C(O)OH, C(N)$NH_2$, C(N)$NHR^{12}$, C(N)N($R^{12}$)$_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$Z^1$ is $R^{26}$ or $R^{27}$;

$Z^2$ is $R^{28}$, $R^{29}$ or $R^{30}$;

$Z^{1A}$ and $Z^{2A}$ are both absent or are taken together to form $CH_2$, $CH_2CH_2$ or $Z^{12A}$;

$Z^{12A}$ is $C_2$-$C_6$-alkylene having one or two $CH_2$ moieties replaced by NH, N($CH_3$), S, S(O) or $SO_2$;

$L^1$ is a $R^{37}$, $OR^{37}$, $SR^{37}$, S(O)$R^{37}$, $SO_2R^{37}$, C(O)$R^{37}$, CO(O)$R^{37}$, OC(O)$R^{37}$, OC(O)$OR^{37}$, $NHR^{37}$, C(O)NH, C(O)$NR^{37}$, C(O)$NHOR^{37}$, C(O)$NHSO_2R^{37}$, $SO_2NH$, $SO_2NHR^{37}$, C(N)NH, C(N)$NHR^{37}$;

$R^{26}$ is phenylene which is unfused or fused with benzene or heteroarene or $R^{26A}$; $R^{26A}$ is cycloalkane, cycloalkene, heterocycloalkane or heterocycloalkene;

$R^{27}$ is heteroarylene, which is unfused or fused with benzene or heteroarene or $R^{27A}$; $R^{27A}$ is cycloalkane, cycloalkene, heterocycloalkane or heterocycloalkene;

$R^{28}$ is phenylene, which is unfused or fused with benzene, heteroarene or $R^{28A}$; $R^{28A}$ is cycloalkane, cycloalkene, heterocycloalkane or heterocycloalkene;

$R^{29}$ is heteroarylene, which is unfused or fused with benzene or heteroarene or $R^{29A}$; $R^{29A}$ is cycloalkane, cycloalkene, heterocycloalkane or heterocycloalkene;

$R^{30}$ is cycloalkylene, cycloalkenylene, heterocycloalkylene or heterocycloalkenylene, each of which is unfused or fused with benzene, heteroarene or $R^{30A}$; $R^{30A}$ is cycloalkane, cycloalkene, heterocycloalkane or heterocycloalkene;

$R^{37}$ is a bond or $R^{37A}$;

$R^{37A}$ is alkylene, alkenylene, or alkynylene, each of which is unsubstituted or substituted with one or two or three independently selected $R^{37B}$, $OR^{37B}$, $SR^{37B}$, $S(O)R^{37B}$, $SO_2R^{37B}$, $C(O)R^{37B}$, $CO(O)R^{37B}$, $OC(O)R^{37B}$, $OC(O)OR^{37B}$, $NH_2$, $NHR^{37B}$, $N(R^{37B})_2$, $NHC(O)R^{37B}$, $NR^{37B}C(O)R^{37B}$, $NHS(O)_2R^{37B}$, $NR^{37B}S(O)_2R^{37B}$, $NHC(O)OR^{37B}$, $NR^{37B}C(O)OR^{37B}$, $NHC(O)NH_2$, $NHC(O)NHR^{37B}$, $NHC(O)N(R^{37B})_2$, $NR^{37B}C(O)NHR^{37B}$, $NR^{37B}C(O)N(R^{37B})_2$, $C(O)NH_2$, $C(O)NHR^{37B}$, $C(O)N(R^{37B})_2$, $C(O)NHOH$, $C(O)NHOR^{37B}$, $C(O)NHSO_2R^{37B}$, $C(O)NR^{37B}SO_2R^{37B}$, $SO_2NH_2$, $SO_2NHR^{37B}$, $SO_2N(R^{37B})_2$, $C(O)H$, $C(O)OH$, $C(N)NH_2$, $C(N)NHR^{37B}$, $C(N)N(R^{37B})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{37B}$ is alkyl, alkenyl, alkynyl, phenyl, heteroaryl, cycloalkyl, cycloalkenyl, heterocycloalkyl, or heterocycloalkenyl;

$Z^3$ is $R^{38}$, $R^{39}$ or $R^{40}$;

$R^{38}$ is phenyl, which is unfused or fused with benzene, heteroarene or $R^{38A}$; $R^{38A}$ is cycloalkane, cycloalkene, heterocycloalkane or heterocyclalkene;

$R^{39}$ is heteroaryl, which is unfused or fused with benzene, heteroarene or $R^{39A}$; $R^{39A}$ is cycloalkane, cycloalkene, heterocycloalkane or heterocycloalkene;

$R^{40}$ is cycloalkyl, cycloalkenyl, heterocycloalkyl, or heterocycloalkenyl, each of which is unfused or fused with benzene, heteroarene or $R^{40A}$; $R^{40A}$ is cycloalkane, cycloalkene, heterocycloalkane or heterocycloalkene;

wherein the moieties represented by $R^{26}$ and $R^{27}$ are substituted, (i.e., if $Z^{1A}$ and $Z^{2A}$ are absent) or further substituted (i.e., if $Z^{1A}$ and $Z^{2A}$ are present) with one or more $OR^{41}$;

$R^{41}$ is $R^{42}$;

$R^{42}$ is phenyl, which is fused with heteroarene;

wherein the cyclic moieties represented by $E^1$ and $Y^1$ together, $Y^1$ and $B^1$ together, $A^2$ and $B^1$ to ether $A^2$ and $D^1$ together $R^{1A}$, $R^2$, $R^{2A}$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{28}$, $R^{28A}$, $R^{29}$, $R^{29A}$, $R^{30}$, $R^{30A}$, $R^{37B}$, $R^{38}$, $R^{38A}$, $R^{39}$, $R^{39A}$, $R^{40}$, and $R^{40A}$ are independently unsubstituted, further unsubstituted, substituted or further substituted with one or more independently selected $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl, or alkynyl, each of which is unsubstituted or substituted with one or two or three independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)^2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl, or alkenyl, each of which is unsubstituted or substituted with one or two or three independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the cyclic moieties represented by $R^{58}$, $R^{59}$, $R^{60}$, $R^{63}$, $R^{64}$, $R^{65}$, and $R^{67}$ are unsubstituted or substituted with one or more independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{68}$ is $R^{69}$, $R^{70}$, $R^{71}$ or $R^{72}$;

$R^{69}$ is phenyl, which is unfused or fused with benzene, heteroarene or $R^{69A}$; $R^{69A}$ is cycloalkane, cycloalkene, heterocycloalkane or heterocycloalkene;

$R^{70}$ is heteroaryl, which is unfused or fused with benzene, heteroarene or $R^{70A}$; $R^{70A}$ is cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with benzene, heteroarene or $R^{71A}$; $R^{71A}$ is cycloalkane, cycloalkene, heterocycloalkane or heterocycloalkene;

$R^{72}$ is alkyl, alkenyl, or alkenyl, each of which is unsubstituted or substituted with one or two or three independently selected $R^{73}$, $OR^{73}$, $SR^{73}$, $S(O)R^{73}$, $SO_2R^{73}$, $C(O)R^{73}$, $CO(O)R^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{73}$ is alkyl, alkenyl, alkenyl, phenyl, heteroaryl, cycloalkyl, cycloalkenyl, heterocycloalkyl, or heterocycloalkenyl; and the moieties represented by $R^{69}$, $R^{70}$, and $R^{71}$ are unsubstituted or substituted with one or more independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, OH, (O), CN, $N_3$, $NO_2$, $CF_3$, $CF_2CF_3$, $OCF_3$, $OCF_2CF_3$, F, Cl, Br or I substituents.

In another embodiment of Formula (I), $A^1$ is N or $C(A^2)$;

$A^2$, $B^1$, $D^1$, $E^1$, and $Y^1$ are independently selected H, OH, F, Cl, Br, I, CN, $CF_3$, or $NO_2$;

or $E^1$ and $Y^1$, together with the atoms to which they are attached, are benzene or heteroarene, and $A^2$, $B^1$, and $D^1$ are independently selected H;

or $Y^1$ and $B^1$, together with the atoms to which they are attached, are benzene, and $A^2$, $D^1$, and $E^1$ are independently selected H;

or $A^2$ and $B^1$, together with the atoms to which they are attached, are heteroarene, cycloalkane, heterocycloalkane or heterocycloalkene; and $D^1$, $E^1$, and $Y^1$ are independently selected H, F, Cl, Br, I, or $NO_2$;

$Z^1$ is $R^{26}$;

$Z^2$ is $R^{30}$;

$Z^{1A}$ and $Z^{2A}$ are both absent;

$L^1$ is a $R^{37}$;

$R^{26}$ is phenylene;

$R^{30}$ is heterocycloalkylene;

$R^{37}$ is $R^{37A}$;

$R^{37A}$ is alkylene or alkenylene, each of which is unsubstituted or substituted with $R^{37B}$;

$R^{37B}$ is phenyl;

$Z^3$ is $R^{38}$ or $R^{40}$;

$R^{38}$ is phenyl;

$R^{40}$ is cycloalkenyl;

wherein the moieties represented by $R^{26}$ and $R^{27}$ are unsubstituted or substituted, (i.e., if $Z^{1A}$ and $Z^{2A}$ are absent) or further unsubstituted or further substituted (i.e., if $Z^{1A}$ and $Z^{2A}$ are present) with one or more $R^{41}$, $OR^{41}$, $SR^{41}$, $S(O)R^{41}$, $SO_2R^{41}$, or $NHR^{41}$ substituents;

$R^{41}$ is $R^{42}$ or $R^{45}$;

$R^{42}$ is phenyl, which is unfused or fused with heteroarene;

$R^{45}$ is alkyl, which is unsubstituted or substituted with one or two independently selected $R^{46}$;

$R^{46}$ is $R^{47}$;

$R^{47}$ is phenyl;

wherein the cyclic moieties represented by $E^1$ and $Y^1$ together, $Y^1$ and $B^1$ together, $A^2$ and $B^1$ together, $R^{30}$, $R^{30A}$, $R^{37B}$, $R^{38}$, and $R^{40}$ are independently unsubstituted, further unsubstituted, substituted or further substituted with one or more independently selected $R^{57}$, $OR^{57}$, $NR^{57}C(O)R^{57}$, or (O);

$R^{57}$ is $R^{58}$, or $R^{61}$;

$R^{58}$ is phenyl, $R^{61}$ is alkyl, which is unsubstituted or substituted with one or two or three independently selected $N(R^{62})_2$, or F, Cl, Br or I substituents;

$R^{62}$ is $R^{66}$;

$R^{66}$ is alkyl; and wherein the cyclic moieties represented by $R^{58}$ is unsubstituted or substituted with one or more independently selected F, Cl, Br or I substituents.

In one embodiment of Formula (I), $A^1$ is $C(A^2)$; and $A^2$ is H. In another embodiment of Formula (I), $A^1$ is N.

In another embodiment of Formula (I), $A^2$, $B^1$, $D^1$, $E^1$, and $Y^1$ are independently selected H, OH, F, Cl, Br, I, CN, $CF_3$, or $NO_2$. In another embodiment of Formula (I), $A^2$, $B^1$, $D^1$, $E^1$, and $Y^1$ are independently selected H, OH, F, Cl, Br, CN, $CF_3$, or $NO_2$. In another embodiment of Formula (I), $A^1$ is $C(A^2)$; $A^2$ is H; and $B^1$, $D^1$, $E^1$, and $Y^1$ are independently selected H, OH, F, Cl, Br, CN, $CF_3$, or $NO_2$. In another embodiment of Formula (I), $A^1$ is $C(A^2)$; and $A^2$, $B^1$, $D^1$, $Y^1$, and $E^1$ are H. In another embodiment of Formula (I), $A^1$ is $C(A^2)$; $A^2$, $B^1$, $D^1$, and $E^1$ are H; and $Y^1$ is $NO_2$. In another embodiment of Formula (I), $A^1$ is $C(A^2)$; $A^2$, $B^1$, $D^1$, and $E^1$ are H; and $Y^1$ is Br. In another embodiment of Formula (I), $A^1$ is $C(A^2)$; $A^2$, $B^1$, $D^1$, and $E^1$ are H; and $Y^1$ is F. In another embodiment of Formula (I), $A^1$ is $C(A^2)$; $A^2$, $B^1$, $D^1$, and $E^1$ are H; and $Y^1$ is CN. In another embodiment of Formula (I), $A^1$ is $C(A^2)$; $A^2$, $B^1$, $D^1$, and $E^1$ are H; and $Y^1$ is $CF_3$. In another embodiment of Formula (I), $A^1$ is $C(A^2)$; $A^2$, $B^1$, $D^1$, and $E^1$ are H; and $Y^1$ is Cl. In another embodiment of Formula (I), $A^2$, $D^1$, and $E^1$ are H; $B^1$ is Cl, and $Y^1$ is $NO_2$. In another embodiment of Formula (I), $A^1$ is $C(A^2)$; $Y^1$, $A^2$, $B^1$, and $E^1$ are H; and $D^1$ is Br. In another embodiment of Formula (I), $A^1$ is $C(A^2)$; $Y^1$, $A^2$, $D^1$, and $E^1$ are H; and $B^1$ is Br. In another embodiment of Formula (I), $A^1$ is $C(A^2)$; $Y^1$, $A^2$, $D^1$, and $E^1$ are H; and $B^1$ is $NO_2$. In another embodiment of Formula (I), $A^1$ is $C(A^2)$; $Y^1$, $A^2$, $D^1$, and $E^1$ are H; and $B^1$ is OH. In another embodiment of Formula (I), $A^1$ is $C(A^2)$; $Y^1$, $A^2$, $D^1$, and $E^1$ are H; and $B^1$ is F. In another embodiment of Formula (I), $E^1$ and $Y^1$, together with the atoms to which they are attached, are heteroarene, and $A^2$, $B^1$, and $D^1$ are H. In another embodiment of Formula (I), $Y^1$ and $B^1$, together with the atoms to which they are attached, are benzene, and $A^2$, $D^1$, and $E^1$ are independently selected H. In another embodiment of Formula (I), $E^1$ and $Y^1$, together with the atoms to which they are attached, are benzene and $A^2$, $B^1$, and $D^1$ are H. In another embodiment of Formula (I), $A^2$ and $B^1$, together with the atoms to which they are attached, are heteroarene; and $D^1$, $E^1$, and $Y^1$ are independently selected H, F, Cl, Br, I, or $NO_2$. In another embodiment of Formula (I), $A^2$ and $B^1$, together with the atoms to which they are attached, are cycloalkane; and $D^1$, $E^1$, and $Y^1$ are independently selected H, F, Cl, Br, I, or $NO_2$. In another embodiment of Formula (I), $A^2$ and $B^1$, together with the atoms to which they are attached, are heterocycloalkane; and $D^1$, $E^1$, and $Y^1$ are independently selected H, F, Cl, Br, I, or $NO_2$. In another embodiment of Formula (I), $A^2$ and $B^1$, together with the atoms to which they are attached, are heterocycloalkene; and $D^1$, $E^1$, and $Y^1$ are independently selected H, F, Cl, Br, I, or $NO_2$.

Still another embodiment pertains to compounds having Formula I, which are

4-[4-(3,3-diphenylprop-2-enyl)piperazin-1-yl]-N-[(3-nitrophenyl)sulfonyl]benzamide;

N-[(2-bromophenyl)sulfonyl]-4-(4-{[2-(4-chlorophenyl)cyclohex-1-en-1-yl]methyl}piperazin-1-yl)benzamide;

N-[(3-bromophenyl)sulfonyl]-4-(4-{[2-(4-chlorophenyl)cyclohex-1-en-1-yl]methyl}piperazin-1-yl)benzamide;

N-[(4-bromophenyl)sulfonyl]-4-(4-{[2-(4-chlorophenyl)cyclohex-1-en-1-yl]methyl}piperazin-1-yl)benzamide;

4-{4-[(4'-chloro-1,1'-biphenyl-2-yl)methyl]piperazin-1-yl}-N-[(3-nitrophenyl)sulfonyl]benzamide;

4-{4-[(4'-chloro-1,1'-biphenyl-2-yl)methyl]piperazin-1-yl}-N-(phenylsulfonyl)benzamide;

2-(benzyloxy)-4-{4-[(4'-chloro-1,1'-biphenyl-2-yl)methyl]piperazin-1-yl}-N-[(3-nitrophenyl)sulfonyl]benzamide;

4-{4-[(4'-chloro-1,1'-biphenyl-2-yl)methyl]piperazin-1-yl}-N-[(3-nitrophenyl)sulfonyl]-2-(2-phenylethoxy)benzamide;

4-{4-[(4'-chloro-1,1'-biphenyl-2-yl)methyl]piperazin-1-yl}-N-[(3-nitrophenyl)sulfonyl]-2-phenoxybenzamide;

4-{4-[(4'-chloro-1,1'-biphenyl-2-yl)methyl]piperazin-1-yl}-2-phenoxy-N-(phenylsulfonyl)benzamide;

N-[(4-bromophenyl)sulfonyl]-4-{4-[(4'-chloro-1,1'-biphenyl-2-yl)methyl]piperazin-1-yl}benzamide;

4-[4-(1,1'-biphenyl-4-ylmethyl)-3-isopropylpiperazin-1-yl]-N-(phenylsulfonyl)benzamide;

4-{4-[(4'-chloro-1,1'-biphenyl-2-yl)methyl]piperazin-1-yl}-N-[(3-nitrophenyl)sulfonyl]-2-(phenylthio)benzamide;

2-(benzylamino)-4-{4-[(4'-chloro-1,1'-biphenyl-2-yl)methyl]piperazin-1-yl}-N-[(3-nitrophenyl)sulfonyl]benzamide;

2-benzyl-4-{4-[(4'-chloro-1,1'-biphenyl-2-yl)methyl]piperazin-1-yl}-N-[(3-nitrophenyl)sulfonyl]benzamide;

4-{4-[(4'-chloro-1,1'-biphenyl-2-yl)methyl]piperazin-1-yl}-N-[(4-nitrophenyl)sulfonyl]benzamide;

4-{4-[(4'-chloro-1,1'-biphenyl-2-yl)methyl]piperazin-1-yl}-N-[(4-hydroxyphenyl)sulfonyl]benzamide;

4-{4-[(4'-chloro-1,1'-biphenyl-2-yl)methyl]piperazin-1-yl}-N-[(3-nitrophenyl)sulfonyl]-2-(2-phenylethyl)benzamide;

4-{4-[(4'-chloro-1,1'-biphenyl-2-yl)methyl]piperazin-1-yl}-N-[(4-fluorophenyl)sulfonyl]benzamide;

4-{4-[(4'-chloro-1,1'-biphenyl-2-yl)methyl]piperazin-1-yl}-N-[(3-fluorophenyl)sulfonyl]benzamide;

4-{4-[(4'-chloro-1,1'-biphenyl-2-yl)methyl]piperazin-1-yl}-N-[(3-nitrophenyl)sulfonyl]-2-(phenylsulfinyl)benzamide;

4-{4-[(4'-chloro-1,1'-biphenyl-2-yl)methyl]piperazin-1-yl}-N-[(4-nitrophenyl)sulfonyl]-2-phenoxybenzamide;

4-{4-[(4'-chloro-1,1'-biphenyl-2-yl)methyl]piperazin-1-yl}-N-[(3-fluorophenyl)sulfonyl]-2-phenoxybenzamide;

4-{4-[(4'-chloro-1,1'-biphenyl-2-yl)methyl]piperazin-1-yl}-N-[(4-fluorophenyl)sulfonyl]-2-phenoxybenzamide;

4-{4-[(4'-chloro-1,1'-biphenyl-2-yl)methyl]piperazin-1-yl}-2-methoxy-N-[(3-nitrophenyl)sulfonyl]benzamide;

4-{4-[(4'-chloro-1,1'-biphenyl-2-yl)methyl]piperazin-1-yl}-N-[(3-nitrophenyl)sulfonyl]-2-(phenylsulfonyl)benzamide;

4-{4-[(4'-chloro-1,1'-biphenyl-2-yl)methyl]piperazin-1-yl}-N-[(4-chloro-3-nitrophenyl)sulfonyl]-2-phenoxybenzamide;

4-[4-({4'-chloro-3-[2-(dimethylamino)ethoxy]-1,1'-biphenyl-2-yl}methyl)piperazin-1-yl]-2-(1H-indol-4-yloxy)-N-[(3-nitrophenyl)sulfonyl]benzamide;

4-[4-({4'-chloro-3-[2-(dimethylamino)ethoxy]-1,1'-biphenyl-2-yl}methyl)piperazin-1-yl]-2-(1H-indol-4-yloxy)-N-(phenylsulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-(phenylsulfonyl)benzamide;

4-(4-{[2-(4-chlorophenyl)-4,4-dimethylcyclohex-1-en-1-yl]methyl}piperazin-1-yl)-N-[(3-cyanophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-(trifluoromethyl)phenyl]sulfonyl}benzamide;

4-(4-{[2-(4-chlorophenyl)-4,4-dimethylcyclohex-1-en-1-yl]methyl}piperazin-1-yl)-N-[(3-chlorophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-[(3-fluorophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-(2-naphthylsulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-(isoquinolin-5-ylsulfonyl)benzamide;

N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

4-{4-[(4'-chlorobiphenyl-2-yl)methyl]piperazin-1-yl}-N-[(2-chloropyridin-3-yl)sulfonyl]benzamide;

4-{4-[(4'-chlorobiphenyl-2-yl)methyl]piperazin-1-yl}-N-[(7-nitro-1H-benzimidazol-5-yl)sulfonyl]benzamide;

4-{4-[(4'-chlorobiphenyl-2-yl)methyl]piperazin-1-yl}-N-[(3-oxo-3,4-dihydro-2H-1,4-benzoxazin-6-yl)sulfonyl]benzamide;

4-{4-[(4'-chlorobiphenyl-2-yl)methyl]piperazin-1-yl}-N-[(6-chloro-1,1-dioxido-2H-1,2,4-benzothiadiazin-7-yl)sulfonyl]benzamide;

4-{4-[(4'-chlorobiphenyl-2-yl)methyl]piperazin-1-yl}-N-({5-[ethyl(trifluoroacetyl)amino]-1-naphthyl}sulfonyl)benzamide;

4-{4-[(4'-chlorobiphenyl-2-yl)methyl]piperazin-1-yl}-N-[(5,5,8,8-tetramethyl-5,6,7,8-tetrahydronaphthalen-2-yl)sulfonyl]benzamide;

4-{4-[(4'-chlorobiphenyl-2-yl)methyl]piperazin-1-yl}-N-[(2-oxo-2H-chromen-6-yl)sulfonyl]benzamide;

and therapeutically acceptable salts, prodrugs, salts of prodrugs and metabolites thereof.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (II)

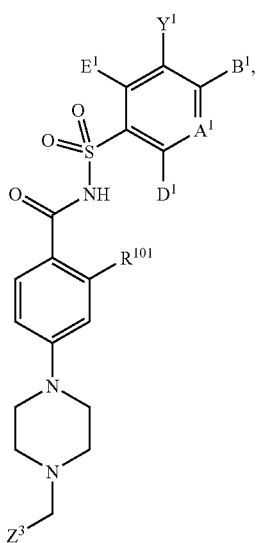

(II)

wherein $A^1$, $B^1$, $D^1$, $E^1$, $Y^1$, and $Z^3$ are as described for Formula (I) and $R^{101}$ is H or is as described for substitutents on $R^{26}$.

In one embodiment of Formula (II), $A^1$ is N, or $C(A^2)$;

$A^2$, $B^1$, $D^1$, $E^1$, and $Y^1$ are independently selected H, OH, F, Cl, Br, I, CN, $CF_3$, or $NO_2$;

or $E^1$ and $Y^1$, together with the atoms to which they are attached, are benzene or heteroarene, and $A^2$, $B^1$, and $D^1$ are independently selected H;

or $Y^1$ and $B^1$, together with the atoms to which they are attached, are benzene, and $A^2$, $D^1$, and $E^1$ are independently selected H;

or $A^2$ and $B^1$, together with the atoms to which they are attached, are heteroarene, cycloalkane, heterocycloalkane or heterocycloalkene; and $D^1$, $E^1$, and $Y^1$ are independently selected H, F, Cl, Br, I, or $NO_2$;

$Z^3$ is $R^{38}$ or $R^{40}$;

$R^{38}$ is phenyl;

$R^{40}$ is cycloalkenyl;

wherein $R^{101}$ is $R^{41}$, $OR^{41}$, $SR^{41}$, $S(O)R^{41}$, $SO_2R^{41}$, or $NHR^{41}$ substituents;

$R^{41}$ is $R^{42}$ or $R^{45}$;

$R^{42}$ is phenyl, which is unfused or fused with heteroarene;

$R^{45}$ is alkyl, which is unsubstituted or substituted with one or two independently selected $R^{46}$;

$R^{46}$ is $R^{47}$;

$R^{47}$ is phenyl;

wherein the cyclic moieties represented by $E^1$ and $Y^1$ together, $Y^1$ and $B^1$ together, $A^2$ and $B^1$ together, $R^{30}$, $R^{30A}$, $R^{37B}$, $R^{38}$, and $R^{40}$ are independently unsubstituted, further unsubstituted, substituted or further substituted with one or more independently selected $R^{57}$, $OR^{57}$, $NR^{57}C(O)R^{57}$, or (O);

$R^{57}$ is $R^{58}$, or $R^{61}$;

$R^{58}$ is phenyl;

$R^{61}$ is alkyl, which is unsubstituted or substituted with one or two or three independently selected $N(R^{62})_2$, or F, Cl, Br or I substituents;

$R^{62}$ is $R^{66}$;

$R^{66}$ is alkyl; and wherein the cyclic moieties represented by $R^{58}$ is unsubstituted or substituted with one or more independently selected F, Cl, Br or I substituents.

In one embodiment of Formula (II), $A^1$ is $C(A^2)$; and $A^2$ is H. In another embodiment of Formula (II), $A^1$ is N. In another embodiment of Formula (II), $A^2$, $B^1$, $D^1$, $E^1$, and $Y^1$ are independently selected H, OH, F, Cl, Br, I, CN, $CF_3$, or $NO_2$. In another embodiment of Formula (II), $A^2$, $B^1$, $D^1$, $E^1$, and $Y^1$ are independently selected H, OH, F, Cl, Br, CN, $CF_3$, or $NO_2$. In another embodiment of Formula (II), $A^1$ is $C(A^2)$; $A^2$ is H; and $B^1$, $D^1$, $E^1$, and $Y^1$ are independently selected H, OH, F, Cl, Br, CN, $CF_3$, or $NO_2$. In another embodiment of Formula (II), $A^1$ is $C(A^2)$; and $A^2$, $B^1$, $D^1$, $Y^1$, and $E^1$ are H. In another embodiment of Formula (II), $A^1$ is $C(A^2)$; $A^2$, $B^1$, $D^1$, and $E^1$ are H; and $Y^1$ is $NO_2$. In another embodiment of Formula (II), $A^1$ is $C(A^2)$; $A^2$, $B^1$, $D^1$, and $E^1$ are H; and $Y^1$ is Br. In another embodiment of Formula (II), $A^1$ is $C(A^2)$; $A^2$, $B^1$, $D^1$, and $E^1$ are H; and $Y^1$ is F. In another embodiment of Formula (II), $A^1$ is $C(A^2)$; $A^2$, $B^1$, $D^1$, and $E^1$ are H; and $Y^1$ is CN. In another embodiment of Formula (II), $A^1$ is $C(A^2)$; $A^2$, $B^1$, $D^1$, and $E^1$ are H; and $Y^1$ is $CF_3$. In another embodiment of Formula (II), $A^1$ is $C(A^2)$; $A^2$, $B^1$, $D^1$, and $E^1$ are H; and $Y^1$ is Cl. In another embodiment of Formula (II), $A^1$ is $C(A^2)$; $A^2$, $D^1$, and $E^1$ are H; $B^1$ is Cl, and $Y^1$ is $NO_2$. In another embodiment of Formula (II), $A^1$ is $C(A^2)$; $Y^1$, $A^2$, $B^1$, and $E^1$ are H; and $D^1$ is Br. In another embodiment of Formula (II), $A^1$ is $C(A^2)$; $Y^1$, $A^2$, $D^1$, and $E^1$ are H; and $B^1$ is Br. In another embodiment of Formula (II), $A^1$ is $C(A^2)$; $Y^1$, $A^2$, $D^1$, and $E^1$ are H; and $B^1$ is $NO_2$. In another embodiment of Formula (II), $A^1$ is $C(A^2)$; $Y^1$, $A^2$, $D^1$, and $E^1$ are H; and $B^1$ is OH. In another embodiment of Formula (II), $A^1$ is $C(A^2)$; $Y^1$, $A^2$, $D^1$, and $E^1$ are H; and $B^1$ is F. In another embodiment of Formula (II), $E^1$ and $Y^1$, together with the atoms to which they are attached, are heteroarene, and $A^2$, $B^1$, and $D^1$ are H. In another embodiment of Formula (II), $Y^1$ and $B^1$, together with the atoms to which they are attached, are benzene, and $A^2$, $D^1$, and $E^1$ are independently selected H. In another embodiment of Formula (II), $E^1$ and $Y^1$, together with the atoms to which they are attached, are benzene and $A^2$, $B^1$, and $D^1$ are H. In another embodiment of Formula (II), $A^2$ and $B^1$, together with the atoms to which they are attached, are heteroarene; and $D^1$, $E^1$, and $Y^1$ are independently selected H, F, Cl, Br, I, or $NO_2$. In another embodiment of Formula (II), $A^2$ and $B^1$, together with the atoms to which they are attached, are cycloalkane; and $D^1$, $E^1$, and $Y^1$ are independently selected H, F, Cl, Br, I, or $NO_2$. In another embodiment of Formula (II), $A^2$ and $B^1$, together with the atoms to which they are attached, are heterocycloalkane; and $D^1$, $E^1$, and $Y^1$ are independently selected H, F, Cl, Br, I, or $NO_2$. In another embodiment of Formula (II), $A^2$ and $B^1$, together with the atoms to which they are attached, are heterocycloalkene; and $D^1$, $E^1$, and $Y^1$ are independently selected H, F, Cl, Br, I, or $NO_2$.

Still another embodiment pertains to compounds having Formula II, which are 2-(benzyloxy)-4-{4-[(4'-chloro-1,1'-biphenyl-2-yl)methyl]piperazin-1-yl}-N-[(3-nitrophenyl)sulfonyl]benzamide;

4-{4-[(4'-chloro-1,1'-biphenyl-2-yl)methyl]piperazin-1-yl}-N-[(3-nitrophenyl)sulfonyl]-2-(2-phenylethoxy)benzamide;

4-{4-[(4'-chloro-1,1'-biphenyl-2-yl)methyl]piperazin-1-yl}-N-[(3-nitrophenyl)sulfonyl]-2-phenoxybenzamide;

4-{4-[(4'-chloro-1,1'-biphenyl-2-yl)methyl]piperazin-1-yl}-2-phenoxy-N-(phenylsulfonyl)benzamide;

4-{4-[(4'-chloro-1,1'-biphenyl-2-yl)methyl]piperazin-1-yl}-N-[(3-nitrophenyl)sulfonyl]-2-(phenylthio)benzamide;

2-(benzylamino)-4-{4-[(4'-chloro-1,1'-biphenyl-2-yl)methyl]piperazin-1-yl}-N-[(3-nitrophenyl)sulfonyl]benzamide;

2-benzyl-4-{4-[(4'-chloro-1,1'-biphenyl-2-yl)methyl]piperazin-1-yl}-N-[(3-nitrophenyl)sulfonyl]benzamide;

4-{4-[(4'-chloro-1,1'-biphenyl-2-yl)methyl]piperazin-1-yl}-N-[(3-nitrophenyl)sulfonyl]-2-(2-phenylethyl)benzamide;

4-{4-[(4'-chloro-1,1'-biphenyl-2-yl)methyl]piperazin-1-yl}-N-[(3-nitrophenyl)sulfonyl]-2-(phenylsulfinyl)benzamide;

4-{4-[(4'-chloro-1,1'-biphenyl-2-yl)methyl]piperazin-1-yl}-N-[(4-nitrophenyl)sulfonyl]-2-phenoxybenzamide;

4-{4-[(4'-chloro-1,1'-biphenyl-2-yl)methyl]piperazin-1-yl}-N-[(3-fluorophenyl)sulfonyl]-2-phenoxybenzamide;

4-{4-[(4'-chloro-1,1'-biphenyl-2-yl)methyl]piperazin-1-yl}-N-[(4-fluorophenyl)sulfonyl]-2-phenoxybenzamide;

4-{4-[(4'-chloro-1,1'-biphenyl-2-yl)methyl]piperazin-1-yl}-2-methoxy-N-[(3-nitrophenyl)sulfonyl]benzamide;

4-{4-[(4'-chloro-1,1'-biphenyl-2-yl)methyl]piperazin-1-yl}-N-[(3-nitrophenyl)sulfonyl]-2-(phenylsulfonyl)benzamide;

4-{4-[(4'-chloro-1,1'-biphenyl-2-yl)methyl]piperazin-1-yl}-N-[(4-chloro-3-nitrophenyl)sulfonyl]-2-phenoxybenzamide;

4-[4-({4'-chloro-3-[2-(dimethylamino)ethoxy]-1,1'-biphenyl-2-yl}methyl)piperazin-1-yl]-2-(1H-indol-4-yloxy)-N-[(3-nitrophenyl)sulfonyl]benzamide;

4-[4-({4'-chloro-3-[2-(dimethylamino)ethoxy]-1,1'-biphenyl-2-yl}methyl)piperazin-1-yl]-2-(1H-indol-4-yloxy)-N-(phenylsulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-(phenylsulfonyl)benzamide;

4-(4-{[2-(4-chlorophenyl)-4,4-dimethylcyclohex-1-en-1-yl]methyl}piperazin-1-yl)-N-[(3-cyanophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-(trifluoromethyl)phenyl]sulfonyl}benzamide;

4-(4-{[2-(4-chlorophenyl)-4,4-dimethylcyclohex-1-en-1-yl]methyl}piperazin-1-yl)-N-[(3-chlorophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-[(3-fluorophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-(2-naphthylsulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-(isoquinolin-5-ylsulfonyl)benzamide;

N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

4-{4-[(4'-chlorobiphenyl-2-yl)methyl]piperazin-1-yl}-N-[(2-chloropyridin-3-yl)sulfonyl]benzamide;

4-{4-[(4'-chlorobiphenyl-2-yl)methyl]piperazin-1-yl}-N-[(7-nitro-1H-benzimidazol-5-yl)sulfonyl]benzamide;

4-{4-[(4'-chlorobiphenyl-2-yl)methyl]piperazin-1-yl}-N-[(3-oxo-3,4-dihydro-2H-1,4-benzoxazin-6-yl)sulfonyl]benzamide;

4-{4-[(4'-chlorobiphenyl-2-yl)methyl]piperazin-1-yl}-N-[(6-chloro-1,1-dioxido-2H-1,2,4-benzothiadiazin-7-yl)sulfonyl]benzamide;

4-{4-[(4'-chlorobiphenyl-2-yl)methyl]piperazin-1-yl}-N-({5-[ethyl(trifluoroacetyl)amino]-1-naphthyl}sulfonyl)benzamide;

4-{4-[(4'-chlorobiphenyl-2-yl)methyl]piperazin-1-yl}-N-[(5,5,8,8-tetramethyl-5,6,7,8-tetrahydronaphthalen-2-yl)sulfonyl]benzamide;

4-{4-[(4'-chlorobiphenyl-2-yl)methyl]piperazin-1-yl}-N-[(2-oxo-2H-chromen-6-yl)sulfonyl]benzamide;

and therapeutically acceptable salts, prodrugs, salts of prodrugs and metabolites thereof.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (III)

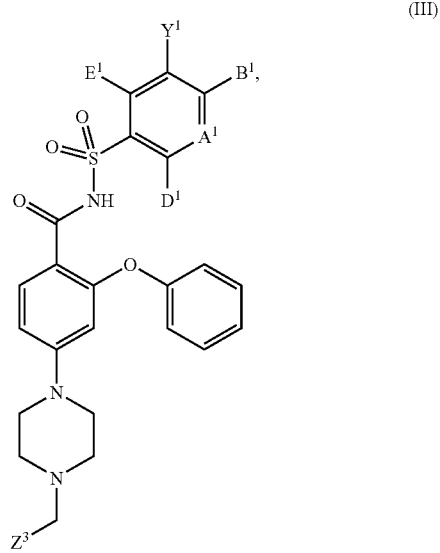

(III)

wherein $A^1$, $B^1$, $D^1$, $E^1$, $Y^1$, and $Z^3$ are as described for Formula (I).

In one embodiment of Formula (III), $A^1$ is N or $C(A^2)$;

$A^2$, $B^1$, $D^1$, $E^1$, and $Y^1$ are independently selected H, OH, F, Cl, Br, I, CN, $CF_3$, or $NO_2$;

or $E^1$ and $Y^1$, together with the atoms to which they are attached, are benzene or heteroarene, and $A^2$, $B^1$, and $D^1$ are independently selected H;

or $Y^1$ and $B^1$, together with the atoms to which they are attached, are benzene, and $A^2$, $D^1$, and $E^1$ are independently selected H;

or $A^2$ and $B^1$, together with the atoms to which they are attached, are heteroarene, cycloalkane, heterocycloalkane or heterocycloalkene; and $D^1$, $E^1$, and $Y^1$ are independently selected H, F, Cl, Br, I, or $NO_2$;

$Z^3$ is $R^{38}$ or $R^{40}$;

$R^{38}$ is phenyl;

$R^{40}$ is cycloalkenyl;

wherein the cyclic moieties represented by E¹ and Y¹ together, Y¹ and B¹ together, A² and B¹ together, R³⁰, R³⁰ᴬ, R³⁷ᴮ, R³⁸, and R⁴⁰ are independently unsubstituted unsubstituted, substituted or further substituted with one or more independently selected R⁵⁷, OR⁵⁷, NR⁵⁷C(O)R⁵⁷, or (O);

R⁵⁷ is R⁵⁸, or R⁶¹;

R⁵⁸ is phenyl,

R⁶¹ is alkyl, which is unsubstituted or substituted with one or two or three independently selected N(R⁶²)₂, or F, Cl, Br or I substituents;

R⁶² is R⁶⁶;

R⁶⁶ is alkyl; and wherein the cyclic moieties represented by R⁵⁸ is unsubstituted or substituted with one or more independently selected F, Cl, Br or I substituents.

In one embodiment of Formula (III), A¹ is C(A²); and A² is H. In another embodiment of Formula (III), A¹ is N.

In another embodiment of Formula (III), A², B¹, D¹, E¹, and Y¹ are independently selected H, OH, F, Cl, Br, I, CN, CF₃, or NO₂. In another embodiment of Formula (III), A², B¹, D¹, E¹, and Y¹ are independently selected H, OH, F, Cl, Br, CN, CF₃, or NO₂. In another embodiment of Formula (III), A¹ is C(A²); A² is H; and B¹, D¹, E¹, and Y¹ are independently selected H, OH, F, Cl, Br, CN, CF₃, or NO₂. In another embodiment of Formula (III), A¹ is C(A²); and A², B¹, D¹, Y¹, and E¹ are H. In another embodiment of Formula (III), A¹ is C(A²); A², B¹, D¹, and E¹ are H; and Y¹ is NO₂. In another embodiment of Formula (III), A¹ is C(A²); A², B¹, D¹, and E¹ are H; and Y¹ is Br. In another embodiment of Formula (III), A¹ is C(A²); A², B¹, D¹, and E¹ are H; and Y¹ is F. In another embodiment of Formula (III), A¹ is C(A²); A², B¹, D¹, and E¹ are H; and Y¹ is CN. In another embodiment of Formula (III), A¹ is C(A²); A², B¹, D¹, and E¹ are H; and Y¹ is CF₃. In another embodiment of Formula (III), A¹ is C(A²); A², B¹, D¹, and E¹ are H; and Y¹ is Cl. In another embodiment of Formula (III), A¹ is C(A²); A², D¹, and E¹ are H; B¹ is Cl, and Y¹ is NO₂. In another embodiment of Formula (III), A¹ is C(A²); Y¹, A², B¹, and E¹ are H; and D¹ is Br. In another embodiment of Formula (III), A¹ is C(A²); Y¹, A², D¹, and E¹ are H; and B¹ is Br. In another embodiment of Formula (III), A¹ is C(A²); Y¹, A², D¹, and E¹ are H; and B¹ is NO₂. In another embodiment of Formula (III), A¹ is C(A²); Y¹, A², D¹, and E¹ are H; and B¹ is OH. In another embodiment of Formula (III), A¹ is C(A²); Y¹, A², D¹, and E¹ are H; and B¹ is F. In another embodiment of Formula (III), E¹ and Y¹, together with the atoms to which they are attached, are heteroarene, and A², B¹, and D¹ are H. In another embodiment of Formula (III), Y¹ and B¹, together with the atoms to which they are attached, are benzene, and A², D¹, and E¹ are independently selected H. In another embodiment of Formula (III), E¹ and Y¹, together with the atoms to which they are attached, are benzene and A², B¹, and D¹ are H. In another embodiment of Formula (III), A² and B¹, together with the atoms to which they are attached, are heteroarene; and D¹, E¹, and Y¹ are independently selected H, F, Cl, Br, I, or NO₂. In another embodiment of Formula (III), A² and B¹, together with the atoms to which they are attached, are cycloalkane; and D¹, E¹, and Y¹ are independently selected H, F, Cl, Br, I, or NO₂. In another embodiment of Formula (III), A² and B¹, together with the atoms to which they are attached, are heterocycloalkane; and D¹, E¹, and Y¹ are independently selected H, F, Cl, Br, I, or NO₂. In another embodiment of Formula (III), A² and B¹, together with the atoms to which they are attached, are heterocycloalkene; and D¹, E¹, and Y¹ are independently selected H, F, Cl, Br, I, or NO₂.

Still another embodiment pertains to compounds having Formula III, which are

4-{4-[(4'-chloro-1,1'-biphenyl-2-yl)methyl]piperazin-1-yl}-N-[(3-nitrophenyl)sulfonyl]-2-phenoxybenzamide;

4-{4-[(4'-chloro-1,1'-biphenyl-2-yl)methyl]piperazin-1-yl}-2-phenoxy-N-(phenylsulfonyl)benzamide;

4-{4-[(4'-chloro-1,1'-biphenyl-2-yl)methyl]piperazin-1-yl}-N-[(4-nitrophenyl)sulfonyl]-2-phenoxybenzamide;

4-{4-[(4'-chloro-1,1'-biphenyl-2-yl)methyl]piperazin-1-yl}-N-[(3-fluorophenyl)sulfonyl]-2-phenoxybenzamide;

4-{4-[(4'-chloro-1,1'-biphenyl-2-yl)methyl]piperazin-1-yl}-N-[(4-fluorophenyl)sulfonyl]-2-phenoxybenzamide;

4-{4-[(4'-chloro-1,1'-biphenyl-2-yl)methyl]piperazin-1-yl}-N-[(4-chloro-3-nitrophenyl)sulfonyl]-2-phenoxybenzamide;

and therapeutically acceptable salts, prodrugs, salts of prodrugs and metabolites thereof.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (IV)

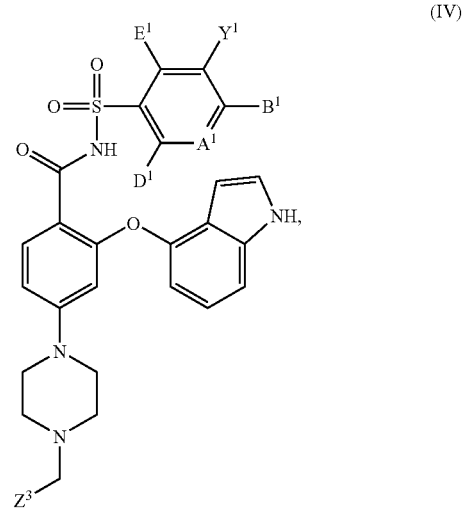

(IV)

wherein A¹, B¹, D¹, E¹, Y¹, and Z³ are as described for Formula (I).

In one embodiment of Formula (IV),

A¹ is N or C(A²);

A², B¹, D¹, E¹, and Y¹ are independently selected H, OH, F, Cl, Br, I, CN, CF₃, or NO₂;

or

E¹ and Y¹, together with the atoms to which they are attached, are benzene or heteroarene, and A², B¹, and D¹ are independently selected H;

or

Y¹ and B¹, together with the atoms to which they are attached, are benzene, and

A², D¹, and E¹ are independently selected H;

or

A² and B¹, together with the atoms to which they are attached, are heteroarene, cycloalkane, heterocycloalkane or heterocycloalkene; and D¹, E¹, and Y¹ are independently selected H, F, Cl, Br, I, or NO₂;

Z³ is R³⁸ or R⁴⁰;

R³⁸ is phenyl;

R⁴⁰ is cycloalkenyl;

wherein the cyclic moieties represented by $E^1$ and $Y^1$ together, $Y^1$ and $B^1$ together, $A^2$ and $B^1$ together, $R^{30}$, $R^{30A}$, $R^{37B}$, $R^{38}$, and $R^{40}$ are independently unsubstituted, further unsubstituted, substituted or further substituted with one or more independently selected $R^{57}$, $OR^{57}$, $NR^{57}C(O)R^{57}$, or (O);

$R^{57}$ is $R^{58}$, or $R^{61}$;

$R^{58}$ is phenyl, $R^{61}$ is alkyl, which is unsubstituted or substituted with one or two or three independently selected $N(R^{62})_2$, or F, Cl, Br or I substituents;

$R^{62}$ is $R^{66}$;

$R^{66}$ is alkyl; and wherein the cyclic moieties represented by $R^{58}$ is unsubstituted or substituted with one or more independently selected F, Cl, Br or I substituents.

In one embodiment of Formula (IV), $A^1$ is $C(A^2)$; and $A^2$ is H. In another embodiment of Formula (IV), $A^1$ is N.

In another embodiment of Formula (IV), $A^2$, $B^1$, $D^1$, $E^1$, and $Y^1$ are independently selected H, OH, F, Cl, Br, I, CN, $CF_3$, or $NO_2$. In another embodiment of Formula (IV), $A^2$, $B^1$, $D^1$, $E^1$, and $Y^1$ are independently selected H, OH, F, Cl, Br, CN, $CF_3$, or $NO_2$. In another embodiment of Formula (IV), $A^1$ is $C(A^2)$; $A^2$ is H; and $B^1$, $D^1$, $E^1$, and $Y^1$ are independently selected H, OH, F, Cl, Br, CN, $CF_3$, or $NO_2$. In another embodiment of Formula (IV), $A^1$ is $C(A^2)$; and $A^2$, $B^1$, $D^1$, $Y^1$, and $E^1$ are H. In another embodiment of Formula (IV), $A^1$ is $C(A^2)$; $A^2$, $B^1$, $D^1$, and $E^1$ are H; and $Y^1$ is $NO_2$. In another embodiment of Formula (IV), $A^1$ is $C(A^2)$; $A^2$, $B^1$, $D^1$, and $E^1$ are H; and $Y^1$ is Br. In another embodiment of Formula (IV), $A^1$ is $C(A^2)$; $A^2$, $B^1$, $D^1$, and $E^1$ are H; and $Y^1$ is F. In another embodiment of Formula (IV), $A^1$ is $C(A^2)$; $A^2$, $B^1$, $D^1$, and $E^1$ are H; and $Y^1$ is CN. In another embodiment of Formula (IV), $A^1$ is $C(A^2)$; $A^2$, $B^1$, $D^1$, and $E^1$ are H; and $Y^1$ is $CF_3$. In another embodiment of Formula (IV), $A^1$ is $C(A^2)$; $A^2$, $B^1$, $D^1$, and $E^1$ are H; and $Y^1$ is Cl. In another embodiment of Formula (IV), $A^1$ is $C(A^2)$; $A^2$, $D^1$, and $E^1$ are H; $B^1$ is Cl, and $Y^1$ is $NO_2$. In another embodiment of Formula (IV), $A^1$ is $C(A^2)$; $Y^1$, $A^2$, $B^1$, and $E^1$ are H; and $D^1$ is Br. In another embodiment of Formula (IV), $A^1$ is $C(A^2)$; $Y^1$, $A^2$, $D^1$, and $E^1$ are H; and $B^1$ is Br. In another embodiment of Formula (IV), $A^1$ is $C(A^2)$; $Y^1$, $A^2$, $D^1$, and $E^1$ are H; and $B^1$ is $NO_2$. In another embodiment of Formula (IV), $A^1$ is $C(A^2)$; $Y^1$, $A^2$, $D^1$, and $E^1$ are H; and $B^1$ is OH. In another embodiment of Formula (IV), $A^1$ is $C(A^2)$; $Y^1$, $A^2$, $D^1$, and $E^1$ are H; and $B^1$ is F. In another embodiment of Formula (IV), $E^1$ and $Y^1$, together with the atoms to which they are attached, are heteroarene, and $A^2$, $B^1$, and $D^1$ are H. In another embodiment of Formula (IV), $Y^1$ and $B^1$, together with the atoms to which they are attached, are benzene, and $A^2$, $D^1$, and $E^1$ are independently selected H. In another embodiment of Formula (IV), $E^1$ and $Y^1$, together with the atoms to which they are attached, are benzene and $A^2$, $B^1$, and $D^1$ are H. In another embodiment of Formula (IV), $A^2$ and $B^1$, together with the atoms to which they are attached, are heteroarene; and $D^1$, $E^1$, and $Y^1$ are independently selected H, F, Cl, Br, I, or $NO_2$. In another embodiment of Formula (IV), $A^2$ and $B^1$, together with the atoms to which they are attached, are cycloalkane; and $D^1$, $E^1$, and $Y^1$ are independently selected H, F, Cl, Br, I, or $NO_2$. In another embodiment of Formula (IV), $A^2$ and $B^1$, together with the atoms to which they are attached, are heterocycloalkane; and $D^1$, $E^1$, and $Y^1$ are independently selected H, F, Cl, Br, I, or $NO_2$. In another embodiment of Formula (IV), $A^2$ and $B^1$, together with the atoms to which they are attached, are heterocycloalkene; and $D^1$, $E^1$, and $Y^1$ are independently selected H, F, Cl, Br, I, or $NO_2$.

Still another embodiment pertains to compounds having Formula IV, which are

4-[4-({4'-chloro-3-[2-(dimethylamino)ethoxy]-1,1'-biphenyl-2-yl}methyl)piperazin-1-yl]-2-(1H-indol-4-yloxy)-N-[(3-nitrophenyl)sulfonyl]benzamide;

4-[4-({4'-chloro-3-[2-(dimethylamino)ethoxy]-1,1'-biphenyl-2-yl}methyl)piperazin-1-yl]-2-(1H-indol-4-yloxy)-N-(phenylsulfonyl)benzamide;

and therapeutically acceptable salts, prodrugs, salts of prodrugs and metabolites thereof.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (V)

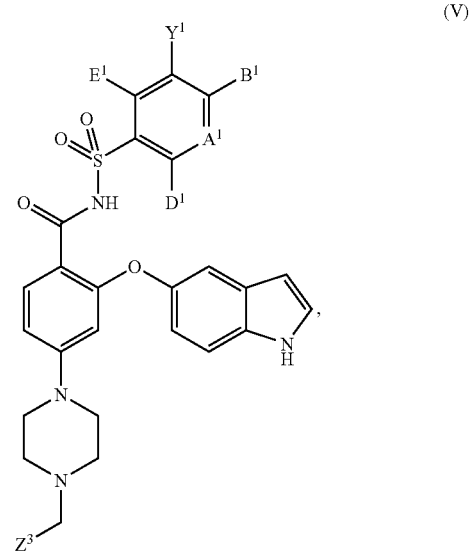

wherein $A^1$, $B^1$, $D^1$, $E^1$, $Y^1$, and $Z^3$ are as described for Formula (I).

In one embodiment of Formula (V), $A^1$ is N or $C(A^2)$;

$A^2$, $B^1$, $D^1$, $E^1$, and $Y^1$ are independently selected H, OH, F, Cl, Br, I, CN, $CF_3$, or $NO_2$;

or $E^1$ and $Y^1$, together with the atoms to which they are attached, are benzene or heteroarene, and $A^2$, $B^1$, and $D^1$ are independently selected H;

or $Y^1$ and $B^1$, together with the atoms to which they are attached, are benzene, and $A^2$, $D^1$, and $E^1$ are independently selected H;

or $A^2$ and $B^1$, together with the atoms to which they are attached, are heteroarene, cycloalkane, heterocycloalkane or heterocycloalkene; and $D^1$, $E^1$, and $Y^1$ are independently selected H, F, Cl, Br, I, or $NO_2$;

$Z^3$ is $R^{38}$ or $R^{40}$;

$R^{38}$ is phenyl;

$R^{40}$ is cycloalkenyl;

wherein the cyclic moieties represented by $E^1$ and $Y^1$ together, $Y^1$ and $B^1$ together, $A^2$ and $B^1$ together, $R^{30}$, $R^{30A}$, $R^{37B}$, $R^{38}$, and $R^{40}$ are independently unsubstituted, further unsubstituted, substituted or further substituted with one or more independently selected $R^{57}$, $OR^{57}$, $NR^{57}C(O)R^{57}$, or (O);

$R^{57}$ is $R^{58}$, or $R^{61}$;

$R^{58}$ is phenyl, $R^{61}$ is alkyl, which is unsubstituted or substituted with one or two or three independently selected $N(R^{62})_2$, or F, Cl, Br or I substituents;

$R^{62}$ is $R^{66}$;

$R^{66}$ is alkyl; and wherein the cyclic moieties represented by $R^{58}$ is unsubstituted or substituted with one or more independently selected F, Cl, Br or I substituents.

In one embodiment of Formula (V), $A^1$ is $C(A^2)$; and $A^2$ is H. In another embodiment of Formula (V), $A^1$ is N.

In another embodiment of Formula (V), $A^2$, $B^1$, $D^1$, $E^1$, and $Y^1$ are independently selected H, OH, F, Cl, Br, I, CN, $CF_3$, or $NO_2$. In another embodiment of Formula (V), $A^2$, $B^1$, $D^1$, $E^1$, and $Y^1$ are independently selected H, OH, F, Cl, Br, CN, $CF_3$, or $NO_2$. In another embodiment of Formula (V), $A^1$ is $C(A^2)$; $A^2$ is H; and $B^1$, $D^1$, $E^1$, and $Y^1$ are independently selected H, OH, F, Cl, Br, CN, $CF_3$, or $NO_2$. In another embodiment of Formula (V), $A^1$ is $C(A^2)$; and $A^2$, $B^1$, $D^1$, $Y^1$, and $E^1$ are H. In another embodiment of Formula (V), $A^1$ is $C(A^2)$; $A^2$, $B^1$, $D^1$, and $E^1$ are H; and $Y^1$ is $NO_2$. In another embodiment of Formula (V), $A^1$ is $C(A^2)$; $A^2$, $B^1$, $D^1$, and $E^1$ are H; and $Y^1$ is Br. In another embodiment of Formula (V), $A^1$ is $C(A^2)$; $A^2$, $B^1$, $D^1$, and $E^1$ are H; and $Y^1$ is F. In another embodiment of Formula (V), $A^1$ is $C(A^2)$; $A^2$, $B^1$, $D^1$, and $E^1$ are H; and $Y^1$ is CN. In another embodiment of Formula (V), $A^1$ is $C(A^2)$; $A^2$, $B^1$, $D^1$, and $E^1$ are H; and $Y^1$ is $CF_3$. In another embodiment of Formula (V), $A^1$ is $C(A^2)$; $A^2$, $B^1$, $D^1$, and $E^1$ are H; and $Y^1$ is Cl. In another embodiment of Formula (V), $A^1$ is $C(A^2)$; $A^2$, $D^1$, and $E^1$ are H; $B^1$ is Cl, and $Y^1$ is $NO_2$. In another embodiment of Formula (V), $A^1$ is $C(A^2)$; $Y^1$, $A^2$, $B^1$, and $E^1$ are H; and $D^1$ is Br. In another embodiment of Formula (V), $A^1$ is $C(A^2)$; $Y^1$, $A^2$, $D^1$, and $E^1$ are H; and $B^1$ is Br. In another embodiment of Formula (V), $A^1$ is $C(A^2)$; $Y^1$, $A^2$, $D^1$, and $E^1$ are H; and $B^1$ is $NO_2$. In another embodiment of Formula (V), $A^1$ is $C(A^2)$; $Y^1$, $A^2$, $D^1$, and $E^1$ are H; and $B^1$ is OH. In another embodiment of Formula (V), $A^1$ is $C(A^2)$; $Y^1$, $A^2$, $D^1$, and $E^1$ are H; and $B^1$ is F. In another embodiment of Formula (V), $E^1$ and $Y^1$, together with the atoms to which they are attached, are heteroarene, and $A^2$, $B^1$, and $D^1$ are H. In another embodiment of Formula (V), $Y^1$ and $B^1$, together with the atoms to which they are attached, are benzene, and $A^2$, $D^1$, and $E^1$ are independently selected H. In another embodiment of Formula (V), $E^1$ and $Y^1$, together with the atoms to which they are attached, are benzene and $A^2$, $B^1$, and $D^1$ are H. In another embodiment of Formula (V), $A^2$ and $B^1$, together with the atoms to which they are attached, are heteroarene; and $D^1$, $E^1$, and $Y^1$ are independently selected H, F, Cl, Br, I, or $NO_2$. In another embodiment of Formula (V), $A^2$ and $B^1$, together with the atoms to which they are attached, are cycloalkane; and $D^1$, $E^1$, and $Y^1$ are independently selected H, F, Cl, Br, I, or $NO_2$. In another embodiment of Formula (V), $A^2$ and $B^1$, together with the atoms to which they are attached, are heterocycloalkane; and $D^1$, $E^1$, and $Y^1$ are independently selected H, F, Cl, Br, I, or $NO_2$. In another embodiment of Formula (V), $A^2$ and $B^1$, together with the atoms to which they are attached, are heterocycloalkene; and $D^1$, $E^1$, and $Y^1$ are independently selected H, F, Cl, Br, I, or $NO_2$.

Still another embodiment pertains to compounds having Formula V, which are 4-(4-{[2-(4-chlorophenyl)-4,4-dimethylcyclohex-1-en-1-yl]methyl}piperazin-1-yl)-2-(1H-indol-5-yloxy)-N-[(3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-(phenylsulfonyl)benzamide;

4-(4-{[2-(4-chlorophenyl)-4,4-dimethylcyclohex-1-en-1-yl]methyl}piperazin-1-yl)-N-[(3-cyanophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-(trifluoromethyl)phenyl]sulfonyl}benzamide;

4-(4-{[2-(4-chlorophenyl)-4,4-dimethylcyclohex-1-en-1-yl]methyl}piperazin-1-yl)-N-[(3-chlorophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-[(3-fluorophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-(2-naphthylsulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-(isoquinolin-5-ylsulfonyl)benzamide;

and therapeutically acceptable salts, prodrugs, salts of prodrugs and metabolites thereof.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (VI)

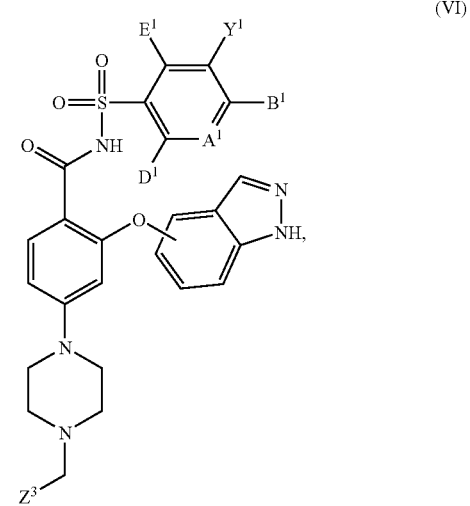

(VI)

wherein $A^1$, $B^1$, $D^1$, $E^1$, $Y^1$, and $Z^3$ are as described for Formula (I).

In one embodiment of Formula (VI), $A^1$ is N or $C(A^2)$;

$A^2$, $B^1$, $D^1$, $E^1$, and $Y^1$ are independently selected H, OH, F, Cl, Br, I, CN, $CF_3$, or $NO_2$;

or $E^1$ and $Y^1$, together with the atoms to which they are attached, are benzene or heteroarene, and $A^2$, $B^1$, and $D^1$ are independently selected H;

or $Y^1$ and $B^1$, together with the atoms to which they are attached, are benzene, and $A^2$, $D^1$, and $E^1$ are independently selected H;

or $A^2$ and $B^1$, together with the atoms to which they are attached, are heteroarene, cycloalkane, heterocycloalkane or heterocycloalkene; and $D^1$, $E^1$, and $Y^1$ are independently selected H, F, Cl, Br, I, or $NO_2$;

$Z^3$ is $R^{38}$ or $R^{40}$;

$R^{38}$ is phenyl;

$R^{40}$ is cycloalkenyl;

wherein the cyclic moieties represented by $E^1$ and $Y^1$ together, $Y^1$ and $B^1$ together, $A^2$ and $B^1$ together, $R^{30}$, $R^{30A}$, $R^{37B}$, $R^{38}$, and $R^{40}$ are independently unsubstituted, further unsubstituted, substituted or further substituted with one or more independently selected $R^{57}$, $OR^{57}$, $NR^{57}C(O)R^{57}$, or (O);

$R^{57}$ is $R^{58}$, or $R^{61}$;

$R^{58}$ is phenyl, $R^{61}$ is alkyl, which is unsubstituted or substituted with one or two or three independently selected $N(R^{62})_2$, or F, Cl, Br or I substituents;

$R^{62}$ is $R^{66}$;

$R^{66}$ is alkyl; and wherein the cyclic moieties represented by $R^{58}$ is unsubstituted or substituted with one or more independently selected F, Cl, Br or I substituents.

In one embodiment of Formula (VI), $A^1$ is $C(A^2)$; and $A^2$ is H. In another embodiment of Formula (VI), $A^1$ is N.

In another embodiment of Formula (VI), $A^2$, $B^1$, $D^1$, $E^1$, and $Y^1$ are independently selected H, OH, F, Cl, Br, I, CN, $CF_3$, or $NO_2$. In another embodiment of Formula (VI), $A^2$, $B^1$, $D^1$, $E^1$, and $Y^1$ are independently selected H, OH, F, Cl, Br, CN, $CF_3$, or $NO_2$. In another embodiment of Formula (VI), $A^1$ is $C(A^2)$; $A^2$ is H; and $B^1$, $D^1$, $E^1$, and $Y^1$ are independently selected H, OH, F, Cl, Br, CN, $CF_3$, or $NO_2$. In another embodiment of Formula (VI), $A^1$ is $C(A^2)$; and $A^2$, $B^1$, $D^1$, $Y^1$, and $E^1$ are H. In another embodiment of Formula (VI), $A^1$ is $C(A^2)$; $A^2$, $B^1$, $D^1$, and $E^1$ are H; and $Y^1$ is $NO_2$. In another embodiment of Formula (VI), $A^1$ is $C(A^2)$; $A^2$, $B^1$, $D^1$, and $E^1$ are H; and $Y^1$ is Br. In another embodiment of Formula (VI), $A^1$ is $C(A^2)$; $A^2$, $B^1$, $D^1$, and $E^1$ are H; and $Y^1$ is F. In another embodiment of Formula (VI), $A^1$ is $C(A^2)$; $A^2$, $B^1$, $D^1$, and $E^1$ are H; and $Y^1$ is CN. In another embodiment of Formula (VI), $A^1$ is $C(A^2)$; $A^2$, $B^1$, $D^1$, and $E^1$ are H; and $Y^1$ is $CF_3$. In another embodiment of Formula (VI), $A^1$ is $C(A^2)$; $A^2$, $B^1$, $D^1$, and $E^1$ are H; and $Y^1$ is Cl. In another embodiment of Formula (VI), $A^1$ is $C(A^2)$; $A^2$, $D^1$, and $E^1$ are H; $B^1$ is Cl, and $Y^1$ is $NO_2$. In another embodiment of Formula (VI), $A^1$ is $C(A^2)$; $Y^1$, $A^2$, $B^1$, and $E^1$ are H; and $D^1$ is Br. In another embodiment of Formula (VI), $A^1$ is $C(A^2)$; $Y^1$, $A^2$, $D^1$, and $E^1$ are H; and $B^1$ is Br. In another embodiment of Formula (VI), $A^1$ is $C(A^2)$; $Y^1$, $A^2$, $D^1$, and $E^1$ are H; and $B^1$ is $NO_2$. In another embodiment of Formula (VI), $A^1$ is $C(A^2)$; $Y^1$, $A^2$, $D^1$, and $E^1$ are H; and $B^1$ is OH. In another embodiment of Formula (VI), $A^1$ is $C(A^2)$; $Y^1$, $A^2$, $D^1$, and $E^1$ are H; and $B^1$ is F. In another embodiment of Formula (VI), $E^1$ and $Y^1$, together with the atoms to which they are attached, are heteroarene, and $A^2$, $B^1$, and $D^1$ are H. In another embodiment of Formula (VI), $Y^1$ and $B^1$, together with the atoms to which they are attached, are benzene, and $A^2$, $D^1$, and $E^1$ are independently H. In another embodiment of Formula (VI), $E^1$ and $Y^1$, together with the atoms to which they are attached, are benzene and $A^2$, $B^1$, and $D^1$ are H. In another embodiment of Formula (VI), $A^2$ and $B^1$, together with the atoms to which they are attached, are heteroarene; and $D^1$, $E^1$, and $Y^1$ are independently selected H, F, Cl, Br, I, or $NO_2$. In another embodiment of Formula (VI), $A^2$ and $B^1$, together with the atoms to which they are attached, are cycloalkane; and $D^1$, $E^1$, and $Y^1$ are independently selected H, F, Cl, Br, I, or $NO_2$. In another embodiment of Formula (VI), $A^2$ and $B^1$, together with the atoms to which they are attached, are heterocycloalkane; and $D^1$, $E^1$, and $Y^1$ are independently selected H, F, Cl, Br, I, or $NO_2$. In another embodiment of Formula (VI), $A^2$ and $B^1$, together with the atoms to which they are attached, are heterocycloalkene; and $D^1$, $E^1$, and $Y^1$ are independently selected H, F, Cl, Br, I, or $NO_2$.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (VII)

(VII)

wherein $A^1$, $B^1$, $D^1$, $E^1$, $Y^1$, and $Z^3$ are as described for Formula (I).

In one embodiment of Formula (VII), $A^1$ is N or $C(A^2)$;

$A^2$, $B^1$, $D^1$, $E^1$, and $Y^1$ are independently selected H, OH, F, Cl, Br, I, CN, $CF_3$, or $NO_2$;

or $E^1$ and $Y^1$, together with the atoms to which they are attached, are benzene or heteroarene, and $A^2$, $B^1$, and $D^1$ are independently selected H;

or $Y^1$ and $B^1$, together with the atoms to which they are attached, are benzene, and $A^2$, $D^1$, and $E^1$ are independently selected H;

or $A^2$ and $B^1$, together with the atoms to which they are attached, are heteroarene, cycloalkane, heterocycloalkane or heterocycloalkene; and $D^1$, $E^1$, and $Y^1$ are independently selected H, F, Cl, Br, I, or $NO_2$;

$Z^3$ is $R^{38}$ or $R^{40}$;

$R^{38}$ is phenyl;

$R^{40}$ is cycloalkenyl;

wherein the cyclic moieties represented by $E^1$ and $Y^1$ together, $Y^1$ and $B^1$ together, $A^2$ and $B^1$ together, $R^{30}$, $R^{30A}$, $R^{37B}$, $R^{38}$, and $R^{40}$ are independently unsubstituted, further unsubstituted, substituted or further substituted with one or more independently selected $R^{57}$, $OR^{57}$, $NR^{57}C(O)R^{57}$, or (O);

$R^{57}$ is $R^{58}$, or $R^{61}$;

$R^{58}$ is phenyl, $R^{61}$ is alkyl, which is unsubstituted or substituted with one or two or three independently selected $N(R^{62})_2$, or F, Cl, Br or I substituents;

$R^{62}$ is $R^{66}$;

$R^{66}$ is alkyl; and wherein the cyclic moieties represented by $R^{58}$ is unsubstituted or substituted with one or more independently selected F, Cl, Br or I substituents.

In one embodiment of Formula (VII), $A^1$ is $C(A^2)$; and $A^2$ is H. In another embodiment of Formula (VII), $A^1$ is N.

In another embodiment of Formula (VII), $A^2$, $B^1$, $D^1$, $E^1$, and $Y^1$ are independently selected H, OH, F, Cl, Br, I, CN, $CF_3$, or $NO_2$. In another embodiment of Formula (VII), $A^2$, $B^1$, $D^1$, $E^1$, and $Y^1$ are independently selected H, OH, F, Cl, Br, CN, $CF_3$, or $NO_2$. In another embodiment of Formula (VII), $A^1$ is $C(A^2)$; $A^2$ is H; and $B^1$, $D^1$, $E^1$, and $Y^1$ are independently selected H, OH, F, Cl, Br, CN, $CF_3$, or $NO_2$. In another embodiment of Formula (VII), $A^1$ is $C(A^2)$; and $A^2$, $B^1$, $D^1$, $Y^1$, and $E^1$ are H. In another embodiment of Formula (VII), $A^1$ is $C(A^2)$; $A^2$, $B^1$, $D^1$, and $E^1$ are H; and $Y^1$ is $NO_2$. In another embodiment of Formula (VII), $A^1$ is $C(A^2)$; $A^2$, $B^1$, $D^1$, and $E^1$ are H; and $Y^1$ is Br. In another embodiment of Formula (VII), $A^1$ is $C(A^2)$; $A^2$, $B^1$, $D^1$, and $E^1$ are H; and $Y^1$ is F. In another embodiment of Formula (VII), $A^1$ is $C(A^2)$; $A^2$, $B^1$, $D^1$, and $E^1$ are H; and $Y^1$ is CN. In another embodiment of Formula (VII), $A^1$ is $C(A^2)$; $A^2$, $B^1$, $D^1$, and $E^1$ are H; and $Y^1$ is $CF_3$. In another embodiment of Formula (VII), $A^1$ is $C(A^2)$; $A^2$, $B^1$, $D^1$, and $E^1$ are H; and $Y^1$ is Cl. In another embodiment of Formula (VII), $A^1$ is $C(A^2)$; $A^2$, $D^1$, and $E^1$ are H; $B^1$ is Cl, and $Y^1$ is $NO_2$. In another embodiment of Formula (VII), $A^1$ is $C(A^2)$; $Y^1$, $A^2$, $B^1$, and $E^1$ are H; and $D^1$ is Br. In another embodiment of Formula (VII), $A^1$ is $C(A^2)$; $Y^1$, $A^2$, $D^1$, and $E^1$ are H; and $B^1$ is Br. In another embodiment of Formula (VII), $A^1$ is $C(A^2)$; $Y^1$, $A^2$, $D^1$, and $E^1$ are H; and $B^1$ is $NO_2$. In another embodiment of Formula (VII), $A^1$ is $C(A^2)$; $Y^1$, $A^2$, $D^1$, and $E^1$ are H; and $B^1$ is OH. In another embodiment of Formula (VII), $A^1$ is $C(A^2)$; $Y^1$, $A^2$, $D^1$, and $E^1$ are H; and $B^1$ is F. In another embodiment of Formula (VII), $E^1$ and $Y^1$, together with the atoms to which they are attached, are heteroarene, and $A^2$, $B^1$, and $D^1$ are H. In another embodiment of Formula (VII), $Y^1$ and $B^1$, together with the atoms to which they are attached, are benzene, and $A^2$, $D^1$, and $E^1$ are independently selected H. In another embodiment of Formula (VII), $E^1$ and $Y^1$, together with the atoms to which they are attached, are benzene and $A^2$, $B^1$, and $D^1$ are H. In another embodiment of Formula (VII), $A^2$ and $B^1$, together with the atoms to which they are attached, are heteroarene; and $D^1$, $E^1$, and $Y^1$ are independently selected H, F, Cl, Br, I, or $NO_2$. In another embodiment of Formula (VII), $A^2$ and $B^1$, together with the atoms to which they are attached, are cycloalkane; and $D^1$, $E^1$, and $Y^1$ are independently selected H, F, Cl, Br, I, or $NO_2$. In another embodiment of Formula (VII), $A^2$ and $B^1$, together with the atoms to which they are attached, are heterocycloalkane; and $D^1$, $E^1$, and $Y^1$ are independently selected H, F, Cl, Br, I, or $NO_2$. In another embodiment of Formula (VII), $A^2$ and $B^1$, together with the atoms to which they are attached, are heterocycloalkene; and $D^1$, $E^1$, and $Y^1$ are independently selected H, F, Cl, Br, I, or $NO_2$.

Another embodiment of this invention pertains to compounds or therapeutically acceptable salts, prodrugs, metabolites, or salts of prodrugs thereof, which are useful as inhibitors of anti-apoptotic Bcl-2 proteins, the compounds having Formula (VIII)

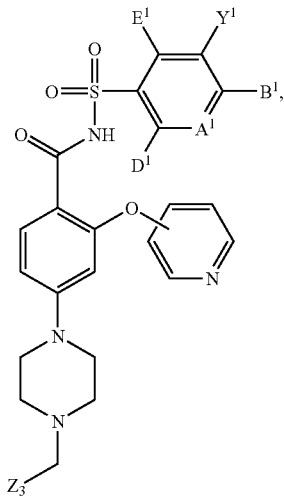

(VIII)

wherein $A^1$, $B^1$, $D^1$, $E^1$, $Y^1$, and $Z^3$ are as described for Formula (I).

In one embodiment of Formula (VIII), $A^1$ is N or $C(A^2)$;

$A^2$, $B^1$, $D^1$, $E^1$, and $Y^1$ are independently selected H, OH, F, Cl, Br, I, CN, $CF_3$, or $NO_2$;

or $E^1$ and $Y^1$, together with the atoms to which they are attached, are benzene or heteroarene, and $A^2$, $B^1$, and $D^1$ are independently selected H;

or $Y^1$ and $B^1$, together with the atoms to which they are attached, are benzene, and $A^2$, $D^1$, and $E^1$ are independently selected H;

or $A^2$ and $B^1$, together with the atoms to which they are attached, are heteroarene, cycloalkane, heterocycloalkane or heterocycloalkene; and $D^1$, $E^1$, and $Y^1$ are independently selected H, F, Cl, Br, I, or $NO_2$;

$Z^3$ is $R^{38}$ or $R^{40}$;

$R^{38}$ is phenyl;

$R^{40}$ is cycloalkenyl;

wherein the cyclic moieties represented by $E^1$ and $Y^1$ together, $Y^1$ and $B^1$ together, $A^2$ and $B^1$ together, $R^{30}$, $R^{30A}$, $R^{37B}$, $R^{38}$, and $R^{40}$ are independently unsubstituted, further unsubstituted, substituted or further substituted with one or more independently selected $R^{57}$, $OR^{57}$, $NR^{57}C(O)R^{57}$, or (O);

$R^{57}$ is $R^{58}$, or $R^{61}$;

$R^{58}$ is phenyl, $R^{61}$ is alkyl, which is unsubstituted or substituted with one or two or three independently selected $N(R^{62})_2$, or F, Cl, Br or I substituents;

$R^{62}$ is $R^{66}$;

$R^{66}$ is alkyl; and wherein the cyclic moieties represented by $R^{58}$ is unsubstituted or substituted with one or more independently selected F, Cl, Br or I substituents.

In one embodiment of Formula (VIII), $A^1$ is $C(A^2)$; and $A^2$ is H. In another embodiment of Formula (VIII), $A^1$ is N.

In another embodiment of Formula (VIII), $A^2$, $B^1$, $D^1$, $E^1$, and $Y^1$ are independently selected H, OH, F, Cl, Br, I, CN, $CF_3$, or $NO_2$. In another embodiment of Formula (VIII), $A^2$, $B^1$, $D^1$, $E^1$, and $Y^1$ are independently selected H, OH, F, Cl, Br, CN, CF$_3$, or NO$_2$. In another embodiment of Formula (VIII), A$^1$ is C(A$^2$); A$^2$ is H; and B$^1$, D$^1$, E$^1$, and Y$^1$ are independently selected H, OH, F, Cl, Br, CN, CF$_3$, or NO$_2$. In another embodiment of Formula (VIII), A$^1$ is C(A$^2$); and A$^2$, B$^1$, D$^1$, Y$^1$, and E$^1$ are H. In another embodiment of Formula (VIII), A$^1$ is C(A$^2$); A$^2$, B$^1$, D$^1$, and E$^1$ are H; and Y$^1$ is NO$_2$. In another embodiment of Formula (VIII), A$^1$ is C(A$^2$); A$^2$, B$^1$, D$^1$, and E$^1$ are H; and Y$^1$ is Br. In another embodiment of Formula (VIII), A$^1$ is C(A$^2$); A$^2$, B$^1$, D$^1$, and E$^1$ are H; and Y$^1$ is F. In another embodiment of Formula (VIII), A$^1$ is C(A$^2$); A$^2$, B$^1$, D$^1$, and E$^1$ are H; and Y$^1$ is CN. In another embodiment of Formula (VIII), A$^1$ is C(A$^2$); A$^2$, B$^1$, D$^1$, and E$^1$ are H; and Y$^1$ is CF$_3$. In another embodiment of Formula (VIII), A$^1$ is C(A$^2$); A$^2$, B$^1$, D$^1$, and E$^1$ are H; and Y$^1$ is Cl. In another embodiment of Formula (VIII), A$^1$ is C(A$^2$); A$^2$, D$^1$, and E$^1$ are H; B$^1$ is Cl, and Y$^1$ is NO$_2$. In another embodiment of Formula (VIII), A$^1$ is C(A$^2$); Y$^1$, A$^2$, B$^1$, and E$^1$ are H; and D$^1$ is Br. In another embodiment of Formula (VIII), A$^1$ is C(A$^2$); Y$^1$, A$^2$, D$^1$, and E$^1$ are H; and B$^1$ is Br. In another embodiment of Formula (VIII), A$^1$ is C(A$^2$); Y$^1$, A$^2$, D$^1$, and E$^1$ are H; and B$^1$ is NO$_2$. In another embodiment of Formula (VIII), A$^1$ is C(A$^2$); Y$^1$, A$^2$, D$^1$, and E$^1$ are H; and B$^1$ is OH. In another embodiment of Formula (VIII), A$^1$ is C(A$^2$); Y$^1$, A$^2$, D$^1$, and E$^1$ are H; and B$^1$ is F. In another embodiment of Formula (VIII), E$^1$ and Y$^1$, together with the atoms to which they are attached, are heteroarene, and A$^2$, B$^1$, and D$^1$ are H. In another embodiment of Formula (VIII), Y$^1$ and B$^1$, together with the atoms to which they are attached, are benzene, and A$^2$, D$^1$, and E$^1$ are independently selected H. In another embodiment of Formula (VIII), E$^1$ and Y$^1$, together with the atoms to which they are attached, are benzene and A$^2$, B$^1$, and D$^1$ are H. In another embodiment of Formula (VIII), A$^2$ and B$^1$, together with the atoms to which they are attached, are heteroarene; and D$^1$, E$^1$, and Y$^1$ are independently selected H, F, Cl, Br, I, or NO$_2$. In another embodiment of Formula (VIII), A$^2$ and B$^1$, together with the atoms to which they are attached, are cycloalkane; and D$^1$, E$^1$, and Y$^1$ are independently selected H, F, Cl, Br, I, or NO$_2$. In another embodiment of Formula (VIII), A$^2$ and B$^1$, together with the atoms to which they are attached, are heterocycloalkane; and D$^1$, E$^1$, and Y$^1$ are independently selected H, F, Cl, Br, I, or NO$_2$. In another embodiment of Formula (VIII), A$^2$ and B$^1$, together with the atoms to which they are attached, are heterocycloalkene; and D$^1$, E$^1$, and Y$^1$ are independently selected H, F, Cl, Br, I, or NO$_2$.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment comprises methods of treating autoimmune disease in a mammal comprising administering thereto a therapeutically acceptable amount of a compound having Formula (I).

Still another embodiment pertains to compositions for treating diseases during which anti-apoptotic Bcl-2 proteins are expressed, said compositions comprising an excipient and a therapeutically effective amount of the compound having Formula (I).

Still another embodiment pertains to methods of treating disease in a patient during which anti-apoptotic Bcl-2 proteins are expressed, said methods comprising administering to the patient a therapeutically effective amount of a compound having Formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having Formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having Formula (I).

Still another embodiment pertains to compositions for treating diseases during which are expressed anti-apoptotic Bcl-2 proteins, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which are expressed anti-apoptotic Bcl-2 proteins, said methods comprising administering to the patient a therapeutically effective amount of a compound having Formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound having Formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with anti-apoptotic Bcl-2 proteins.

Certain precursor compounds which may be metabolized in vitro or in vivo to form compounds having Formula (I) may also have utility for treating diseases associated with expression of anti-apoptotic Bcl-2 proteins.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds and prodrugs thereof are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl) amino)-3-((trifluoromethyl)sulfonyl)benzenesulfonamide) or ABT-737 (i.e., N-(4-(4-((4'-chloro(1,1'-biphenyl)-2-yl) methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (*Bacillus* Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula (I) as binders to and inhibitors of anti-apoptotic Bcl-2 proteins was performed using the Time Resolved-Fluorescence Resonance Energy Transfer (TR-FRET) Assay. Tb-anti-GST antibody was purchased from Invitrogen (Catalog No. PV4216).

Probe Synthesis

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine were obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp (tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif. The peptide synthesis resin (Fmoc-Rink amide MBHA resin) and Fmoc-Lys(Mtt)-OH were obtained from Novabiochem, San Diego, Calif. Single-isomer 6-carboxyfluorescein succinimidyl ester (6-FAM-NHS) was obtained from Anaspec. Trifluoroacetic acid (TFA) was obtained from Oakwood Products, West Columbia, S.C. Thioanisole, phenol, triisopropylsilane (TIS), 3,6-dioxa-1,8-octanedithiol (DODT) and isopropanol were obtained from Aldrich Chemical Co., Milwaukee, Wis. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, Calif.) in both positive and negative ion mode.

General Procedure for Solid-Phase Peptide Synthesis (SPPS)

Peptides were synthesized with, at most, 250 µmol preloaded Wang resin/vessel on an ABI 433A peptide synthesizer using 250 µmol scale FASTMOC™ coupling cycles. Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with dichloromethane and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of N,N-dimethylformamide was flowed through the bed over 15 minutes. The resin was then washed thrice with N,N-dimethylformamide and filtered. Ninhydrin tests showed a strong signal for primary amine Resin Labeling with 6-Carboxyfluorescein-NHS (6-FAM-NHS)

The resin was treated with 2 equivalents 6-FAM-NHS in 1% DIEA/N,N-dimethylformamide and stirred or shaken at ambient temperature overnight. When complete, the resin was drained, washed thrice with N,N-dimethylformamide, thrice with (1×DCM and 1×methanol) and dried to provide an orange resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 µm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D CHEMSTATION software version A.03.04 (Hewlett-Packard. Palo Alto, CA) on a 4.6×250 mm YMC column packed with ODS-AQ 5 µm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.

F-Bak: Peptide Probe
Acetyl-GQVGRQLAIIGDK(6-FAM)INR-NH$_2$ (SEQ ID NO:1)

Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product as an orange solid (0.37 g). This product was purified by RP-HPLC. Fractions across the main peak were tested by analytical RP-HPLC, and the pure fractions were isolated and lyophilized, with the major peak providing the title compound (0.0802 g) as a yellow solid; MALDI-MS m/z=2137.1 [(M+H)$^+$].

Alternative Synthesis of Peptide Probe F-Bak:
Acetyl-GQVGRQLAIIGDK(6-FAM)INR-NH$_2$ (SEQ ID NO:1)

The protected peptide was assembled on 0.25 mmol Fmoc-Rink amide MBHA resin (Novabiochem) on an Applied Biosystems 433A automated peptide synthesizer running FASTMOC™ coupling cycles using pre-loaded 1 mmol amino acid cartridges, except for the fluorescein(6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM:TIS:TFA (v/v/v) flowed through the resin over 15 minutes, followed by quenching with a flow of dimethylformamide. Single-isomer 6-carboxyfluorescein-NHS was reacted with the lysine side-chain in 1% DIEA in N,N-dimethylformamide and confirmed complete by ninhydrin testing. The peptide was cleaved from the resin and side-chains deprotected by treating with 80:5:5:5:2.5:2.5 TFA/water/phenol/thioanisole/triisopropylsilane: 3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z=2137.1 ((M+H)+)).

Time Resolved-Fluorescence Resonance Energy Transfer (TR-FRET) Assay

Representative compounds were serially diluted in dimethyl sulfoxide (DMSO) starting at 50 µM (2x starting concentration; 10% DMSO) and 10 µL were transferred into a 384-well plate. Then 10 µL of a protein/probe/antibody mix was added to each well at final concentrations listed in TABLE 1. The samples are then mixed on a shaker for 1 minute and incubated for an additional 3 hours at room temperature. For each assay, the probe/antibody and protein/probe/antibody were included on each assay plate as negative and positive controls, respectively. Fluorescence was measured on the ENVISION plate reader (Perkin Elmer) using a 340/35 nm excitation filter and 520/525 (F-Bak peptide) and 495/510 nm (Tb-labeled anti-Histidine antibody) emission filters. Inhibition constants (Ki) are shown in TABLE 2 below and were determined using Wang's equation (Wang Z.-X. An Exact Mathematical Expression For Describing Competitive Binding Of Two Different Ligands To A Protein Molecule. FEBS Lett. 1995, 360:111-4).

TABLE 1

Protein, Probe And Antibody Used For TR-FRET Assays

| Protein | Probe | Protein (nM) | Probe (nM) | Antibody | Antibody (nM) |
|---|---|---|---|---|---|
| GST-Bcl-2 | F-Bak Peptide Probe Acetyl-GQVGRQLAIIGDK (6-FAM) INR-amide (SEQ ID NO: 1) | 1 | 100 | Tb-anti-GST | 1 |

6-FAM = 6-carboxyfluorescein.; Tb = terbium; GST = glutathione S-transferase

TABLE 2

TR-FRET Bcl-2 Binding Ki (µM)

| Example No. | TR-FRET Binding: Bcl-2 Ki (µM) |
|---|---|
| 5 | 0.184564 |
| 6 | 0.211918 |
| 8 | 0.975006 |
| 9 | 0.026482 |
| 11 | 0.208284 |
| 13 | 0.072896 |
| 14 | 0.748598 |
| 15 | 0.047989 |
| 16 | 0.273003 |
| 18 | 0.745889 |
| 19 | 0.402855 |
| 20 | 0.279946 |
| 21 | 0.087297 |
| 22 | 0.017280 |
| 23 | 0.027303 |
| 24 | 0.010344 |
| 26 | 0.626725 |
| 27 | 0.004156 |
| 28 | 0.000125 |
| 29 | 0.002272 |
| 30 | 0.00020883 |
| 31 | 0.021618 |
| 32 | 0.0059419 |
| 33 | 0.0040901 |
| 34 | 0.0051381 |
| 35 | 0.0088374 |
| 36 | 0.031748 |
| 37 | 0.010612 |
| 38 | 0.0001741 |
| 40 | nd |
| 41 | nd |
| 42 | nd |
| 43 | nd |
| 44 | nd |
| 45 | nd | nd = not determined

The inhibition constant ($K_i$) is the dissociation constant of an enzyme-inhibitor complex or a protein/small molecule complex, wherein the small molecule is inhibiting binding of one protein to another protein. So a large $K_i$ value indicates a low binding affinity and a small $K_i$ value indicates a high binding affinity.

The data in TABLE 2 shows inhibition constants for the inhibition of a Bak BH3 peptide probe to Bcl-2 protein and indicate that compounds according to the invention have high binding affinities for anti-apoptotic Bcl-2 protein. The compounds are therefore expected to have utility in treatment of diseases during which anti-apoptotic Bcl-2 protein is expressed.

It is expected that, because compounds having Formula I bind to Bcl-2, they would also have utility as binders to anti-apoptotic proteins having close structural homology to Bcl-2, such as, for example, anti-apoptotic Bcl-$X_L$, Bcl-w, Mcl-1 and Bfl-1/A1 proteins.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, chronic lymphocytic leukemia, myeloma, prostate cancer spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110 (3), 584-90; *Blood* 2000, 95(4), 1283-92; and *New England Journal of Medicine* 2004, 351(14), 1409-1418.

Involvement of Bcl-2 proteins in arthritis is disclosed in commonly-owned U.S. Provisional Patent Application Ser. No. 60/988,479.

Involvement of Bcl-2 proteins in bone marrow transplant rejection is disclosed in commonly-owned U.S. patent application Ser. No. 11/941,196.

Overexpression of Bcl-2 proteins correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophoblastic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds having Formula (I) would inhibit growth of cells expressing Bcl-2 proteins derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, *mycobacterium avium intracellulare, mycobacterium tuberculosis*, myelodysplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *yersinia* and *salmonella*-associated arthropathy and the like.

Schemes and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP-BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

SCHEME 1

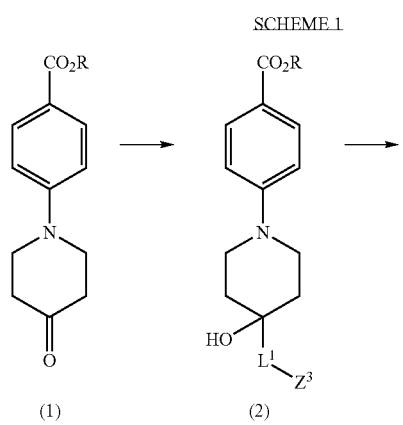

(1)　(2)

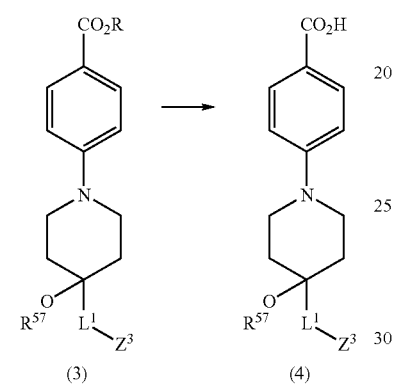

(3)　(4)

Compounds of Formula (4) can be prepared as shown in SCHEME 1, and can be used as described in SCHEME 8 to prepare compounds of Formula I, which are representative of the compounds of the present invention. Compounds of Formula (1) wherein R is alkyl, can be converted to compounds of Formula (2) using $Z^3L^1MgX^1$, wherein $X^1$ is a halide, in a solvent such as but not limited to ether or tetrahydrofuran. Compounds of Formula (3) can be prepared from compounds of Formula (2) using a strong base such as NaH and $R^{57}X^2$, wherein $X^2$ is a halide and $R^{57}$ is as described herein. Compounds of Formula (3), when treated with aqueous NaOH or LiOH, will provide compounds of Formula (4).

SCHEME 2

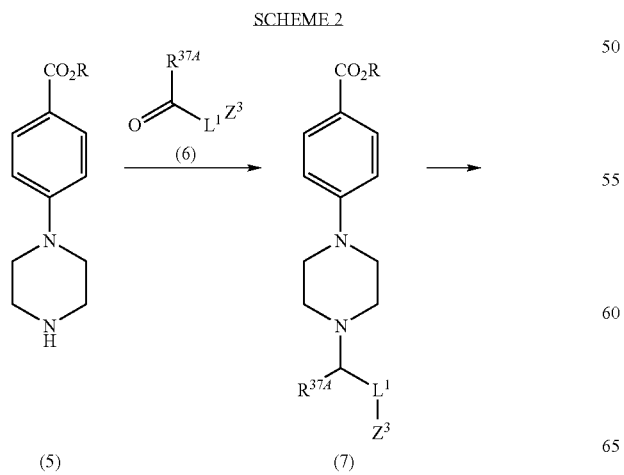

(5)　(7)

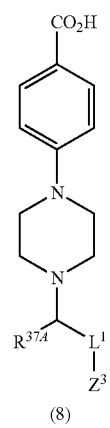

(8)

As shown in SCHEME 2, compounds of Formula (5) can be reacted with compounds of Formula (6) and a reducing agent to provide compounds of Formula (7). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, and dichloromethane or mixtures thereof. Compounds of Formula (8) can be prepared from compounds of Formula (7) as described in SCHEME 1, and can be used as described in SCHEME 8 to prepare compounds of Formula I.

SCHEME 3

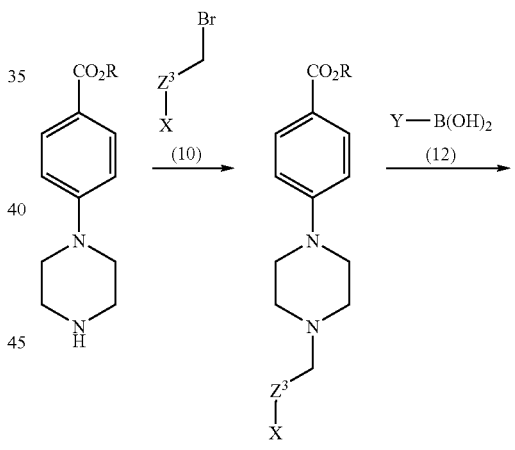

(9)　(11)

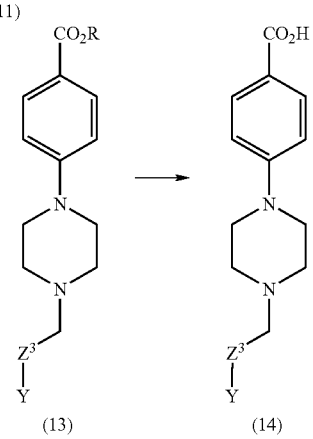

(13)　(14)

Compounds of Formula (9), when reacted with a compound a Formula (10) wherein X is a halide or triflate, and a base will provide a compound of Formula (11). Bases useful in the reaction include triethylamine, diisopropylethylamine and the like. Compounds of Formula (13), wherein Y is as described herein for substituents on $Z^3$, can be prepared from compounds of Formula (11) and compounds of Formula (12) using Suzuki coupling conditions known to those skilled in the art and readily available in the literature. Compounds of Formula (14) can be prepared from compounds of Formula (13) as described in SCHEME 1, and can be used as described in SCHEME 8 to prepare compounds of Formula I.

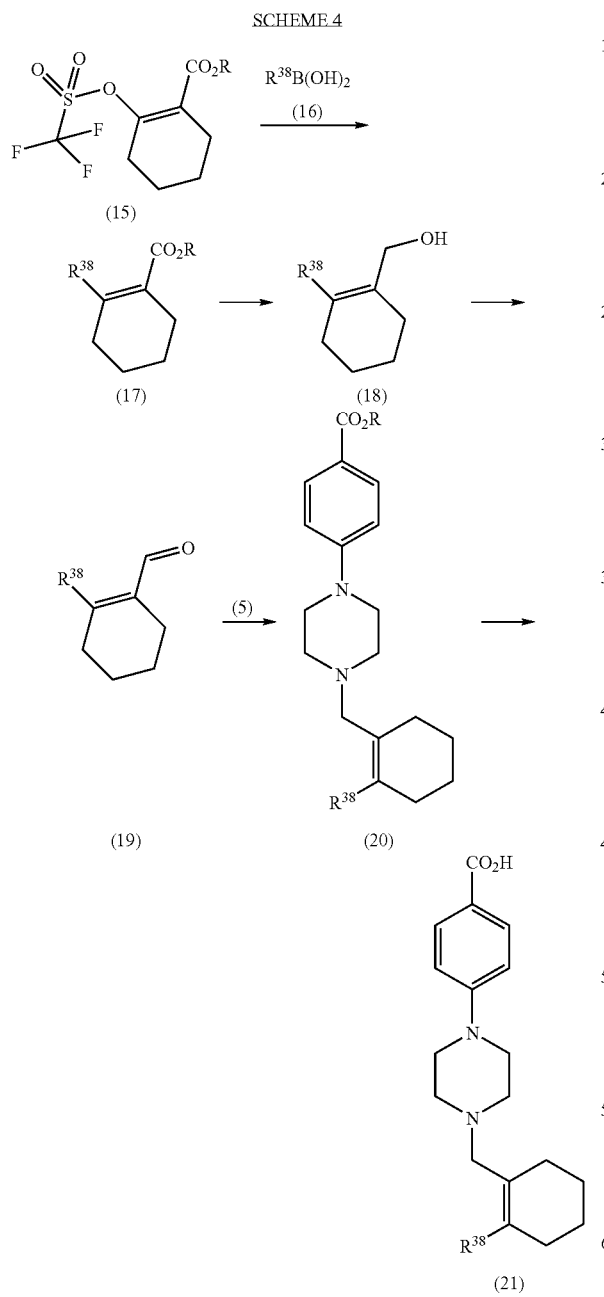

Compounds of Formula (17) can be reduced to compounds of Formula (18) using a reducing agent such as $LiAlH_4$ in a solvent such as but not limited to diethyl ether or THF. Compounds of Formula (19) can be prepared from compounds of Formula (18) using Dess-Martin periodinane or Swern oxidation conditions known to those skilled in the art and readily available in the literature. Compounds of Formula (19) can be reacted with a compound of Formula (5) and a reducing agent to provide compounds of Formula (20). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, 1,2-dichloroethane, and dichloromethane or mixtures thereof. Compounds of Formula (21) can be prepared from compounds of Formula (20) as described in SCHEME 1, and can be used as described in SCHEME 8 to prepare compounds of Formula I.

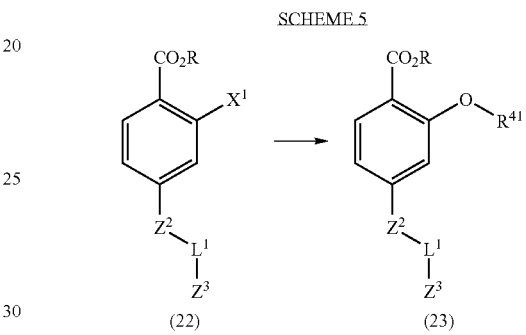

As shown in SCHEME 5, compounds of Formula (22), wherein R is alkyl, may be converted to compounds of Formula (23) by reacting the former, wherein $X^1$ is Cl, Br, I, or $CF_3SO_3$—, and compounds of Formula $R^{41}$—OH and a catalyst, with or without a first base. Examples of catalysts include copper(I) trifluoromethanesulfonate toluene complex, $PdCl_2$, $Pd(OAc)_2$, and $Pd_2(dba)_3$. Examples of first bases include triethylamine, N,N-diisopropylethylamine, $Cs_2CO_3$, $Na_2CO_3$, $K_3PO_4$, and mixtures thereof.

Compounds of Formula (22) may also be converted to compounds of Formula (23) by reacting the former, when $X^1$ is Cl, F, or $NO_2$, and compounds of Formula $R^{41}$—OH with a first base. Examples of first bases include triethylamine, N,N-diisopropylethylamine, $Cs_2CO_3$, $Na_2CO_3$, $K_3PO_4$, and mixtures thereof.

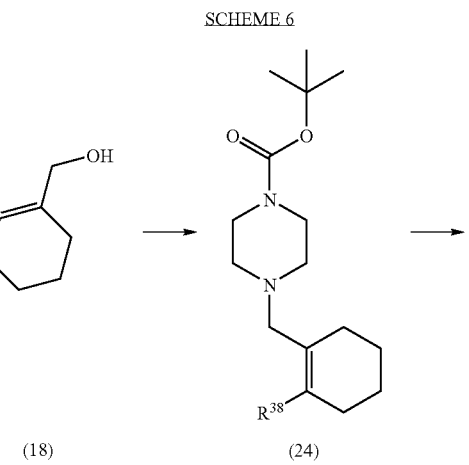

As shown in SCHEME 4, compounds of Formula (17) can be prepared from compounds of Formula (15) and compounds of Formula (16), wherein R is alkyl and $R^{38}$ is as described herein, using Suzuki coupling conditions known to those skilled in the art and readily available in the literature.

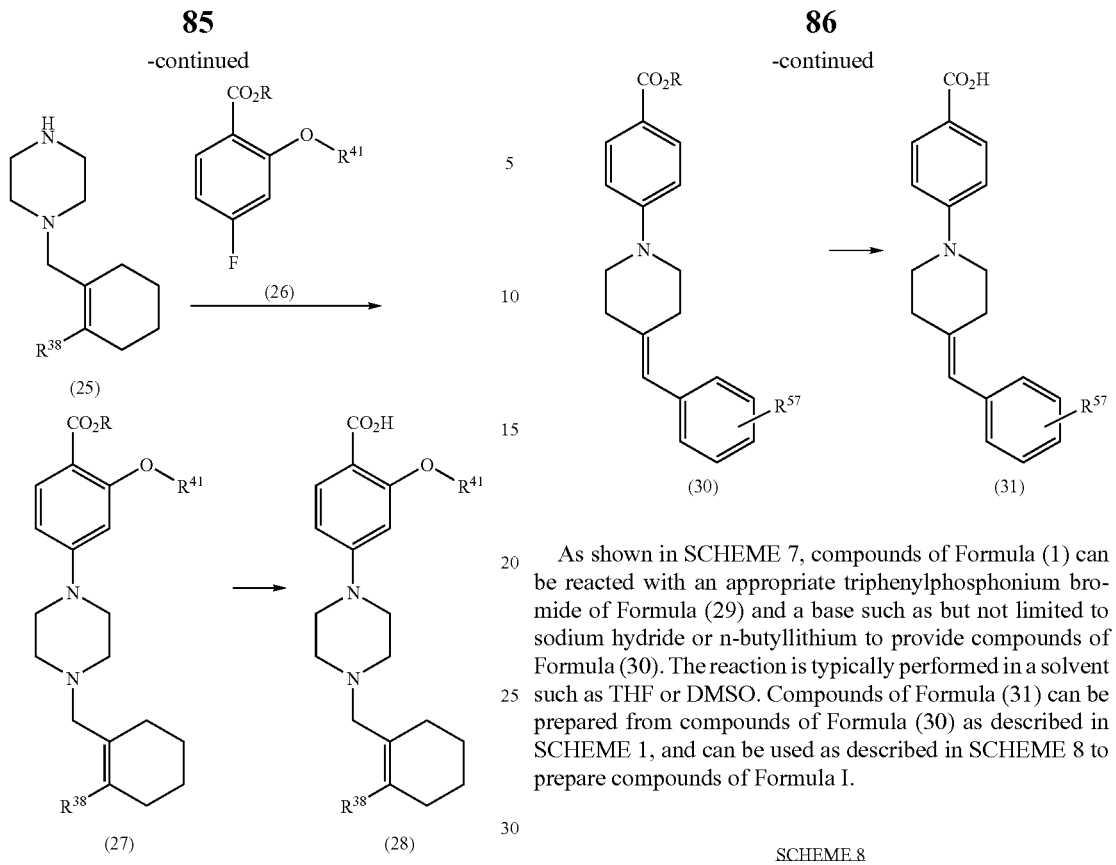

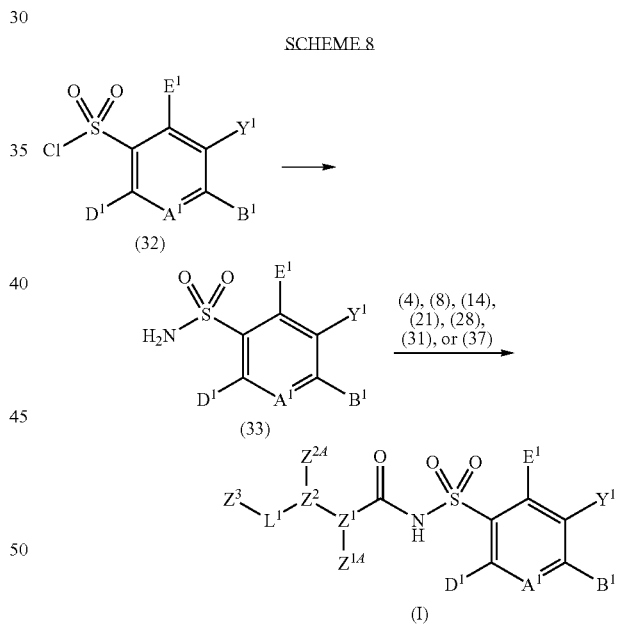

Compounds of Formula (18) can be reacted with mesyl chloride and a base such as but not limited to triethylamine, followed by N-t-butoxycarbonylpiperazine, to provide compounds of Formula (24). Compounds of Formula (25) can be prepared by reacting compounds of Formula (24) with triethylsilane and trifluoroacetic acid. Compounds of Formula (25) can be reacted with compounds of Formula (26) and $HK_2PO_4$ to provide compounds of Formula (27) in a solvent such as but not limited to dimethylsulfoxide. Compounds of Formula (28) can be prepared from compounds of Formula (27) as described in SCHEME 1, and can be used as described in SCHEME 8 to prepare compounds of Formula I.

SCHEME 7

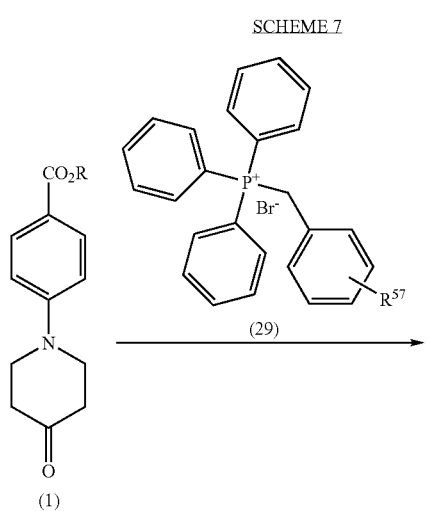

As shown in SCHEME 7, compounds of Formula (1) can be reacted with an appropriate triphenylphosphonium bromide of Formula (29) and a base such as but not limited to sodium hydride or n-butyllithium to provide compounds of Formula (30). The reaction is typically performed in a solvent such as THF or DMSO. Compounds of Formula (31) can be prepared from compounds of Formula (30) as described in SCHEME 1, and can be used as described in SCHEME 8 to prepare compounds of Formula I.

As shown in SCHEME 8, compounds of Formula (32), which can be prepared as described herein, may be converted to compounds of Formula (33) by reacting the former with ammonia. Compounds of Formula (33) may be converted to compounds of Formula (I) by reacting the former and compounds of Formula (4), (8), (14), (21), (28), (31), or (37) and a coupling agent, with or without a first base. Examples of coupling agents include 1-ethyl-3-[3-(dimethylamino)propyl]-carbodiimide hydrochloride, 1,1'-carbonyldiimidazole, and benzotriazol-1-yl-oxytripyrrolidinophosphonium hexafluorophosphate. Examples of first bases include triethylamine, N,N-diisopropylethylamine, 4-(dimethylamino)pyridine, and mixtures thereof.

SCHEME 9

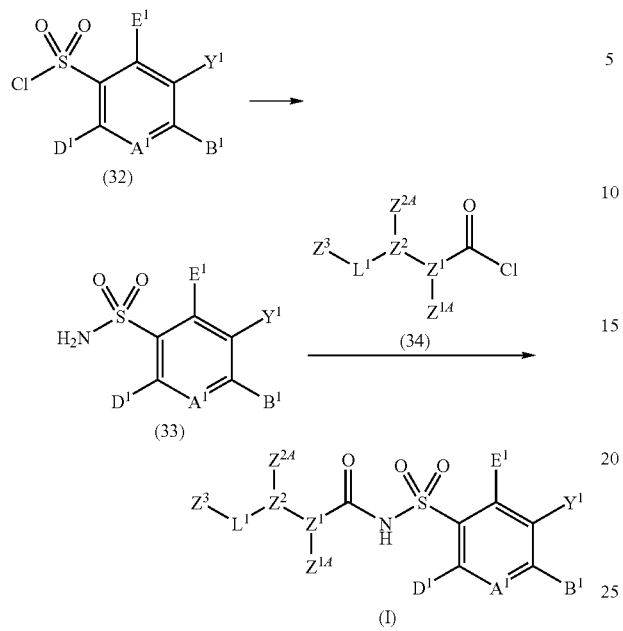

Compounds of Formula (33), prepared as described in SCHEME 1, may also be converted to compounds of Formula (I) by reacting the former and compounds of Formula (34) and a first base. Examples of first bases include but are not limited to sodium hydride, triethylamine, N,N-diisopropylethylamine, 4-(dimethylamino)pyridine, and mixtures thereof.

SCHEME 10

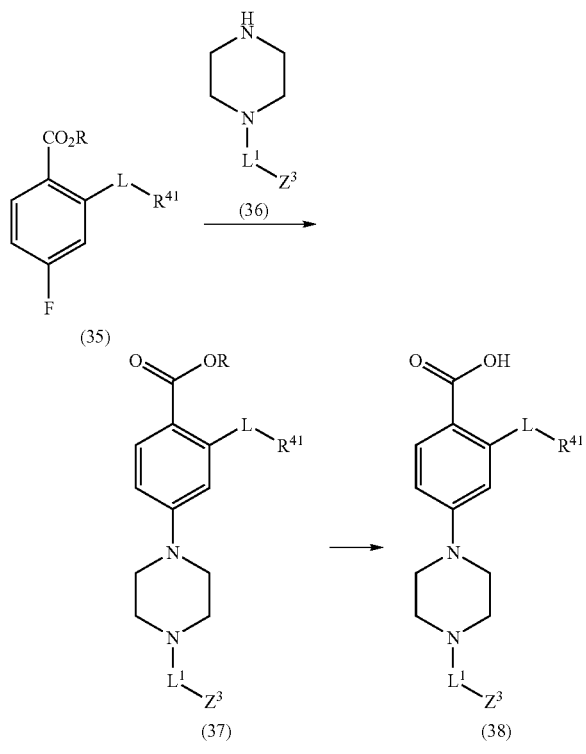

As shown in SCHEME 10, compounds of Formula (35), wherein L is a bond, alkyl, O, S, S(O), S(O)$_2$, NH, etc., can be reacted with compounds of Formula (36), to provide compounds of Formula (37). The reaction is typically performed at elevated temperatures in a solvent such as but not limited to dimethylsulfoxide, and may require the use of a base such as but not limited to potassium phosphate, potassium carbonate, and the like. Compounds of Formula (38) can be prepared from compounds of Formula (37) as described in SCHEME 1, and can be used as described in SCHEME 8 to prepare compounds of Formula I.

SCHEME 11

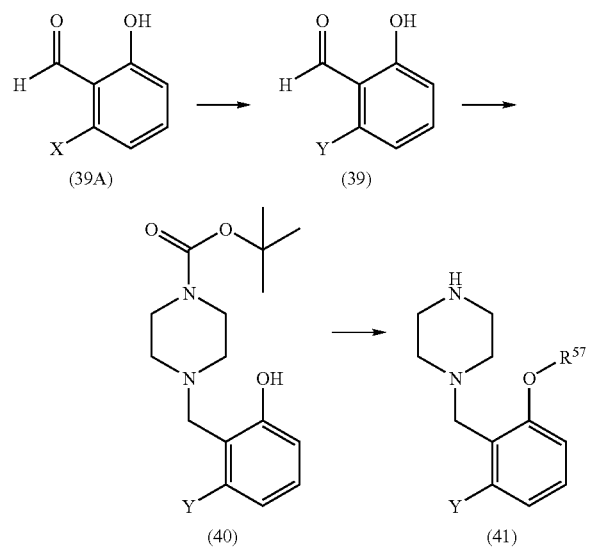

Compounds of Formula (39), wherein Y is as described herein for substituents on Z$^3$, can be prepared from compounds of Formula (39A) wherein X is a halide or triflate, and Y—B(OH)$_2$ using Suzuki coupling conditions known to those skilled in the art and readily available in the literature. Compounds of Formula (39) can be reacted with tert-butyl piperazine-1-carboxylate and a reducing agent such as sodium triacetoxyborohydride to provide compounds of Formula (40). The reaction is typically performed in a solvent such as but not limited to methylene chloride. Compounds of Formula (41) can be prepared from compounds of Formula (40) by reacting the latter with R$^{57}$X, wherein X is a halide, and NaH in a solvent such as N,N-dimethylformamide, and then the resulting material can be treated with triethylsilane and trifluoroacetic acid in dichloromethane. Compounds of Formula (41) can be used as described in Scheme 10 wherein L$^1$-Z$^3$ is as shown in Formula (41).

SCHEME 12

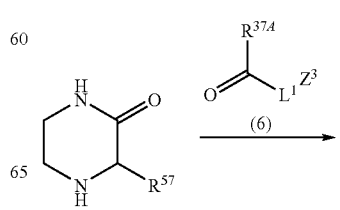

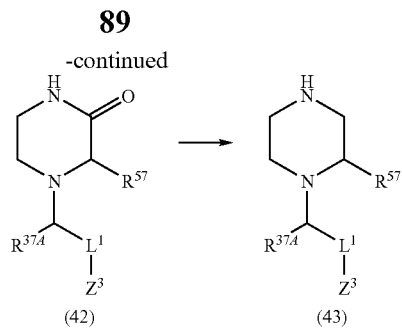

(42)          (43)

As shown in SCHEME 12, substituted piperazin-2-ones wherein $R^{57}$ is alkyl, can be reacted with compounds of Formula (6) and a reducing agent such as sodium triacetoxyborohydride in dichloromethane to provide compounds of Formula (42). Compounds of Formula (42) can be reduced to compounds of Formula (43) using a reducing agent such as but not limited to lithium aluminum hydride in a solvent such as but not limited to tetrahydrofuran. Compounds of Formula (43) can be used as described in Scheme 10 wherein $L^1$-$Z^3$ is as shown in Formula (43).

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

Example 1

4-[4-(3,3-diphenylprop-2-enyl)piperazin-1-yl]-N-[(3-nitrophenyl)sulfonyl]benzamide Example 1A tert-butyl 4-(4-(ethoxycarbonyl)phenyl)piperazine-1-carboxylate A suspension of ethyl-4-fluorobenzoate (16.8 g, 0.1 mol), tert-butyl piperazine-1-carboxylate (18.6 g, 0.1 mol) and potassium carbonate (20.7 g, 0.15 mol) in dimethylsulfoxide (100 mL) was stirred under $N_2$ at 120° C. for 10 hours. The reaction mixture was cooled to room temperature and poured into water (1 L). The solid product was filtered off, washed with water and dried in vacuum oven overnight at 40° C.

Example 1B ethyl 4-(piperazin-1-yl)benzoate

EXAMPLE 1A (13.3 g, 39.8 mmol) was dissolved in dichloromethane (50 mL) and HCl (40 mL, 4M solution in dioxane) was added. The mixture was stirred until all starting material was deprotected, as monitored by TLC. The mixture was partially concentrated and diluted with ether. The solid HCl salt was filtered off and washed with ether. The dry solid was dissolved in water and neutralized with saturated potassium carbonate to pH-10-11. The solid product was filtered off, washed with water and dried in vacuum oven.

Example 1C ethyl 4-(4-(3,3-diphenylallyl)piperazin-1-yl)benzoate

To a solution of EXAMPLE 1B (6.27 g, 26.8 mmol) and 3,3-diphenylacrylaldehyde (7.26 g, 34.8 mmol) in dichloromethane/methanol (30 mL/30 mL) was added acetic acid (0.6 mL) followed by addition of sodium triacetoxyborohydride (8.52 g, 40.2 mmol) at room temperature. The reaction mixture was stirred overnight at room temperature. The organic solvents were concentrated in vacuo and the residue was partitioned between dichloromethane and saturated aqueous sodium bicarbonate. The organic layer was washed with water and with brine, dried over magnesium sulfate, filtered and the solvent was evaporated in vacuo. The remaining residue was crystallized from acetonitrile.

Example 1D 4-(4-(3,3-diphenylallyl)piperazin-1-yl)benzoic acid

To a solution of EXAMPLE 1C (10.00 g, 23.4 mmol) in tetrahydrofuran/methanol (100/50 mL) was added solution of lithium hydroxide monohydrate (2.59 g, 70 mmol) in water (30 mL). The reaction mixture was stirred at 60° C. for 16 hours, then was cooled to room temperature and the organic solvents were concentrated. The white solid residue was dissolved in hot water and then the product was neutralized with HCl (3 equivalents). After cooling to room temperature, the precipitate was filtered off, washed with water and dried in a vacuum oven overnight at 40° C.

Example 1E

4-[4-(3,3-diphenylprop-2-enyl)piperazin-1-yl]-N-[(3-nitrophenyl)sulfonyl]benzamide A suspension of EXAMPLE 1D (39.8 mg, 0.05 mmol), 3-nitrobenzenesulfonamide (20.2 mg, 0.05 mmol), 4-dimethylaminopyridine (24.4 mg, 0.1 mmol) and 1-ethyl-3-[3-(dimethylamino)propyl]-carbodiimide hydrochloride (38.4 mg, 0.1 mmol) in dichloromethane (3 ml) was stirred for 16 hours at room temperature. The reaction mixture was concentrated and purified by RP HPLC (Zorbax SB-C8, gradient 30% to 100% $CH_3CN$/water/0.1% TFA). $^1$H NMR (500 MHz, dimethylsulfoxide-$d_6$) δ 10.49 (br s, 1H), 8.68 (s, 1H), 8.43-8.52 (m, 1H), 8.36 (d, 1H), 7.90 (t, 1H), 7.79 (d, 2H), 7.47 (t, 2H), 7.43 (t, 1H), 7.32-7.40 (m, 3H), 7.27 (d, 2H), 7.18 (d, 2H), 6.99 (d, 2H), 6.26 (t, 1H), 3.84 (d, 2H), 3.38-3.54 (br s, 4H), 3.32 (br s, 4H).

Example 2

N-[(2-bromophenyl)sulfonyl]-4-(4-{[2-(4-chlorophenyl)cyclohex-1-en-1-yl]methyl}piperazin-1-yl)benzamide Example 2A ethyl 4-(4-((2-bromocyclohex-1-enyl)methyl)piperazin-1-yl)benzoate A 100 mL round bottom flask was charged with 2-bromocyclohex-1-enecarbaldehyde, (prepared as described by Arnold, A. et. al. Collect. Czech. Chem. Commun., 1961, 26, 3059-3073.), (42 mmol), 4-piperazin-1-yl-benzoic acid ethyl ester (42 mmol) and ethanol (50 ml). The mixture was stirred and sodium cyanoborohydride (42 mmol) was added. Acetic acid was used to adjust pH to 5-6. The reaction mixture was stirred under $N_2$ at room temperature overnight. The reaction mixture was filtered and washed with ethanol. The filtered solid was discarded and the combined organic layers were concentrated under vacuum. The mixture was purified by silica gel chromatography eluting with 5-10% ethyl acetate in hexanes to provide the title compound.

Example 2B ethyl 4-(4-((2-(4-chlorophenyl)cyclohex-1-enyl)methyl)piperazin-1-yl)benzoate This compound was prepared by substituting EXAMPLE 2A for EXAMPLE 5A in EXAMPLE 5B.

Example 2C 4-(4-((2-(4-chlorophenyl)cyclohex-1-enyl)methyl)piperazin-1-yl)benzoic acid This compound was prepared by substituting EXAMPLE 2B for EXAMPLE 5B in EXAMPLE 5C.

Example 2D

N-[(2-bromophenyl)sulfonyl]-4-(4-{[2-(4-chlorophenyl)cyclohex-1-en-1-yl]methyl}piperazin-1-yl)benzamide This compound was prepared by substituting EXAMPLE 2C and 2-bromobenzenesulfonamide for EXAMPLE 1D and 3-nitrobenzenesulfonamide respectively, in EXAMPLE 1E. $^1$H NMR (500 MHz, dimethylsulfoxide-$d_6$) δ 12.54 (br s, 1H) 9.29 (br s, 1H) 8.18 (dd, 1H) 7.84 (m, 3H) 7.66 (m, 1H) 7.59 (m, 1H) 7.42 (m, 2H) 7.16 (m, 2H), 6.96 (m, 2H) 3.95 (m, 2H) 3.62 (m, 2H) 3.17 (m, 2H) 2.83 (m, 2H) 2.24 (m, 4H) 1.72 (m, 4H).

Example 3

N-[(3-bromophenyl)sulfonyl]-4-(4-{[2-(4-chlorophenyl)cyclohex-1-en-1-yl]methyl}piperazin-1-yl)benzamide This compound was prepared by substituting EXAMPLE 2C and 3-bromobenzenesulfonamide for EXAMPLE 1D and 3-nitrobenzenesulfonamide respectively, in EXAMPLE 1E. $^1$H NMR (500 MHz, dimethylsulfoxide-$d_6$) δ 12.29 (br s, 1H) 9.26 (s, 1H) 8.08 (m, 1H) 7.94 (m, 2H) 7.78 (d, 2H) 7.60 (t, 1H) 7.42 (d, 2H) 7.15 (d, 2H) 6.96 (d, 2H) 3.91 (m, 2H) 3.61 (m, 2H) 3.16 (m, 2H) 2.80 (m, 2H) 2.24 (m, 4H) 1.71 (m, 4H).

Example 4

N-[(4-bromophenyl)sulfonyl]-4-(4-{[2-(4-chlorophenyl)cyclohex-1-en-1-yl]methyl}piperazin-1-yl)benzamide This compound was prepared by substituting EXAMPLE 2C and 4-bromobenzenesulfonamide for EXAMPLE 1D and 3-nitrobenzenesulfonamide respectively, in EXAMPLE 1E. $^1$H NMR (400 MHz, dimethylsulfoxide-$d_6$) δ 12.24 (br s, 1H) 9.33 (br s, 1H) 7.87 (m, 4H) 7.77 (m, 2H) 7.40 (m, 2H) 7.15 (m, 2H) 6.95 (m, 2H) 3.91 (m, 2H) 3.61 (m, 2H) 3.16 (m, 2H) 2.82 (m, 2H) 2.24 (m, 4H) 1.72 (m, 4H).

Example 5

4-{4-[(4'-chloro-1,1'-biphenyl-2-yl)methyl]piperazin-1-yl}-N-[(3-nitrophenyl)sulfonyl]benzamide Example 5A ethyl 4-(4-(2-bromobenzyl)piperazin-1-yl)benzoate A solution of EXAMPLE 1B (23.43 g, 100.0 mmol), 2-bromobenzyl bromide (26.24 g, 105.0 mmol) and diisopropylethylamine (20.94 mL, 120 0 mmol) in acetonitrile (200 mL) was stirred at room temperature for two hours. The resulting precipitate was collected by filtration to give the title compound, which was used without further purification.

Example 5B ethyl 4-(4-((4'-chlorobiphenyl-2-yl)methyl)piperazin-1-yl)benzoate

A suspension of EXAMPLE 5A (13.83 g, 34.3 mmol), 4-chlorophenylboronic acid (7.04 g, 45.0 mmol), bis(triphenylphosphine)palladium(II) dichloride (0.481 g, 0.686 mmol, 2 mol %) and aqueous 2M $Na_2CO_3$ (22.5 mL, 45.0 mmol) in 1,2-dimethoxyethane/$H_2O$/ethanol (7:3:2, 200 mL) was heated at 90° C. for 4.5 hours and diluted with ethyl acetate (200 mL). The layers were separated and the organic phase was dried ($MgSO_4$), filtered, and concentrated. The residue was purified by silica gel chromatography eluting with a gradient from 5%-40% ethyl acetate/hexanes to give the title compound.

Example 5C 4-(4-((4'-chlorobiphenyl-2-yl)methyl)piperazin-1-yl)benzoic acid

A suspension of EXAMPLE 5B (13.0 g, 29.9 mmol) and LiOH monohydrate (3.78 g, 90.0 mmol) in dioxane (250 mL) and water (100 mL) was heated at 95° C. for 16 hours, concentrated to dryness, treated with water (600 mL), heated to 80° C., and filtered. The filtrate was treated with 1M HCl (90 mL) and the resulting precipitate was collected by filtration and dried to give the title compound.

Example 5D

4-{4-[(4'-chloro-1,1'-biphenyl-2-yl)methyl]piperazin-1-yl}-N-[(3-nitrophenyl)sulfonyl]benzamide The title compound was prepared by substituting EXAMPLE 5C for EXAMPLE 1D in EXAMPLE 1E. $^1$H NMR (300 MHz, dimethylsulfoxide-$d_6$) δ 8.66 (t, 1H), 8.52 (m, 1H), 8.37 (d, 1H), 7.93 (t, 1H), 7.74 (d, 3H), 7.52 (m, 4H), 7.39 (m, 2H), 7.32 (m, 1H), 6.92 (d, 2H), 4.37 (br s, 2H), 3.90 (m, 2H), 3.11 (m, 4H), 2.87 (m, 2H).

Example 6

4-{4-[(4'-chloro-1,1'-biphenyl-2-yl)methyl]piperazin-1-yl}-N-(phenylsulfonyl)benzamide The title compound was prepared by substituting EXAMPLE 5C and benzenesulfonamide for EXAMPLE 1D and 3-nitrobenzenesulfonamide respectively, in EXAMPLE 1E. $^1$H NMR (300 MHz, dimethylsulfoxide-$d_6$) δ 12.16 (br s, 1H), 7.98 (m, 1H), 7.95 (m, 1H), 7.75 (m, 3H), 7.70 (m, 1H), 7.62 (m, 2H), 7.71 (d, 2H), 7.54 (m, 4H), 7.38 (d, 2H), 7.34 (d, 1H), 6.93 (d, 2H), 4.37 (br s, 2H), 3.91 (m, 2H), 3.26 (m, 2H), 3.09 (m, 2H), 2.86 (m, 2H).

Example 7

2-(benzyloxy)-4-{4-[(4'-chloro-1,1'-biphenyl-2-yl)methyl]piperazin-1-yl}-N-[(3-nitrophenyl)sulfonyl]benzamide

Example 7A tert-butyl 4((4'-chlorobiphenyl-2-yl)methyl)piperazine-1-carboxylate 4'-Chlorobiphenyl-2-carboxaldehyde (4.1 g), tert-butyl piperazine-1-carboxylate (4.23 g), and sodium triacetoxyborohydride (5.61 g) in $CH_2Cl_2$ (60 mL) was stirred for 24 hours. The reaction was quenched with methanol and poured into ether. The solution was washed with water and brine, concentrated, and chromatographed on silica gel with 2-25% ethyl acetate/hexanes.

Example 7B 1-((4'-chlorobiphenyl-2-yl)methyl)piperazine

EXAMPLE 7A (3.0 g) and triethylsilane (1 mL) were stirred in $CH_2Cl_2$ (30 mL) and trifluoroacetic acid (30 mL) for 2 hours, and the reaction was concentrated, and then taken up in ether and concentrated again. The product was used without further purification.

Example 7C methyl 2-(benzyloxy)-4-fluorobenzoate

Methyl 4-fluoro-2-hydroxybenzoate (2.00 g), benzyl bromide (1.54 mL), and cesium carbonate (4.60 g) in N,N-dimethylformamide (50 mL) were stirred in for 24 hours. The reaction was taken up in ether and washed 3× with 1M NaOH solution and with brine, then concentrated to give the title compound.

Example 7D methyl 2-(benzyloxy)-4-(4-((4'-chlorobiphenyl-2-yl)methyl)piperazin-1-yl)benzoate EXAMPLE 7C (570 mg), EXAMPLE 7B (754 mg), and $K_2CO_3$ (605 mg) were stirred in dimethylsulfoxide at 125° C. for 5 hours. The reaction was cooled and chromatographed on silica gel with 10% ethyl acetate/hexanes.

Example 7E 2-(benzyloxy)-4-(4-((4'-chlorobiphenyl-2-yl)methyl)piperazin-1-yl)benzoic acid The title compound was prepared by substituting EXAMPLE 7D for EXAMPLE 5B in EXAMPLE 5C.

Example 7F 2-(benzyloxy)-4-{4-[(4'-chloro-1,1'-biphenyl-2-yl)methyl]piperazin-1-yl}-N-[(3-nitrophenyl)sulfonyl]benzamide The title compound was prepared by substituting EXAMPLE 7E for EXAMPLE 1D in EXAMPLE 1E. The crude material was chromatographed on silica gel with 20-50% ethyl acetate/hexanes. $^1$H NMR (300 MHz, dimethylsulfoxide-$d_6$) δ 11.95 (br s, 1H), 8.66 (d, 1H), 8.59 (d, 1H), 8.47 (m, 2H), 8.25 (m, 2H), 7.89 (m, 2H), 7.71 (d, 2H), 7.37-7.54 (m, 7H), 7.26 (m, 1H), 6.60 (d, 1H), 6.54 (d, 1H), 5.21 (s, 2H), 3.42 (s, 2H), 3.26 (m, 4H), 2.38 (m, 4H).

Example 8

4-{4-[(4'-chloro-1,1'-biphenyl-2-yl)methyl]piperazin-1-yl}-N-[(3-nitrophenyl)sulfonyl]-2-(2-phenylethoxy)benzamide

Example 8A methyl 4-fluoro-2-phenethoxybenzoate

Methyl 4-fluoro-2-hydroxybenzoate (1.00 g) and phenethyl alcohol (0.64 mL) were added to triphenylphosphine (1.54 g) and diisopropylazodicarboxylate (1.04 mL) in tetrahydrofuran (20 mL) at 0° C., and the mixture was stirred at room temperature for 24 hours. The reaction was chromatographed on silica gel with 5% ethyl acetate/hexanes.

Example 8B methyl 4-(4-((4'-chlorobiphenyl-2-yl)methyl)piperazin-1-yl)-2-phenethoxybenzoate The title compound was prepared by substituting EXAMPLE 8A for EXAMPLE 7C in EXAMPLE 7D.

Example 8C 4-(4-((4'-chlorobiphenyl-2-yl)methyl)piperazin-1-yl)-2-phenethoxybenzoic acid The title compound was prepared by substituting EXAMPLE 8B for EXAMPLE 5B in EXAMPLE 5C.

Example 8D

4-{4-[(4'-chloro-1,1'-biphenyl-2-yl)methyl]piperazin-1-yl}-N-[(3-nitrophenyl)sulfonyl]-2-(2-phenylethoxy)benzamide The title compound was prepared by substituting EXAMPLE 8C for EXAMPLE 1D in EXAMPLE 1E. The reaction was chromatographed on silica gel with 20-50% ethyl acetate/hexanes. $^1$H NMR (300 MHz, dimethylsulfoxide-$d_6$) δ 11.05 (br s, 1H), 8.71 (d, 1H), 8.53 (d, 1H), 8.37 (d, 1H), 7.93 (dd, 2H), 7.30-7.50 (m, 11H), 7.25 (m, 2H), 6.49 (m, 2H), 4.33 (t, 2H), 3.42 (s, 2H), 3.26 (m, 4H), 3.14 (t, 2H), 2.37 (m, 4H).

Example 9

4-{4-[(4'-chloro-1,1'-biphenyl-2-yl)methyl]piperazin-1-yl}-N-[(3-nitrophenyl)sulfonyl]-2-phenoxybenzamide

Example 9A methyl 4-fluoro-2-phenoxybenzoate

Methyl 2-bromo-4-fluorobenzoate (1 g), phenol (0.565 g), cesium carbonate (1.96 g), copper(I) triflate toluene complex (0.087 g), and ethyl acetate (0.034 mL) in toluene (12 mL) was stirred at 110° C. for 24 hours. The reaction was cooled and chromatographed on silica gel with 5% ethyl acetate/hexanes.

Example 9B methyl 4-(4-((4'-chlorobiphenyl-2-yl)methyl)piperazin-1-yl)-2-phenoxybenzoate The title compound was prepared by substituting EXAMPLE 9A for EXAMPLE 7C in EXAMPLE 7D.

Example 9C 4-(4-((4'-chlorobiphenyl-2-yl)methyl)piperazin-1-yl)-2-phenoxybenzoic acid The title compound was prepared by substituting EXAMPLE 9B for EXAMPLE 5B in EXAMPLE 5C.

Example 9D

4-{4-[(4'-chloro-1,1'-biphenyl-2-yl)methyl]piperazin-1-yl}-N-[(3-nitrophenyl)sulfonyl]-2-phenoxybenzamide The title compound was prepared by substituting EXAMPLE 9C for EXAMPLE 1D in EXAMPLE 1E. The reaction was chromatographed on silica gel with 20-50% ethyl acetate/hexanes. $^1$H NMR (300 MHz, dimethylsulfoxide-$d_6$) δ 11.50 (br s, 1H), 8.52 (s, 1H), 8.42 (d, 1H), 8.16 (d, 1H), 7.78 (t, 1H), 7.33-7.57 (m, 8H), 7.22 (m, 3H), 6.96 (dd, 1H), 6.77 (m, 3H), 6.39 (d, 1H), 3.49 (s, 2H), 3.18 (m, 4H), 2.43 (m, 4H).

Example 10

4-{4-[(4'-chloro-1,1'-biphenyl-2-yl)methyl]piperazin-1-yl}-2-phenoxy-N-(phenylsulfonyl)benzamide The title compound was prepared by substituting EXAMPLE 9C for EXAMPLE 1D and benzenesulfonamide for 3-nitrobenzenesulfonamide in EXAMPLE 1E. The reaction was chromatographed on silica gel with 20-50% ethyl acetate/hexanes. $^1$H NMR (300 MHz, dimethylsulfoxide-$d_6$) δ 11.55 (br s, 1H), 7.82 (m, 3H), 7.42-7.64 (m, 7H), 7.34 (m, 5H), 7.25 (d, 1H), 7.10 (dd, 1H), 6.90 (d, 2H), 6.75 (d, 1H), 6.35 (d, 1H), 3.37 (s, 2H), 3.14 (m, 4H), 2.34 (m, 4H).

Example 11

N-[(4-bromophenyl)sulfonyl]-4-{4-[(4'-chloro-1,1'-biphenyl-2-yl)methyl]piperazin-1-yl}benzamide The title compound was prepared by substituting EXAMPLE 5C for EXAMPLE 1D and 4-bromobenzenesulfonamide for 3-nitrobenzenesulfonamide in EXAMPLE 1E, except here the purification was done by flash column chromatography on silica gel eluting with a gradient of 30% ethyl acetate/hexanes to 50% ethyl acetate/hexanes. $^1$H NMR (400 MHz, dimethylsulfoxide-$d_6$) δ 7.89-7.78 (m, 4H), 7.73 (d, 2H), 7.55-7.43 (m, 5H), 7.39 (m, 2H), 7.27-7.24 (m, 1H), 6.90 (d, 2H), 3.48 (bs, 2H), 3.26 (bs, 4H), 2.45 (bs, 4H).

Example 12

4-[4-(1,1'-biphenyl-4-ylmethyl)-3-isopropylpiperazin-1-yl]-N-(phenylsulfonyl)benzamide

Example 12A 3-isopropylpiperazin-2-one

Ethyl 2-bromo-3-methylbutanoate (2.2 g, 10.52 mmol) in ethanol (15 mL) was added dropwise over a period of 2.5 hours to a stirred refluxing solution of ethane-1,2-diamine (13.2 mL, 197 mmol) in ethanol (60 mL). The mixture was heated for another 2.5 hours, and sodium ethoxide in ethanol (21% by wt) (4.0 mL, 10.80 mmol) was added and the mixture was heated for another 90 minutes. The reaction was then cooled and concentrated. After trituration with ether, the title compound was used in the next step without further purification.

Example 12B 4-((4'-chlorobiphenyl-2-yl)methyl)-3-isopropylpiperazin-2-one

EXAMPLE 12A (590 mg, 4.15 mmol) and 4'-chlorobiphenyl-2-carboxaldehyde (970 g, 4.48 mmol) were dissolved in $CH_2Cl_{22}$ (16 ml), and sodium triacetoxyborohydride (1050 mg, 4.95 mmol) was added. The reaction stirred at room temperature for two days under a drying tube. The reaction was partitioned between aqueous saturated $NaHCO_3$ and ethyl acetate. The organic layer was washed with brine, dried over $Na_2SO_4$, and purified by flash chromatography using 7/3 hexanes/ethyl acetate.

Example 12C 1-(biphenyl-2-ylmethyl)-2-isopropylpiperazine

A 1.0M solution of lithium aluminum hydride in tetrahydrofuran (4.8 mL, 4.8 mmol) was cooled to 0°, then a solution of EXAMPLE 12B (0.45 g, 1.31 mmol) in tetrahydrofuran (9 mL) was added dropwise. The reaction was stirred at room temperature overnight. The next day more lithium aluminum hydride solution was added (4.8 mL, 4.8 mmol) and the reaction stirred at room temperature for another two days. The reaction was then cooled to 0° and water (0.75 mL) was carefully added, followed by 4N NaOH (0.75 mL), and additional water (2.2 mL). $Na_2SO_4$ and ether (25 mL) were added, and after stirring for 45 minutes ; the mixture was filtered through Celite® (diatomaceous earth). Concentration of the filtrate gave the title compound.

Example 12D methyl 4-(4-(biphenyl-2-ylmethyl)-3-isopropylpiperazin-1-yl)-2-phenoxybenzoate The title compound was prepared by substituting EXAMPLE 12C for tert-butyl piperazine-1-carboxylate and EXAMPLE 9A for ethyl-4-fluorobenzoate in EXAMPLE 1A.

Example 12E 4-(4-(biphenyl-2-ylmethyl)-3-isopropylpiperazin-1-yl)-2-phenoxybenzoic acid The title compound was prepared by substituting EXAMPLE 12D for EXAMPLE 5B in EXAMPLE 5C.

Example 12F

4-[4-(1,1'-biphenyl-4-ylmethyl)-3-isopropylpiperazin-1-yl]-N-(phenylsulfonyl)benzamide The title compound was prepared by substituting EXAMPLE 12E for EXAMPLE 1D and benzenesulfonamide for 3-nitrobenzenesulfonamide in EXAMPLE 1E, except here the purification was done by preparative HPLC using a C18 column, 250×50 mm, 10μ, and eluting with a gradient of 20-100% CH$_3$CN vs. 0.1% TFA in water, giving the product as a trifluoroacetate salt. $^1$H NMR (300 MHz, dimethylsulfoxide-d$_6$) δ 12.15 (br s, 1H), 8.90 (br s, 1H), 7.99 (d, 2H), 7.75 (m, 4H), 7.65 (m, 3H), 7.40 (m, 8H), 6.90 (m, 2H), 4.82 (v br s, 1H), 4.50 (v br s, 1H), 4.20 (v br s, 1H), 3.77, 3.20, 2.90 (all v br s, total 6H), 2.10 (v br s, 1H), 0.95 (d, 3H), 0.80 (d, 3H).

Example 13

4-{4-[(4'-chloro-1,1'-biphenyl-2-yl)methyl]piperazin-1-yl}-N-[(3-nitrophenyl)sulfonyl]-2-(phenylthio)benzamide

Example 13A methyl 4-fluoro-2-(phenylthio)benzoate

5-Fluoro-2-(methoxycarbonyl)phenylboronic acid (1.00 g), 2-(phenylthio)isoindoline-1,3-dione (0.86 g), and (2-hydroxy-3,5-diisopropylbenzoyloxy)copper (0.29 g) were stirred in dioxane (15 mL) at 50° C. for 24 hours. The reaction mixture was chromatographed on silica gel with 5% ethyl acetate/hexanes.

Example 13B methyl 4-(4-((4'-chlorobiphenyl-2-yl)methyl)piperazin-1-yl)-2-(phenylthio)benzoate The title compound was prepared by substituting EXAMPLE 13A for EXAMPLE 7C in EXAMPLE 7D.

Example 13C 4-(4-((4'-chlorobiphenyl-2-yl)methyl)piperazin-1-yl)-2-(phenylthio)benzoic acid The title compound was prepared by substituting EXAMPLE 13B for EXAMPLE 5B in EXAMPLE 5C.

Example 13D

4-{4-[(4'-chloro-1,1'-biphenyl-2-yl)methyl]piperazin-1-yl}-N-[(3-nitrophenyl)sulfonyl]-2-(phenylthio)benzamide The title compound was prepared by substituting EXAMPLE 13C for EXAMPLE 1D in EXAMPLE 1E. The reaction was chromatographed on silica gel with 20-50% ethyl acetate/hexanes. $^1$H NMR (300 MHz, dimethylsulfoxide-d$_6$) δ 8.63 (d, 1H), 8.42 (d, 1H), 8.32 (d, 1H), 7.84 (dd, 1H), 7.74 (d, 1H), 7.30-7.56 (m, 10H), 7.25 (m, 2H), 7.17 (m, 1H), 6.71 (dd, 1H), 6.11 (d, 1H), 3.68 (s, 2H), 3.31 (m, 4H), 2.97 (m, 4H).

Example 14

2-(benzylamino)-4-{4-[(4'-chloro-1,1'-biphenyl-2-yl)methyl]piperazin-1-yl}-N-[(3-nitrophenyl)sulfonyl]benzamide

Example 14A methyl 2-(benzylamino)-4-fluorobenzoate

Methyl 2-amino-4-fluorobenzoate (0.90 g), benzaldehyde (0.54 mL), sodium triacetoxyborohydride (1.58 g) and acetic acid (0.3 mL) in CH$_2$Cl$_2$ (20 mL) were stirred for 3 hours. The reaction was quenched with methanol, concentrated, and chromatographed on silica gel with 5% ethyl acetate/hexanes.

Example 14B methyl 2-(benzylamino)-4-(4-((4'-chlorobiphenyl-2-yl)methyl)piperazin-1-yl)benzoate The title compound was prepared by substituting EXAMPLE 14A for EXAMPLE 7C in EXAMPLE 7D.

Example 14C 2-(benzylamino)-4-(4-((4'-chlorobiphenyl-2-yl)methyl)piperazin-1-yl)benzoic acid The title compound was prepared by substituting EXAMPLE 14B for EXAMPLE 5B in EXAMPLE 5C.

Example 14D 2-(benzylamino)-4-{4-[(4'-chloro-1,1'-biphenyl-2-yl)methyl]piperazin-1-yl}-N-[(3-nitrophenyl)sulfonyl]benzamide The title compound was prepared by substituting EXAMPLE 14C for EXAMPLE 1D in EXAMPLE 1E. The reaction was chromatographed on silica gel with 20-50% ethyl acetate/hexanes. $^1$H NMR (300 MHz, dimethylsulfoxide-d$_6$) δ 9.75 (br s, 1H), 8.62 (d, 1H), 8.42 (d, 1H), 8.29 (d, 1H), 7.85 (dd, 1H), 7.66 (d, 1H), 7.42-7.58 (m, 7H), 7.14-7.31 (m, 6H), 6.14 (dd, 1H), 5.88 (s, 1H), 4.32 (d, 2H), 3.60 (s, 2H), 3.16 (m, 4H), 2.55 (m, 4H).

Example 15

2-benzyl-4-{4-[(4'-chloro-1,1'-biphenyl-2-yl)methyl]piperazin-1-yl}-N-[(3-nitrophenyl)sulfonyl]benzamide Example 15A methyl 2-benzyl-4-fluorobenzoate 5-Fluoro-2-(methoxycarbonyl)phenylboronic acid (1.00 g), benzyl bromide (0.50 mL), $K_2CO_3$ (1.75 g), and [1,1'-bis(diphenylphosphino)ferrocene]dichloropalladium(II) (0.17 g) were stirred in tetrahydrofuran (20 mL) at 60° C. for 24 hours. The reaction mixture was chromatographed on silica gel with 2% ethyl acetate/hexanes.

Example 15B methyl 2-benzyl-4-(4-((4'-chlorobiphenyl-2-yl)methyl)piperazin-1-yl)benzoate The title compound was prepared by substituting EXAMPLE 15A for EXAMPLE 7C in EXAMPLE 7D.

Example 15C 2-benzyl-4-(4-((4'-chlorobiphenyl-2-yl)methyl)piperazin-1-yl)benzoic acid The title compound was prepared by substituting EXAMPLE 15B for EXAMPLE 5B in EXAMPLE 5C.

Example 15D 2-benzyl-4-{4-[(4'-chloro-1,1'-biphenyl-2-yl)methyl]piperazin-1-yl}-N-[(3-nitrophenyl)sulfonyl]benzamide The title compound was prepared by substituting EXAMPLE 15C for EXAMPLE 1D in EXAMPLE 1E. The reaction was chromatographed on silica gel with 20-50% ethyl acetate/hexanes. $^1$H NMR (300 MHz, DMSO-$d_6$) δ 11.95 (br s, 1H), 8.56 (d, 1H), 8.37 (d, 1H), 8.22 (d, 1H), 7.79 (dd, 1H), 7.36-7.56 (m, 8H), 7.25 (d, 1H), 6.98 (m, 3H), 6.92 (m, 2H), 6.72 (s, 1H), 6.69 (d, 1H), 4.15 (s, 2H), 3.46 (br s, 4H), 3.15 (br s, 4H), 2.44 (br s, 4H).

Example 16

4-{4-[(4'-chloro-1,1'-biphenyl-2-yl)methyl]piperazin-1-yl}-N-[(4-nitrophenyl)sulfonyl]benzamide The title compound was prepared by substituting EXAMPLE 5C and 4-nitrobenzenesulfonamide for EXAMPLE 1D and 3-nitrobenzenesulfonamide respectively, in EXAMPLE 1E. $^1$H NMR (300 MHz, dimethylsulfoxide-$d_6$) δ 8.41 (d, 2H), 8.20 (d, 2H), 7.75 (d, 2H), 7.71 (br s, 1H), 7.52 (m, 4H), 7.40 (d, 2H), 7.33 (m, 1H), 6.92 (d, 2H), 4.18 (br s, 2H), 3.42 (m, 4H), 2.89 (m, 4H).

Example 17

4-{4-[(4'-chloro-1,1'-biphenyl-2-yl)methyl]piperazin-1-yl}-N-[(4-hydroxyphenyl)sulfonyl]benzamide The title compound was prepared by substituting EXAMPLE 5C and 4-hydroxybenzenesulfonamide for EXAMPLE 1D and 3-nitrobenzenesulfonamide respectively, in EXAMPLE 1E. $^1$H NMR (300 MHz, dimethylsulfoxide-$d_6$) δ 7.95 (d, 2H), 7.90 (d, 2H), 7.54 (m, 5H), 7.42 (m, 6H), 7.04 (d, 2H), 4.30 (br s, 2H), 3.19 (m, 4H), 2.89 (m, 4H).

Example 18

4-{4-[(4'-chloro-1,1'-biphenyl-2-yl)methyl]piperazin-1-yl}-N-[(3-nitrophenyl)sulfonyl]-2-(2-phenylethyl)benzamide Example 18A methyl 4-fluoro-2-phenethylbenzoate Methyl 2-bromo-4-fluorobenzoate (1.00 g), (E)-styrylboronic acid (0.89 g), tetrakis(triphenylphosphine)palladium(0) (0.50 g), and $K_3PO_4$ (2.28 g) were stirred in dioxane (17 mL) at 90° C. for 24 hours. The reaction mixture was chromatographed on silica gel with 1-5% ethyl acetate/hexanes. The product in methanol (10 ml) was added to 20 wt % of fresh dry 5% Pd-C and stirred 4 days with $H_2$ in a pressure bottle. The mixture was filtered through a nylon membrane and concentrated.

Example 18B methyl 4-(4-((4'-chlorobiphenyl-2-yl)methyl)piperazin-1-yl)-2-phenethylbenzoate The title compound was prepared by substituting EXAMPLE 18A for EXAMPLE 7C in EXAMPLE 7D.

Example 18C 4-(4-((4'-chlorobiphenyl-2-yl)methyl)piperazin-1-yl)-2-phenethylbenzoic acid The title compound was prepared by substituting EXAMPLE 18B for EXAMPLE 5B in EXAMPLE 5C.

Example 18D

4-{4-[(4'-chloro-1,1'-biphenyl-2-yl)methyl]piperazin-1-yl}-N-[(3-nitrophenyl)sulfonyl]-2-(2-phenylethyl)benzamide The title compound was prepared by substituting EXAMPLE 18C for EXAMPLE 1D in EXAMPLE 1E. The reaction was chromatographed on silica gel with 20-50% ethyl acetate/hexanes. $^1$H NMR (300 MHz, DMSO-$d_6$) δ 12.20 (br s, 1H), 8.70 (d, 1H), 8.37 (d, 1H), 8.24 (d, 1H), 7.82 (dd, 1H), 7.35-7.56 (m, 8H), 7.26 (d, 1H), 7.17 (m, 3H), 6.95 (m, 2H), 6.69 (m, 2H), 3.46 (br s, 4H), 3.15 (br s, 4H), 2.85 (t, 2H), 2.62 (t, 2H), 2.44 (br s, 4H).

Example 19

4-{4-[(4'-chloro-1,1'-biphenyl-2-yl)methyl]piperazin-1-yl}-N-[(4-fluorophenyl)sulfonyl]benzamide The title compound was prepared by substituting EXAMPLE 5C and 4-fluorobenzenesulfonamide for EXAMPLE 1D and 3-nitrobenzenesulfonamide respectively, in EXAMPLE 1E. $^1$H NMR (300 MHz, dimethylsulfoxide-$d_6$) δ 8.03 (m, 2H), 7.75 (m, 3H), 7.52 (m, 3H), 7.47 (m, 3H), 7.40 (m, 2H), 7.34 (br s, 1H), 6.92 (d, 2H), 4.38 (br s, 2H), 3.88 (m, 2H), 3.12 (m, 4H), 2.87 (m, 2H).

Example 20

4-{4-[(4'-chloro-1,1'-biphenyl-2-yl)methyl]piperazin-1-yl}-N-[(3-fluorophenyl)sulfonyl]benzamide The title compound was prepared by substituting EXAMPLE 5C and 3-fluorobenzenesulfonamide for EXAMPLE 1D and 3-nitrobenzenesulfonamide respectively, in EXAMPLE 1E. $^1$H NMR (300 MHz, dimethylsulfoxide-$d_6$) δ 7.82 (m, 1H), 7.77-7.68 (m, 5H), 7.59 (m, 1H), 7.52 (m, 4H), 7.40 (m, 2H), 7.34 (m, 1H), 6.93 (d, 2H), 4.23 (br s, 2H), 3.53 (m, 4H), 2.94 (m, 4H).

Example 21

4-{4-[(4'-chloro-1,1'-biphenyl-2-yl)methyl]piperazin-1-yl}-N-[(3-nitrophenyl)sulfonyl]-2-(phenylsulfinyl)benzamide

Example 21A methyl 4-fluoro-2-(phenylsulfinyl)benzoate

OXONE® (potassium peroxysulfate) (5.60 g) was added portionwise over 1 hour to EXAMPLE 13A (1.00 g) in a mixture of acetic acid (30 mL), water (30 mL) and CH$_2$Cl$_2$ (20 mL), and the reaction was stirred for an additional 1 hour. The reaction mixture was taken up in ethyl acetate, washed with Na$_2$S$_2$O$_3$ solution, water, and brine, concentrated, and chromatographed on silica gel with 5-25% ethyl acetate/hexanes.

Example 21B methyl 4-(4-((4'-chlorobiphenyl-2-yl)methyl)piperazin-1-yl)-2-(phenylsulfinyl)benzoate The title compound was prepared by substituting EXAMPLE 21A for EXAMPLE 7C in EXAMPLE 7D.

Example 21C 4-(4-((4'-chlorobiphenyl-2-yl)methyl)piperazin-1-yl)-2-(phenylsulfinyl)benzoic acid The title compound was prepared by substituting EXAMPLE 21B for EXAMPLE 5B in EXAMPLE 5C.

Example 21D

4-{4-[(4'-chloro-1,1'-biphenyl-2-yl)methyl]piperazin-1-yl}-N-[(3-nitrophenyl)sulfonyl]-2-(phenylsulfinyl)benzamide The title compound was prepared by substituting EXAMPLE 21C for EXAMPLE 1D in EXAMPLE 1E. The reaction was chromatographed on silica gel with 20-50% ethyl acetate/hexanes. $^1$H NMR (300 MHz, dimethylsulfoxide-$d_6$) δ 8.53 (d, 1H), 8.28 (d, 1H), 8.14 (d, 1H), 7.875 (d, 1H), 7.69 (dd, 1H), 7.62 (s, 1H), 7.37-7.51 (m, 7H), 7.23 (m, 2H), 7.15 (m, 3H), 6.95 (d, 2H), 3.42 (s, 2H), 3.26 (m, 4H), 2.48 (m, 4H).

Example 22

4-{4-[(4'-chloro-1,1'-biphenyl-2-yl)methyl]piperazin-1-yl}-N-[(4-nitrophenyl)sulfonyl]-2-phenoxybenzamide The title compound was prepared by substituting EXAMPLE 9C and 4-nitrobenzenesulfonamide for EXAMPLE 1D and 3-nitrobenzenesulfonamide respectively, in EXAMPLE 1E. $^1$H NMR (300 MHz, dimethylsulfoxide-$d_6$) δ 12.14 (br s, 1H), 8.31 (d, 2H), 8.02 (d, 2H), 7.70 (br s, 1H), 7.51 (m, 5H), 7.38 (d, 2H), 7.32 (d, 1H), 7.26 (t, 2H), 7.02 (t, 1H), 6.78 (m, 3H), 6.46 (s, 1H), 4.31 (br s, 2H), 3.74 (m, 2H), 3.05 (m, 4H), 2.80 (m, 2H).

Example 23

4-{4-[(4'-chloro-1,1'-biphenyl-2-yl)methyl]piperazin-1-yl}-N-[(3-fluorophenyl)sulfonyl]-2-phenoxybenzamide The title compound was prepared by substituting EXAMPLE 9C and 3-fluorobenzenesulfonamide for EXAMPLE 1D and 3-nitrobenzenesulfonamide respectively, in EXAMPLE 1E. $^1$H NMR (300 MHz, dimethylsulfoxide-$d_6$) δ 11.89 (br s, 1H), 7.70 (br s, 1H), 7.65 (m, 1H), 7.59 (m, 3H), 7.52 (m, 5H), 7.38 (d, 2H), 7.32 (m, 3H), 7.07 (t, 1H), 6.85 (d, 2H), 6.77 (dd, 1H), 6.44 (s, 1H), 4.35 (br s, 2H), 3.77 (m, 2H), 3.24 (m, 2H), 3.03 (m, 2H), 2.86 (m, 2H).

Example 24

4-{4-[(4'-chloro-1,1'-biphenyl-2-yl)methyl]piperazin-1-yl}-N-[(4-fluorophenyl)sulfonyl]-2-phenoxybenzamide The title compound was prepared by substituting EXAMPLE 9C and 4-fluorobenzenesulfonamide for EXAMPLE 1D and 3-nitrobenzenesulfonamide respectively, in EXAMPLE 1E. $^1$H NMR (300 MHz, dimethylsulfoxide-$d_6$) δ 11.80 (br s, 1H), 7.85 (m, 2H), 7.70 (br s, 1H), 7.51 (m, 5H), 7.39-7.29 (m, 7H), 7.08 (t, 1H), 6.85 (d, 2H), 6.77 (dd, 1H), 6.44 (s, 1H), 4.34 (br s, 2H), 3.74 (m, 2H), 3.03 (m, 4H), 2.82 (m, 2H).

Example 25

4-{4-[(4'-chloro-1,1'-biphenyl-2-yl)methyl]piperazin-1-yl}-2-methoxy-N-[(3-nitrophenyl)sulfonyl]benzamide

Example 25A methyl 4-(4-((4'-chlorobiphenyl-2-yl)methyl)piperazin-1-yl)-2-methoxybenzoate Methyl 4-bromo-2-methoxybenzoate (700 mg), EXAMPLE 7B (983 mg), K$_3$PO$_4$ (909 mg), tris(dibenzylideneacetone)dipalladium(0) (78 mg), and 2-(di-t-butylphosphino)biphenyl (102 mg) were stirred in 1,2-dimethoxyethane (10 mL) at 80° C. for 24 hours. The reaction mixture was chromatographed on silica gel with 20-50% ethyl acetate/hexanes.

Example 25B 4-(4-((4'-chlorobiphenyl-2-yl)methyl)piperazin-1-yl)-2-methoxybenzoic acid The title compound was prepared by substituting EXAMPLE 25A for EXAMPLE 5B in EXAMPLE 5C.

Example 25C

4-{4-[(4'-chloro-1,1'-biphenyl-2-yl)methyl]piperazin-1-yl}-2-methoxy-N-[(3-nitrophenyl)sulfonyl] benzamide The title compound was prepared by substituting EXAMPLE 25B for EXAMPLE 1D in EXAMPLE 1E. The reaction was chromatographed on silica gel with 20-50% ethyl acetate/hexanes. $^1$H NMR (300 MHz, dimethylsulfoxide-$d_6$) δ 11.15 (br s, 1H), 8.73 (d, 1H), 8.53 (d, 1H), 8.39 (d, 1H), 7.91 (dd, 2H), 7.34-7.55 (m, 7H), 7.27 (m, 1H), 6.50 (m, 2H), 3.88 (s, 3H), 3.43 (s, 2H), 3.28 (m, 4H), 2.40 (m, 4H).

Example 26

4-{4-[(4'-chloro-1,1'-biphenyl-2-yl)methyl]piperazin-1-yl}-N-[(3-nitrophenyl)sulfonyl]-2-(phenylsulfonyl)benzamide Example 26A methyl 4-fluoro-2-(phenylsulfonyl)benzoate EXAMPLE 13A (0.30 g) and KMnO$_4$ (1.80 g) were stirred in acetic acid (40 mL) at 60° C. for 24 hours. The reaction mixture was filtered through a plug of silica gel, concentrated, and chromatographed on silica gel with 50% ethyl acetate/hexanes.

Example 26B methyl 4-(4-((4'-chlorobiphenyl-2-yl)methyl)piperazin-1-yl)-2-(phenylsulfonyl)benzoate The title compound was prepared by substituting EXAMPLE 26A for EXAMPLE 7C in EXAMPLE 7D.

Example 26C 4-(4-((4'-chlorobiphenyl-2-yl)methyl)piperazin-1-yl)-2-(phenylsulfonyl)benzoic acid The title compound was prepared by substituting EXAMPLE 26B for EXAMPLE 5B in EXAMPLE 5C.

Example 26D

4-{4-[(4'-chloro-1,1'-biphenyl-2-yl)methyl]piperazin-1-yl}-N-[(3-nitrophenyl)sulfonyl]-2-(phenylsulfonyl)benzamide The title compound was prepared by substituting EXAMPLE 26C for EXAMPLE 1D in EXAMPLE 1E. The reaction was chromatographed on silica gel with 20-50% ethyl acetate/hexanes. $^1$H NMR (300 MHz, dimethylsulfoxide-$d_6$) δ 11.90 (br s, 1H), 8.66 (d, 1H), 8.30 (d, 1H), 8.24 (d, 1H), 7.73 (dd, 2H), 7.74 (d, 1H), 7.32-7.56 (m, 13H), 7.25 (m, 1H), 7.12 (d, 1H), 3.41 (s, 2H), 3.06 (m, 4H), 2.44 (m, 4H).

Example 27

4-{4-[(4'-chloro-1,1'-biphenyl-2-yl)methyl]piperazin-1-yl}-N-[(4-chloro-3-nitrophenyl)sulfonyl]-2-phenoxybenzamide The title compound was prepared by substituting EXAMPLE 9C for EXAMPLE 1D and 4-chloro-3-nitrobenzenesulfonamide for 3-nitrobenzenesulfonamide in EXAMPLE 1E, except here the purification was done by flash column chromatography on silica gel with 50% ethyl acetate (in hexanes). $^1$H NMR (400 MHz, dimethylsulfoxide-$d_6$) δ 8.33 (br s, 1H), 7.96 (d, 1H), 7.85 (d, 1H), 7.56 (d, 2H), 7.50-7.39 (m, 6H), 7.28-7.25 (m, 1H), 7.21 (t, 2H), 6.95 (t, 1H), 6.75 (d, 3H), 6.42 (d, 1H), 3.30 (br s, 4H), 3.20 (br s, 2H), 2.51 (br s, 4H).

Example 28

4-[4-({4'-chloro-3-[2-(dimethylamino)ethoxy]-1,1'-biphenyl-2-yl}methyl)piperazin-1-yl]-2-(1H-indol-4-yloxy)-N-[(3-nitrophenyl)sulfonyl]benzamide Example 28A 4'-chloro-3-hydroxybiphenyl-2-carbaldehyde The title compound was prepared by substituting 2-bromo-6-hydroxybenzaldehyde for EXAMPLE 5A in EXAMPLE 5B.

Example 28B tert-butyl 4-((4'-chloro-3-hydroxybiphenyl-2-yl)methyl)piperazine-1-carboxylate The title compound was prepared by substituting EXAMPLE 28A for 4'-chlorobiphenyl-2-carboxaldehyde in EXAMPLE 7A.

Example 28C tert-butyl 4-((4'-chloro-3-(2-(dimethylamino)ethoxy)biphenyl-2-yl)methyl)piperazine-1-carboxylate EXAMPLE 28B (500 mg, 1.24 mmol) was dissolved in anhydrous N,N-dimethylformamide (8 mL) and NaH (60% mineral oil suspension, 150 mg, 3.72 mmol) was added. The reaction mixture was stirred at room temperature for 15 minutes under N$_2$, followed by the addition of 2-chloro-N,N-dimethylethanamine hydrochloride salt (360 mg, 2.48 mmol). The reaction mixture was stirred at room temperature for 16 hours. The reaction was quenched with saturated NH$_4$Cl aqueous solution, extracted with ethyl acetate, and the organic layer was washed with water and brine, and dried over Na$_2$SO$_4$. After filtration, the filtrate was concentrated to afford an oil residue which was used in the next step without further purification.

Example 28D 2-(4'-chloro-2-(piperazin-1-ylmethyl)biphenyl-3-yloxy)-N,N-dimethylethanamine The title compound was prepared by substituting EXAMPLE 28C for EXAMPLE 7A in EXAMPLE 7B.

Example 28E methyl 2-(1H-indol-4-yloxy)-4-fluorobenzoate

Methyl 2,4-difluorobenzoate (2 g, 11.6 mmol)), $K_3PO_4$ (2.4 g, 11.3 mmol) and 4-hydroxyindazole (1.40 g, 10.5 mmol) were stirred at 115° C. in diglyme (20 mL) for 24 hours. The reaction was cooled and poured into ether. The solution was washed three times with 1M NaOH solution, followed by brine, and then dried over $Na_2SO_4$ and filtered. The filtrate was then concentrated, and the crude product was chromatographed on silica gel with 20% ethyl acetate/hexanes.

Example 28F methyl 2-(1H-indol-4-yloxy)-4-(4-((4'-chloro-3-(2-(dimethylamino)ethoxy)biphenyl-2-yl)methyl)piperazin-1-yl)benzoate A solution of EXAMPLE 28D (100 mg, 0.269 mmol) and EXAMPLE 28E (161 mg, 0.538 mmol) in dimethylsulfoxide (15 ml) was treated with potassium phosphate dibasic (94 mg, 0.538 mmol) at 135° C. overnight. The reaction mixture was cooled to room temperature and diluted with dichloromethane. The organic layer was washed with water and brine, and concentrated. The residue was purified by 0%-10% 7N ammonia in methanol/dichloromethane.

Example 28G 2-(1H-indol-4-yloxy)-4-(4-((4'-chloro-3-(2-(dimethylamino)ethoxy)biphenyl-2-yl)methyl)piperazin-1-yl)benzoic acid The title compound was prepared by substituting EXAMPLE 28F for EXAMPLE 5B in EXAMPLE 5C.

Example 28H

4-[4-({4'-chloro-3-[2-(dimethylamino)ethoxy]-1,1'-biphenyl-2-yl}methyl)piperazin-1-yl]-2-(1H-indol-4-yloxy)-N-[(3-nitrophenyl)sulfonyl]benzamide The title compound was prepared by substituting EXAMPLE 28G for EXAMPLE 1D in EXAMPLE 1E. $^1$H NMR (400 MHz, dimethylsulfoxide-$d_6$) δ 11.08 (br s, 1H), 8.43 (t, 1H), 8.19 (dd, 1H), 7.98 (d, 1H), 7.63 (d, 1H), 7.50-7.43 (m, 5H), 7.35 (m, 1H), 7.19 (t, 1H), 7.10-7.01 (m, 2H), 6.86 (m, 2H), 6.62 (dd, 1H), 6.21 (m, 3H), 4.28 (m, 2H), 2.92(m, 4H), 2.76(s, 6H), 2.46 (m, 2H), 2.30 (m, 6H).

Example 29

4-[4-({4'-chloro-3-[2-(dimethylamino)ethoxy]-1,1'-biphenyl-2-yl}methyl)piperazin-1-yl]-2-(1H-indol-4-yloxy)-N-(phenylsulfonyl)benzamide This example was prepared by substituting EXAMPLE 28G and benzenesulfonamide for EXAMPLE 1D and 3-nitrobenzenesulfonamide respectively, in EXAMPLE 1E. $^1$H NMR (400 MHz, DMSO-$d_6$) δ 11.31 (s, 1H), 7.73 (m, 2H), 7.57 (d, 1H), 7.51 (m, 3H), 7.37-7.44 (m, 4H), 7.28 (m, 2H), 7.16 (d, 1H), 7.05 (d, 1H), 6.97 (m, 1H), 6.84(d, 1H), 6.67 (dd, 1H), 6.38 (d, 1H), 6.28 (m, 1H), 6.25 (d, 1H), 4.15 (m, 2H), 3.29(m, 2H), 2.96(m, 6H), 2.46 (s, 6H), 2.28 (m, 4H).

Example 30

4-(4-{[2-(4-chlorophenyl)-4,4-dimethylcyclohex-1-en-1-yl]methyl}piperazin-1-yl)-2-(1H-indol-5-yloxy)-N-[(3-nitrophenyl)sulfonyl]benzamide

Example 30A ethyl 2-(1H-indol-5-yloxy)-4-fluorobenzoate

Ethyl 2,4-difluorobenzoate (1.14 g), $K_3PO_4$ (1.30 g) and 5-hydroxyindole (0.90 g) were stirred at 110° C. in diglyme (12 mL) for 24 hours. The reaction was cooled and poured into ether. The solution was washed three times with 1M aqueous NaOH solution, and brine, and dried over $Na_2SO_4$. The solution was then filtered, concentrated, and the crude product was chromatographed on silica gel with 20% ethyl acetate/hexanes.

Example 30B methyl 4,4-dimethyl-2-(trifluoromethylsulfonyloxy)cyclohex-1-enecarboxylate To a suspension of hexane washed NaH (17 g) in dichloromethane (700 mL), 5,5-dimethyl-2-methoxycarbonylcyclohexanone (38.5 g) was added dropwise at 0° C. After stirring for 30 minutes, the mixture was cooled to −78° C. and trifluoromethanesulfonic anhydride (40 mL) was added. The reaction mixture was warmed to room temperature and stirred for 24 hours. The organic layer was washed with brine, dried over $Na_2SO_4$, filtered, and concentrated to give the product.

Example 30C methyl 2-(4-chlorophenyl)-4,4-dimethylcyclohex-1-enecarboxylate

EXAMPLE 30B (62.15 g), 4-chlorophenylboronic acid (32.24 g), CsF (64 g) and tetrakis(triphenylphosphine)palladium(0) (2 g) in 2:1 1,2-dimethoxyethane/methanol (600 mL) were heated to 70° C. for 24 hours. The mixture was concentrated. Ether (4×200 mL) was added and the mixture was filtered. The combined ether solution was concentrated to give the product.

Example 30D (2-(4-chlorophenyl)-4,4-dimethylcyclohex-1-enyl)methanol

To a mixture of LiBH$_4$ (13 g), EXAMPLE 30C (53.8 g) and ether (400 mL), methanol (25 mL) was added slowly by syringe. The mixture was stirred at room temperature for 24 hours. The reaction was quenched with 1N aqueous HCl with ice-cooling. The mixture was diluted with water and extracted by ether (3×100 mL). The extracts were dried over $Na_2SO_4$, filtered, and concentrated. The crude product was chromatographed on silica gel with 0-30% ethyl acetate/hexanes.

Example 30E 2-(4-chlorophenyl)-4,4-dimethylcyclohex-1-enecarbaldehyde

To a mixture of EXAMPLE 30D (1.25 g) in dichloromethane (20 ml) was slowly added Dess-Martin Periodinane (2.78 g). The reaction mixture was stirred at room temperature for 3 hours and diluted with ether. The resulting mixture was washed with aqueous NaOH and water. The organic layer was dried over $Na_2SO_4$, filtered, and concentrated. The residue was purified by flash chromatography, eluting with 0-100% dichloromethane in hexane to provide the title compound.

Example 30F tert-butyl 4-((2-(4-chlorophenyl)-4,4-dimethylcyclohex-1-enyl)methyl)piperazine-1-carboxylate This example was prepared by substituting EXAMPLE 30E for 4'-chlorobiphenyl-2-carboxaldehyde in EXAMPLE 7A.

Example 30G 1-((2-(4-chlorophenyl)-4,4-dimethylcyclohex-1-enyl)methyl)piperazine This EXAMPLE was prepared by substituting EXAMPLE 30F for EXAMPLE 7A in EXAMPLE 7B.

Example 30H ethyl 2-(1H-indol-5-yloxy)-4-(4-((2-(4-chlorophenyl)-4,4-dimethylcyclohex-1-enyl)methyl)piperazin-1-yl)benzoate EXAMPLE 30A (330 mg), EXAMPLE 30G (335 mg), and $HK_2PO_4$ (191 mg) were stirred in dimethylsulfoxide (5 mL) at 140° C. for 24 hours. The reaction was diluted with ethyl acetate, washed three times with water, washed with brine, dried over $Na_2SO_4$, filtered, and concentrated. The crude product was chromatographed on silica gel with 30% ethyl acetate/hexanes.

Example 30I 2-(1H-indol-5-yloxy)-4-(4-((2-(4-chlorophenyl)-4,4-dimethylcyclohex-1-enyl)methyl)piperazin-1-yl) benzoic acid This example was prepared by substituting EXAMPLE 30H for EXAMPLE 5B in EXAMPLE 5C.

Example 30J 4-(4-{[2-(4-chlorophenyl)-4,4-dimethylcyclohex-1-en-1-yl]methyl}piperazin-1-yl)-2-(1H-indol-5-yloxy)-N-[(3-nitrophenyl)sulfonyl]benzamide This example was prepared by substituting EXAMPLE 30I for EXAMPLE 1D in EXAMPLE 1E.

Example 31

4-(4-{[2-(4-chlorophenyl)-4,4-dimethylcyclohex-1-en-1-yl]methyl}piperazin-1-yl)-2-(1H-indol-5-yloxy)-N-(phenylsulfonyl)benzamide This example was prepared by substituting benzenesulfonamide for 3-nitrobezenesulfonamide and EXAMPLE 30I for EXAMPLE 1D in EXAMPLE 1E. $^1$H NMR (300 MHz, dimethylsulfoxide-d6) δ 11.19 (s, 1H), 7.88 (d, 2H), 7.65 (t, 1H), 7.48 (m, 5H), 7.33 (d, 2H), 7.20 (d, 1H), 7.03 (d, 2H), 6.88 (dd, 1H), 6.64 (dd, 1H), 6.42 (m, 1H), 6.13 (d, 1H), 3.03 (m, 4H), 2.72 (m, 2H), 2.18 (m, 6H), 1.94 (m, 2H), 1.39 (t, 2H), 0.92 (s, 6H).

Example 32

4-(4-{[2-(4-chlorophenyl)-4,4-dimethylcyclohex-1-en-1-yl]methyl}piperazin-1-yl)-N-[(3-cyanophenyl)sulfonyl]-2-(1H-indol-5-yloxy)benzamide This example was prepared by substituting 3-cyanobenzenesulfonamide for 3-nitrobezenesulfonamide and EXAMPLE 30I for EXAMPLE 1D in EXAMPLE 1E. $^1$H NMR (300 MHz, dimethylsulfoxide-d6) δ 11.14 (s, 1H), 8.28 (br s, 1H), 8.12 (d, 1H), 8.06 (d, 1H), 7.66 (t, 1H), 7.51 (d, 1H), 7.37 (m, 4H), 7.13 (d, 1H), 7.04 (d, 2H), 6.83 (dd, 1H), 6.64 (dd, 1H), 6.38 (m, 1H), 6.16 (d, 1H), 3.06 (m, 4H), 2.83 (m, 2H), 2.27 (m, 4H), 2.15 (m, 2H), 1.96 (s, 2H), 1.39 (t, 2H), 0.92 (s, 6H).

Example 33

4-(4-{[2-(4-chlorophenyl)-4,4-dimethylcyclohex-1-en-1-yl]methyl}piperazin-1-yl)-2-(1H-indol-5-yloxy)-N-{[3-(trifluoromethyl)phenyl]sulfonyl}benzamide This example was prepared by substituting 3-(trifluoromethyl)benzenesulfonamide for 3-nitrobezenesulfonamide and EXAMPLE 30I for EXAMPLE 1D in EXAMPLE 1E. $^1$H NMR (300 MHz, dimethylsulfoxide-d6) δ 11.15 (s, 1H), 8.20 (br s, 1H), 8.12 (d, 1H), 8.02 (d, 1H), 7.73 (t, 1H), 7.50 (d, 1H), 7.39 (m, 2H), 7.33 (d, 2H), 7.16 (d, 1H), 7.03 (d, 2H), 6.84 (dd, 1H), 6.63 (dd, 1H), 6.39 (t, 1H), 6.14 (d, 1H), 3.04 (m, 4H), 2.79 (m, 2H), 2.24 (m, 4H), 2.15 (m, 2H), 1.95 (m, 2H), 1.39 (t, 2H), 0.92 (s, 6H).

Example 34

4-(4-{[2-(4-chlorophenyl)-4,4-dimethylcyclohex-1-en-1-yl]methyl}piperazin-1-yl)-N-[(3-chlorophenyl)sulfonyl]-2-(1H-indol-5-yloxy)benzamide This example was prepared by substituting 3-chlorobenzenesulfonamide for 3-nitrobezenesulfonamide and EXAMPLE 30I for EXAMPLE 1D in EXAMPLE 1E. $^1$H NMR (300 MHz, dimethylsulfoxide-d6) δ 11.15 (s, 1H), 7.90 (m, 1H), 7.80 (d, 1H), 7.70 (d, 1H), 7.52 (m, 2H), 7.40 (m, 2H), 7.33 (d, 2H), 7.17 (d, 1H), 7.03 (d, 2H), 6.85 (dd, 1H), 6.63 (dd, 1H), 6.40 (t, 1H), 6.15 (d, 1H), 3.03 (m, 4H), 2.74 (m, 2H), 2.19 (m, 6H), 1.95 (m, 2H), 1.38 (t, 2H), 0.92 (s, 6H).

Example 35

4-(4-{[2-(4-chlorophenyl)-4,4-dimethylcyclohex-1-en-1-yl]methyl}piperazin-1-yl)-N-[(3-fluorophenyl)sulfonyl]-2-(1H-indol-5-yloxy)benzamide This example was prepared by substituting 3-fluorobenzenesulfonamide for 3-nitrobezenesulfonamide and EXAMPLE 30I for EXAMPLE 1D in EXAMPLE 1E. $^1$H NMR (300 MHz, dimethylsulfoxide-d6) δ 11.01 (s, 1H), 8.20 (m, 3H), 7.54 (m, 2H), 7.34 (d, 2H), 7.29 (m, 2H), 7.04 (d, 2H), 6.92 (m, 2H), 6.70 (dd, 1H), 6.56 (dd, 1H), 6.30 (t, 1H), 6.15 (d, 1H), 2.97 (m, 4H), 2.74 (m, 2H), 2.17 (m, 6H), 1.95 (m, 2H), 1.38 (t, 2H), 0.92 (s, 6H).

Example 36

4-(4-{[2-(4-chlorophenyl)-4,4-dimethylcyclohex-1-en-1-yl]methyl}piperazin-1-yl)-2-(1H-indol-5-yloxy)-N-(2-naphthylsulfonyl)benzamide This example was prepared by substituting EXAMPLE 30I for EXAMPLE 1D and naphthalene-2-sulfonamide for 3-nitrobenzenesulfonamide in EXAMPLE 1E. $^1$H NMR (500 MHz, dimethylsulfoxide-d$_6$) δ 11.27 (s, 1H), 11.20 (s, 1H), 8.58 (s, 1H), 8.12 (d, 1H), 8.02 (dd, 2H), 7.87 (dd, 1H), 7.72 (t, 1H), 7.66 (t, 1H), 7.48 (d, 1H), 7.40-7.45 (m, 2H), 7.33 (d, 2H), 7.22 (d, 1H), 7.03 (d, 2H), 6.89 (dd, 1H), 6.63 (dd, 1H), 6.42 (s, 1H), 6.14 (d, 1H), 3.02 (s, 4H), 2.71 (s, 2H), 2.09-2.21 (m, 6H), 1.94 (s, 2H), 1.37 (t, 2H), 0.91 (s, 6H)

Example 37

4-(4-{[2-(4-chlorophenyl)-4,4-dimethylcyclohex-1-en-1-yl]methyl}piperazin-1-yl)-2-(1H-indol-5-yloxy)-N-(isoquinolin-5-ylsulfonyl)benzamide

Example 37A isoquinoline-5-sulfonamide

Isoquinoline-5-sulfonyl chloride (528 mg) was dissolved in tetrahydrofuran (8 mL), cooled to 0° C., then concentrated NH$_4$OH (0.7 mL) was added and the reaction was allowed to come to room temperature overnight. The product was filtered off, washed with water, and dried under vacuum.

Example 37B

4-(4-{[2-(4-chlorophenyl)-4,4-dimethylcyclohex-1-en-1-yl]methyl}piperazin-1-yl)-2-(1H-indol-5-yloxy)-N-(isoquinolin-5-ylsulfonyl)benzamide This example was made by substituting EXAMPLE 37A for 3-nitrobezenesulfonamide and EXAMPLE 30I for EXAMPLE 1D in EXAMPLE 1E. $^1$H NMR (300 MHz, dimethylsulfoxide-d6) δ 11.17 (s, 1H), 9.43 (s, 1H), 8.50 (d, 1H), 8.42 (d, 1H), 8.39 (s, 2H), 7.82 (t, 1H), 7.40 (m, 3H), 7.34 (d, 2H), 7.15 (s, 1H), 7.04 (d, 2H), 6.78 (dd, 1H), 6.60 (dd, 1H), 6.40 (s, 1H), 6.12 (d, 1H), 3.01 (br s, 4H), 2.80 (v br s, 2H), 2.25 (v br s, 4H), 2.13 (br t, 2H), 1.95 (s, 2H), 1.38 (t, 2H), 0.92 (s, 6H).

Example 38

N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide

Example 38A

4-Hydroxy-indazole-1-carboxylic acid tert-butyl ester and 4-Hydroxy-indazole-2-carboxylic acid tert-butyl ester 4-Hydroxyindazole (3.94 g) was added to tetrahydrofuran (250 mL) and cooled to 0° C. using an ice bath. Sodium hydride (60% dispersion in mineral oil, 1.23 g) was added, and the mixture was stirred at 0° c for five minutes. The solution was allowed to warm to room temperature and stirred for an additional 20 minutes. The solution was again cooled to 0° C. using an ice bath, and tert-butyldimethylchlorosilane (4.65 g) was added. The solution was allowed to warm to room temperature and was stirred for 16 hours. The solvent volume was reduced under vacuum, the residue vacuum filtered over a pad of silica gel and washed with ethyl acetate, and the solvent was removed under vacuum. To the residue was added acetonitrile (200 mL), di-tert-butyl dicarbonate (7.06 g), and 4-9dimethylamino)pyridine (0.359 g). The solution was stirred at room temperature for three hours, and the solvent was removed under vacuum. To the residue was added tetrahydrofuran (200 mL) and tetrabutylammonium fluoride (1M in tetrahyrdofuran, 82 mL). The solution was stirred at room temperature for four days, the solvent was removed under vacuum, and the residue taken up in ethyl acetate. The solution was extracted with saturated aqueous ammonium chloride, extracted with brine, and dried on anhydrous sodium sulfate. The solution was vacuum-filtered over silica gel, and the solvent removed under vacuum.

Example 38B

4-Fluoro-2-(1H-indazol-4-yloxy)-benzoic acid methyl ester

EXAMPLE 38A (5.56 g) was added to diglyme (200 mL), and potassium tert-butoxide (1M in tetrahydrofuran, 30.8 mL) was added. The solution was mixed at room temperature for 15 minutes, methyl 2,4-difluorobenzoate was added, and the solution was heated at 115° C. for 16 hours. The solution was cooled, the solvent was removed under vacuum, the residue was taken up in dichloromethane (100 mL), and trifluoroacetic acid (22.6 mL) was added. The solution was stirred at room temperature for 16 hours, the solvent removed under vacuum, the residue was taken up in ethyl acetate and washed with a saturate aqueous sodium bicarbonate solution, and the organic layer was dried with anhydrous sodium sulfate. The material was purified by flash column chromatography on silica gel using 30% ethyl acetate (hexanes) increasing to 40% ethyl acetate (hexanes).

Example 38C 2-(1H-Indazol-4-yloxy)-4-piperazin-1-yl-benzoic acid methyl ester EXAMPLE 38B (2.00 g) and piperazine (2.71 g) were added to dimethylsulfoxide (60 mL) and the mixture was heated to 100° C. for one hour. The solution was cooled, added to dichloromethane, washed with water twice, washed with a saturated aqueous sodium bicarbonate solution, and dried on anhydrous sodium sulfate. The solvent was removed under vacuum.

Example 38D

4-{4-[2-(4-Chloro-phenyl)-4,4-dimethyl-cyclohex-1-enylmethyl]-piperazin-1-yl}-2-(1H-indazol-4-yloxy)-benzoic acid methyl ester This example was prepared by substituting EXAMPLE 30E for 4'-chlorobiphenyl-2-carboxaldehyde and EXAMPLE 38C for tert-butyl piperazine-1-carboxylate in EXAMPLE 7A.

Example 38E

4-{4-[2-(4-Chloro-phenyl)-4,4-dimethyl-cyclohex-1-enylmethyl]-piperazin-1-yl}-2-(1H-indazol-4-yloxy)-benzoic acid This example was prepared by substituting EXAMPLE 38D for EXAMPLE 5B in EXAMPLE 5C.

Example 38F

N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide This example was prepared by substituting EXAMPLE 38E for EXAMPLE 1D and 4-chloro-3-nitrobenzenesulfonamide for 3-nitrobenzenesulfonamide in EXAMPLE 1E. $^1$H NMR (300 MHz, dimethylsulfoxide-$d_6$) δ 13.04 (s, 1H), 8.17 (br s, 1H), 7.75 (s, 1H), 7.73 (d, 1H), 7.66-7.61 (m, 2H), 7.38 (d, 2H), 7.11-7.01 (m, 4H), 6.79 (dd, 1H), 6.54 (d, 1H), 6.10 (dd, 1H), 3.38-3.05 (m, 8H), 2.73 (br s, 2H), 2.19 (m, 2H), 2.00 (br s, 2H), 1.44 (t, 2H), 0.95 (s, 6H).

Example 39

4-{4-[(4'-chlorobiphenyl-2-yl)methyl]piperazin-1-yl}-N-[(2-chloropyridin-3-yl)sulfonyl]benzamide This compound was prepared by substituting EXAMPLE 5C and 2-chloropyridine-3-sulfonamide for EXAMPLE 1D and 3-nitrobenzenesulfonamide respectively, in EXAMPLE 1E. $^1$H NMR (300 MHz, DMSO-$d_6$) δ 9.70 (m, 1H), 8.67 (m, 1H), 8.54 (m, 1H), 7.77 (m, 4H), 7.53 (m, 4H), 7.36 (m, 3H), 6.93 (m, 2H), 4.36 (m, 2H), 3.93 (m, 2H), 3.27 (m, 2H), 3.11 (m, 2H), 2.89 (m, 2H).

Example 40

4-{4-[(4'-chlorobiphenyl-2-yl)methyl]piperazin-1-yl}-N-[(7-nitro-1H-benzimidazol-5-yl)sulfonyl]benzamide The title compound was prepared by substituting EXAMPLE 5C and 7-nitro-1H-benzo[d]imidazole-5-sulfonamide for EXAMPLE 1D and 3-nitrobenzenesulfonamide respectively, in EXAMPLE 1E. $^1$H NMR (300 MHz, dimethylsulfoxide-$d_6$) δ 8.70 (s, 1H), 8.65 (dd, 2H), 7.75 (m, 3H), 7.54 (m, 4H), 7.37 (m, 3H), 6.92 (d, 2H), 4.70 (s, 2H), 4.32 (br s, 2H), 3.77 (br s, 2H), 3.27, 3.18, 2.91 (all br s, total 6H).

Example 41

4-{4-[(4'-chlorobiphenyl-2-yl)methyl]piperazin-1-yl}-N-[(3-oxo-3,4-dihydro-2H-1,4-benzoxazin-6-yl)sulfonyl]benzamide The title compound was prepared by substituting EXAMPLE 5C for EXAMPLE 1D and 3-oxo-3,4-dihydro-2H-benzo[b][1,4]oxazine-6-sulfonamide for 3-nitrobenzenesulfonamide in EXAMPLE 1E, except here the purification was done by preparative HPLC using a C18 column, 250×50 mm, 10μ, and eluting with a gradient of 20-100% CH$_3$CN vs. 0.1% TFA in water, giving the product as a trifluoroacetate salt. $^1$H NMR (300 MHz, dimethylsulfoxide-$d_6$) δ 12.08 (v br s, 1H), 11.02 (s, 1H), 7.77 (d, 3H), 7.55 (m, 6H), 7.40 (m, 3H), 7.14 (d, 1H), 6.92 (d, 2H), 4.70 (s, 2H), 4.38 (br s, 1H), 3.77 (br s, 1H), 3.45 (m, 2H), 3.25, 3.10, 2.94 (all br s, total 6H).

Example 42

4-{4-[(4'-chlorobiphenyl-2-yl)methyl]piperazin-1-yl}-N-[(6-chloro-1,1-dioxido-2H-1,2,4-benzothiadiazin-7-yl)sulfonyl]benzamide This EXAMPLE was prepared by substituting EXAMPLE 5C for EXAMPLE 1D and chlorothizaide for 3-nitrobenzenesulfonamide in EXAMPLE 1E. $^1$H NMR (400 MHz, dimethylsulfoxide-$d_6$) δ 8.36 (s, 1H), 8.10 (s, 1H), 7.78 (d, 2H), 7.64 (s, 1H), 7.50 (m, 7H), 7.28 (m, 1H), 6.88 (d, 2H), 3.32 (m, 10H).

Example 43

4-{4-[(4'-chlorobiphenyl-2-yl)methyl]piperazin-1-yl}-N-({5-[ethyl(trifluoroacetyl)amino]-1-naphthyl}sulfonyl)benzamide

Example 43A

N-ethyl-2,2,2-trifluoro-N-(5-sulfamoylnaphthalen-1-yl)acetamide 5-(N-ethyl-2,2,2-trifluoroacetamido)naphthalene-1-sulfonyl chloride (100 mg) was dissolved in tetrahydrofuran (1.0 mL), cooled to 0° C., then concentrated ammonia (0.11 mL) was added. The reaction was stirred at 0° C. for 3 hours, then concentrated and partitioned between water and ethyl acetate. The organic layer was dried over Na$_2$SO$_4$, filtered, and concentrated to give the title compound.

Example 43B

4-{4-[(4'-chlorobiphenyl-2-yl)methyl]piperazin-1-yl}-N-({5-[ethyl(trifluoroacetyl)amino]-1-naphthyl}sulfonyl)benzamide The title compound was prepared by substituting EXAMPLE 5C for EXAMPLE 1D and EXAMPLE 43A for 3-nitrobenzenesulfonamide in EXAMPLE 1E, except here the purification was done by preparative HPLC using a C18 column, 250×50 mm, 10µ, and eluting with a gradient of 20-100% CH$_3$CN vs. 0.1% TFA in water, giving the product as a trifluoroacetate salt. $^1$H NMR (300 MHz, dimethylsulfoxide-d$_6$) δ 12.50 (v br s, 1H), 9.58 (v br s, 1H), 8.83 (d, 1H), 8.45 (d, 1H), 8.30 (d, 1H), 7.85 (m, 1H) 7.78 (m, 5H), 7.55 (d, 4H), 7.39 (m, 3H), 6.90 (d, 2H), 4.38 (br s, 1H), 4.25 (m, 1H), 3.83 (br s, 1H), 3.45 (m, 2H), 3.30 (m, 1H) 3.25, 3.10, 2.85 (all br s, total 6H), 1.12 (t, 3H).

Example 44

4-{4-[(4'-chlorobiphenyl-2-yl)methyl]piperazin-1-yl}-N-[(5,5,8,8-tetramethyl-5,6,7,8-tetrahydronaphthalen-2-yl)sulfonyl]benzamide The title compound was prepared by substituting EXAMPLE 5C and 5,5,8,8-tetramethyl-5,6,7,8-tetrahydronaphthalene-2-sulfonamide for EXAMPLE 1D and 3-nitrobenzenesulfonamide respectively, in EXAMPLE 1E. $^1$H NMR (300 MHz, dimethylsulfoxide-d$_6$) δ 12.00 (br s, 1H), 7.89 (d, 1H), 7.73 (d, 2H), 7.69 (dd, 1H), 7.55 (d, 2H), 7.47 (m, 4H), 7.37 (m, 2H), 7.24 (m, 1H), 6.90 (d, 2H), 3.40 (s, 2H), 3.24 (br m, 4H), 2.39 (br m, 4H), 1.66 (br s, 4H), 1.25 (s, 12H).

Example 45

4-{4-[(4'-chlorobiphenyl-2-yl)methyl]piperazin-1-yl}-N-[(2-oxo-2H-chromen-6-yl)sulfonyl]benzamide The title compound was prepared by substituting EXAMPLE 5C and 2-oxo-2H-chromene-6-sulfonamide for EXAMPLE 1D and 3-nitrobenzenesulfonamide respectively, in EXAMPLE 1E. $^1$H NMR (300 MHz, dimethylsulfoxide-d$_6$) δ 12.08 (v br s, 1H), 8.41 (d, 1H), 8.27 (d, 1H), 8.11 (dd, 1H), 7.75 (m, 3H), 7.61 (d, 1H), 7.54 (m, 4H), 7.40 (d, 2H), 7.34 (dd, 1H), 6.93 (d, 2H), 6.64 (d, 1H), 4.38 (br s, 2H), 3.88 (br s, 1H), 3.25, 3.10, 2.94 (all br s, total 6H).

What is claimed is:

1. A compound or therapeutically acceptable salt thereof, wherein the compound is chosen from:
   4-(4-{[2-(4-chlorophenyl)-4,4-dimethylcyclohex-1-en-1-yl]methyl}piperazin-1-yl)-2-(1H-indol-5-yloxy)-N-[(3-nitrophenyl)sulfonyl]benzamide;
   4-(4-{[2-(4-chlorophenyl)-4,4-dimethylcyclohex-1-en-1-yl]methyl}piperazin-1-yl)-2-(1H-indol-5-yloxy)-N-(phenylsulfonyl)benzamide;
   4-(4-{[2-(4-chlorophenyl)-4,4-dimethylcyclohex-1-en-1-yl]methyl}piperazin-1-yl)-N-[(3-cyanophenyl)sulfonyl]-2-(1H-indol-5-yloxy)benzamide;
   4-(4-{[2-(4-chlorophenyl)-4,4-dimethylcyclohex-1-en-1-yl]methyl}piperazin-1-yl)-2-(1H-indol-5-yloxy)-N-{[3-(trifluoromethyl)phenyl]sulfonyl}benzamide;
   4-(4-{[2-(4-chlorophenyl)-4,4-dimethylcyclohex-1-en-1-yl]methyl}piperazin-1-yl)-N-[(3-chlorophenyl)sulfonyl]-2-(1H-indol-5-yloxy)benzamide;
   4-(4-{[2-(4-chlorophenyl)-4,4-dimethylcyclohex-1-en-1-yl]methyl}piperazin-1-yl)-N-[(3-fluorophenyl)sulfonyl]-2-(1H-indol-5-yloxy)benzamide; and
   4-(4-{[2-(4-chlorophenyl)-4,4-dimethylcyclohex-1-en-1-yl]methyl}piperazin-1-yl)-2-(1H-indol-5-yloxy)-N-(2-naphthylsulfonyl)benzamide.

2. A composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, a lymphoid malignancy of T cell or B cell origin, melanoma, myelogenous leukemia, myeloma, oral cancer, ovarian cancer, non-small cell lung cancer, prostate cancer, small cell lung cancer or spleen cancer, said composition comprising an excipient and a therapeutically effective amount of the compound or therapeutically acceptable salt of claim 1.

3. 4-(4-{[2-(4-chlorophenyl)-4,4-dimethylcyclohex-1-en-1-yl]methyl}piperazin-1-yl)-2-(1H-indol-5-yloxy)-N-[(3-nitrophenyl)sulfonyl]benzamide or a therapeutically acceptable salt thereof.

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Probe Peptide
<220> FEATURE:
<221> NAME/KEY: MOD_RES
<222> LOCATION: 1
<223> OTHER INFORMATION: Gly is modified with acetyl
<220> FEATURE:
<221> NAME/KEY: MOD_RES
<222> LOCATION: 13
<223> OTHER INFORMATION: Lys is modified with 6-FAM
<220> FEATURE:
<221> NAME/KEY: MOD_RES
<222> LOCATION: 16
<223> OTHER INFORMATION: Arg is modified with NH2

<400> SEQUENCE: 1

Gly Gln Val Gly Arg Gln Leu Ala Ile Ile Gly Asp Lys Ile Asn Arg
 1               5                  10                  15
```

4. A composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, a lymphoid malignancy of T cell or B cell origin, melanoma, myelogenous leukemia, myeloma, oral cancer, ovarian cancer, non-small cell lung cancer, prostate cancer, small cell lung cancer or spleen cancer, said composition comprising an excipient and a therapeutically effective amount of the compound or therapeutically acceptable salt of claim 3.

* * * * *